US006333336B1

(12) United States Patent
Blackaby et al.

(10) Patent No.: US 6,333,336 B1
(45) Date of Patent: Dec. 25, 2001

(54) PYRAZOLO-PYRIDINE DERIVATIVES AS LIGANDS FOR GABA RECEPTORS

(75) Inventors: Wesley Peter Blackaby, Loughton; Jose Luis Castro Pineiro; Richard Thomas Lewis, both of Bishops Stortford; Michael Geoffrey Neil Russell, Welwyn Garden; Leslie Joseph Street, Little Hallingbury, all of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/622,878

(22) PCT Filed: Mar. 16, 1999

(86) PCT No.: PCT/GB99/00803

§ 371 Date: Aug. 23, 2000

§ 102(e) Date: Aug. 23, 2000

(87) PCT Pub. No.: WO99/48892

PCT Pub. Date: Sep. 30, 1999

(30) Foreign Application Priority Data

Mar. 20, 1998 (GB) .................................................. 9806102

(51) Int. Cl.[7] ........................ A61K 31/435; C07D 471/04
(52) U.S. Cl. .......................... 514/303; 514/278; 544/127; 544/362; 546/16; 546/87; 546/119; 546/120
(58) Field of Search ..................................... 546/119, 120, 546/16, 87; 514/303; 544/127, 362

(56) References Cited

U.S. PATENT DOCUMENTS 4,479,955  10/1984  Yokoyama .
4,560,689  12/1985  Yokoyama .
4,602,014  7/1986  Yokoyama .

FOREIGN PATENT DOCUMENTS 0 115 469  8/1984  (EP) .
0 126 970  12/1984  (EP) .
0 270 494  6/1988  (EP) .

OTHER PUBLICATIONS

E.E. Kilbourn, et al., J. Org. Chem., 37:1145–1148 (1972).
Y. Oikawa, et al., J. Org. Chem., 43:2087–2088 (1978).
M. Balogh, et al., J. Heterocyclic Chem., 17:359–368 (1980).
E. Diez–Barra, et al., Heterocycles, 38:1367–1374 (1994).
J. Ahman, et al., Synth. Commun., 24:1117–1120 (1994).

*Primary Examiner*—Bernard Dentz
(74) *Attorney, Agent, or Firm*—Shu M. Lee

(57) ABSTRACT

Pyrazolo[4,3-c]pyridin-3-one derivatives substituted at the 2-position by an optionally substituted aryl or heteroaryl moiety, and having pendant substituents at the 7-position and optionally also at the 6-position, are selective ligands for $GABA_A$ receptors, particularly having high affinity for the α2 and/or α3 subunit, and are useful in the treatment and/or prevention of disorders of the central nervous system, including anxiety and convulsions.

10 Claims, No Drawings

PYRAZOLO-PYRIDINE DERIVATIVES AS LIGANDS FOR GABA RECEPTORS

This is an application under 35 U.S.C. 371 of PCT/GB99/00803 and claims priority from Great Britain Application No. 9806102.1 filed Mar. 20, 1998.

The present invention relates to a class of substituted pyrazolo-pyridine derivatives, and to their use in therapy. More particularly, this invention is concerned with substituted pyrazolo[4,3-c]pyridin-3-one analogues which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

U.S. Pat. No. 4,602,014 relates to a family of substituted pyrazolo[3,4-d]pyridin-3-one derivatives wherein the pyridine ring thereof is fused inter alia to an alkylene chain. These compounds are stated therein to be benzodiazepine receptor ligands having nervous system regulatory activity, including anxiomodulating activity. However, there is no disclosure nor any suggestion anywhere in U.S. Pat. No. 4,602,014 of the particular substituted pyrazolo[4,3-c] pyridin-3-one analogues in accordance with the present invention.

The present invention provides a class of substituted pyrazolo-pyridine analogues which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity (K$_{1.1}$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

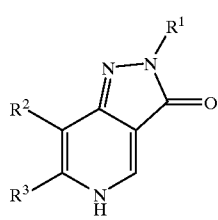

(I)

wherein

R$^1$ represents aryl or heteroaryl, either of which groups may be optionally substituted;

R$^2$ represents halogen; or C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{2-6}$ alkoxycarbonyl, C$_{1-6}$ alkylaminocarbonyl or heteroarylaminocarbonyl, any of which groups may be optionally substituted; and R$^3$ represents hydrogen, C$_{1-6}$ alkyl or trifluoromethyl.

The groups R$^1$ and/or R$^2$ may be unsubstituted or independently substituted by one or more, preferably one or two, substituents. Examples of optional substituents on these groups include C$_{1-6}$ alkyl, hydroxy(C$_{1-6}$)alkyl, di(C$_{1-6}$)alkylamino(C$_{1-6}$)alkyl, aryl(C$_{1-6}$)alkylamino-(C$_{1-6}$)alkyl, heteroaryl(C$_{1-6}$)alkylamino(C$_{1-6}$)alkyl, C$_{2-6}$ alkenyl, C$_{2-6}$ alkynyl, hydroxy(C$_{2-6}$)alkynyl, di(C$_{1-6}$)alkylamino(C$_{2-6}$) alkynyl, C$_{3-7}$ cycloalkyl, aryl, aryl(C$_{1-6}$)alkyl, C$_{3-7}$ heterocycloalkyl, oxo(C$_{3-7}$)heterocycloalkyl, C$_{1-6}$ alkyl (C$_{3-7}$) heterocycloalkyl, C$_{2-6}$ alkoxycarbonyl(C$_{3-7}$) heterocycloalkyl, C$_{3-7}$ heterocycloalkyl(C$_{1-6}$)alkyl, C$_{3-7}$ heterocycloalkylcarbonyl, C$_{1-6}$ alkyl(C$_{3-7}$) heterocycloalkylcarbonyl, spiroheterocyclyl, heteroaryl, C$_{1-6}$ alkylheteroaryl, C$_{3-7}$ heterocycloalkyl(C$_{1-6}$)alkylheteroaryl, C$_{1-6}$ alkyl(C$_{3-7}$)heterocycloalkyl(C$_{1-6}$)alkylheteroaryl, heteroaryl(C$_{1-6}$)alkyl, heteroaryl(C$_{2-6}$)alkynyl, hydroxy, C$_{1-6}$ alkoxy, arylcarbonyloxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, C$_{2-6}$ alkylcarbonylamino, C$_{1-6}$ alkylsulphonylamino, C$_{3-7}$ cycloalkyl(C$_{1-6}$)alkylamino, di[(C$_{3-7}$)cycloalkyl(C$_{1-6}$)alkyl]amino, heteroaryl(C$_{1-6}$) alkylamino, C$_{1-6}$ alkylheteroaryl(C$_{1-6}$)alkylamino, C$_{1-6}$ alkylaminocarbonylamino, amino(C$_{1-6}$) alkylcarbonylamino, C$_{2-6}$ alkoxycarbonylamino(C$_{1-6}$) alkylcarbonylamino, C$_{2-6}$ alkylcarbonyl, heteroaryl(C$_{1-6}$) alkylcarbonyl, C$_{2-6}$ alkoxycarbonyl, aminocarbonyl, halogen, cyano, nitro and trifluoromethyl.

Particular optional substituents on the groups R$^1$ and/or R$^2$ include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, oxo (C$_{3-7}$)heterocycloalkyl, C$_{1-6}$ alkyl(C$_{3-7}$)heterocycloalkyl, C$_{2-6}$ alkoxycarbonyl(C$_{3-7}$)heterocycloalkyl, C$_{3-7}$ heterocycloalkylcarbonyl, C$_{1-6}$ alkyl(C$_{3-7}$) heterocycloalkylcarbonyl, heteroaryl, heteroaryl(C$_{1-6}$)alkyl, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$) alkylamino, C$_{2-6}$ alkylcarbonylamino, C$_{1-6}$ alkylsulphonylamino, heteroaryl(C$_{1-6}$)alkylamino, C$_{1-6}$ alkylaminocarbonylamino, amino(C$_{1-6}$) alkylcarbonylamino, C$_{2-6}$ alkoxycarbonylamino-(C$_{1-6}$) alkylcarbonylamino, C$_{2-6}$ alkylcarbonyl, C$_{2-6}$ alkoxycarbonyl, halogen, nitro and trifluoromethyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylthio", "C$_{1-6}$ alkylsulphonyl" and "C$_{1-6}$ alkylamino" are to be construed accordingly.

The expression "C$_{2-6}$ alkenyl" as used herein refers to straight-chained and branched alkenyl groups containing from 2 to 6 carbon atoms. Typical examples include vinyl, allyl and dimethylallyl groups.

The expression "C$_{2-6}$ alkynyl" as used herein refers to straight-chained and branched alkynyl groups containing from 2 to 6 carbon atoms. Typical examples include ethynyl and propargyl groups.

Particular C$_{3-7}$ cycloalkyl groups include cyclopropyl and cyclohexyl.

Particular aryl groups include phenyl and naphthyl.

Particular aryl(C$_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl groups.

A typical spiroheterocyclyl group is 1-oxa-8-azaspiro [4.5]dec-3-en-3-yl.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, 2,3,4,9-tetrahydro-1H-pyrido[3,4-b]indolyl, pyrazolyl, indazolyl, oxazolyl, isoxazolyl, thiazolyl, isothiazolyl, imidazolyl, benzimidazolyl, azabenzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, imidazolylpropyl, oxadiazolylmethyl, oxadiazolylethyl, oxadiazolylpropyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, the group $R^1$ represents phenyl or pyridinyl, especially phenyl, either unsubstituted or substituted by one or more optional substituents selected typically from $C_{1-6}$ alkyl, $C_{1-6}$ alkoxy and halogen.

Particular values of $R^1$ include phenyl, methylphenyl, methoxyphenyl, fluorophenyl and chlorophenyl, especially chlorophenyl.

Suitably, the group $R^2$ represents halogen; or $C_{1-6}$ alkyl, $C_{2-6}$ alkenyl, $C_{2-6}$ alkynyl, aryl, aryl($C_{1-6}$)alkyl, heteroaryl, heteroaryl($C_{1-6}$)alkyl, $C_{2-6}$ alkoxycarbonyl, $C_{1-6}$ alkylaminocarbonyl or heteroarylaminocarbonyl, any of which groups may be unsubstituted, or substituted by one or more, suitably by one or two, substituents.

More particularly, the group $R^2$ may represent $C_{1-6}$ alkyl, aryl, aryl($C_{1-6}$)alkyl, heteroaryl, $C_{2-6}$ alkoxycarbonyl, $C_{1-6}$ alkylaminocarbonyl or heteroarylaminocarbonyl, any of which groups may be optionally substituted by one or more, suitably by one or two, substituents. Preferably, the group $R^2$ is unsubstituted or monosubstituted.

Appropriately, the group $R^2$ may represent bromo or iodo; or methyl, ethyl, n-propyl, isobutyl, vinyl, propynyl, phenyl, benzyl, pyridinyl, thienyl, indolyl, 2,3,4,9-tetrahydro-1H-pyrido[3,4-b]indolyl, benzimidazolyl, imidazolylpropyl, oxadiazolylpropyl, pyridinylethyl, ethoxycarbonyl, propylaminocarbonyl or thiazolylaminocarbonyl, any of which groups may be optionally substituted.

Typical values of $R^2$ include optionally substituted n-propyl, phenyl, benzyl, pyridinyl, thienyl, ethoxycarbonyl, propylaminocarbonyl and thiazolylaminocarbonyl groups.

Examples of representative substituents on the group $R^2$ include methyl, ethyl, hydroxymethyl, dimethylaminomethyl, benzylaminomethyl, pyridinylmethyl-aminomethyl, hydroxypropynyl, dimethylamino-propynyl, piperidinyl, piperazinyl, morpholinyl, pyrrolidinonyl, methyl-piperazinyl, tert-butoxycarbonyl-piperazinyl, pyrrolidinylmethyl, pyrrolidinylcarbonyl, methyl-piperazinylcarbonyl, 1-oxa-8-azaspiro [4.5]dec-3-en-3-yl, pyridinyl, thienyl, thiazolyl, imidazolyl, azabenzimidazolyl, oxadiazolyl, triazolyl, methyl-imidazolyl, morpholinylmethyl-triazolyl, methylpiperazinylmethyl-triazolyl, pyridinylethyl, pyridinylethynyl, hydroxy, methoxy, benzoyloxy, amino, dimethylamino, acetylamino, methylsulphonylamino, cyclopropylmethylamino, di(cyclopropylmethyl)amino, pyridinylmethylamino, methyltriazolylmethylamino, ethylaminocarbonylamino, 2-amino-2-methylpropionamido, tert-butoxycarbonylaminomethyl-carbonylamino, acetyl, imidazolylmethylcarbonyl, triazolylmethylcarbonyl, methoxycarbonyl, ethoxycarbonyl, aminocarbonyl, chloro, iodo, cyano and nitro.

Examples of typical substituents on the group $R^2$ include piperazinyl, morpholinyl, pyrrolidinonyl, methyl-piperazinyl, tert-butoxycarbonyl-piperazinyl, pyrrolidinylcarbonyl, methyl-piperazinylcarbonyl, pyridinyl, thienyl, imidazolyl, oxadiazolyl, triazolyl, methoxy, amino, dimethylamino, acetylamino, methylsulphonylamino, pyridinylmethylamino, ethylaminocarbonylamino, 2-amino-2-methylpropionamido, tert-butoxycarbonylaminomethyl-carbonylamino, chloro, iodo and nitro.

Illustrative values of $R^2$ include bromo, iodo, hydroxymethyl, methyltriazolylmethylaminomethyl, imidazolylmethylcarbonylmethyl, ethyl, piperidinylethyl, aminocarbonylethyl, n-propyl, hydroxypropyl, benzoyloxypropyl, methoxycarbonylpropyl, aminocarbonylpropyl, cyanopropyl, isobutyl, imidazolylethenyl, pyridinylethenyl, ethoxycarbonylethenyl, aminocarbonylethenyl, morpholinyl-propynyl, dimethylamino-propynyl, phenyl, hydroxymethyl-phenyl, benzylaminomethyl-phenyl, pyridinylmethylaminomethyl-phenyl, hydroxypropynyl-phenyl, dimethylaminopropynyl-phenyl, piperazinyl-phenyl, morpholinyl-phenyl, pyrrolidinonyl-phenyl, methylpiperazinyl-phenyl, tert-butoxycarbonylpiperazinyl-phenyl, pyrrolidinylmethyl-phenyl, pyrrolidinylcarbonyl-phenyl, methylpiperazinylcarbonyl-phenyl, 1-oxa-8-azaspiro [4.5]dec-3-en-3-ylphenyl, pyridinyl-phenyl, thienyl-phenyl, thiazolyl-phenyl, imidazolyl-phenyl, azabenzimidazolyl-phenyl, oxadiazolyl-phenyl, triazolyl-phenyl, methylimidazolyl-phenyl, morpholinylmethyl-triazolylphenyl, methylpiperazinylmethyl-triazolylphenyl, pyridinylethyl-phenyl, pyridinylethynyl-phenyl, hydroxyphenyl, methoxyphenyl, aminophenyl, dimethylamino-phenyl, acetylamino-phenyl, methylsulphonylamino-phenyl, N-(cyclopropylmethyl)aminophenyl, N,N-di(cyclopropylmethyl)aminophenyl, pyridinylmethyl-aminophenyl, ethylaminocarbonylaminophenyl, 2-amino-2-methyl-propionamidophenyl, tert-butoxycarbonyl-aminomethylcarbonylaminophenyl, methoxycarbonyl-phenyl, aminocarbonyl-phenyl, chlorophenyl, iodophenyl, cyanophenyl, nitrophenyl, benzyl, pyridinyl, thienyl, dimethylaminomethyl -indolyl, 2-ethyl-2,3,4,9-tetrahydro-1H-pyrido[3,4-b]indol-6-yl, 2-acetyl-2,3,4,9-tetrahydro-1H-pyrido[3,4-b]indol-6-yl, benzimidazolyl, imidazolylpropyl, methyloxadiazolylpropyl, pyridinylmethyl, ethoxycarbonyl, propylaminocarbonyl and thiazolylaminocarbonyl.

Particular values of $R^2$ include propyl, phenyl, piperazinyl-phenyl, morpholinyl-phenyl, pyrrolidinonyl-phenyl, methylpiperazinyl-phenyl, tert-butoxycarbonylpiperazinyl-phenyl, pyrrolidinylcarbonyl-phenyl, methylpiperazinylcarbonyl-phenyl, pyridinyl-phenyl, thienyl-phenyl, imidazolyl-phenyl, oxadiazolyl-phenyl, triazolyl-phenyl, methoxyphenyl, aminophenyl, dimethylamino-phenyl, acetylamino-phenyl, methylsulphonylamino-phenyl, pyridinylmethyl-aminophenyl, ethylaminocarbonylamino-phenyl, 2-amino-2-methyl-propionamidophenyl, tert-butoxycarbonyl-aminomethylcarbonylaminophenyl, chlorophenyl, iodophenyl, nitrophenyl, benzyl, pyridinyl, thienyl, ethoxycarbonyl, propylaminocarbonyl and thiazolylami-nocarbonyl.

Particular values of $R^3$ include hydrogen, methyl and ethyl, especially methyl.

A particular sub-class of compounds according to the invention is represented by the compounds of formula II, and salts and prodrugs thereof:

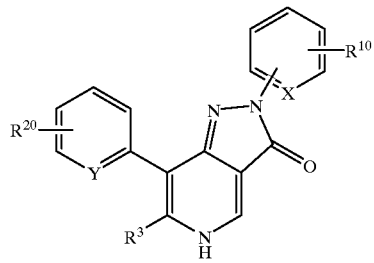

(II)

wherein $R^3$ is as defined above with reference to formula I;

X and Y independently represent CH or nitrogen;

$R^{10}$ represents hydrogen, $C_{1-6}$ alkyl, $C_{1-6}$ alkoxy, $C_{1-6}$ alkylsulphonyl, $C_{2-6}$ alkylcarbonyl, halogen, cyano or trifluoromethyl; and $R^{20}$ represents hydroxy($C_{1-6}$)alkyl, aryl($C_{1-6}$)alkylamino ($C_{1-6}$)alkyl, heteroaryl($C_{1-6}$)alkylamino($C_{1-6}$)alkyl, hydroxy($C_{1-6}$)alkynyl, di($C_{1-6}$)alkylamino($C_{2-6}$) alkynyl, $C_{3-7}$ heterocycloalkyl, oxo($C_{3-7}$) heterocycloalkyl, $C_{1-6}$ alkyl($C_{3-7}$)heterocycloalkyl, $C_{2-6}$ alkoxycarbonyl($C_{3-7}$)heterocycloalkyl, $C_{3-7}$ heterocycloalkyl($C_{1-6}$)alkyl, $C_{3-7}$ heterocycloalkylcarbonyl, $C_{1-6}$ alkyl($C_{3-7}$) heterocycloalkylcarbonyl, spiroheterocyclyl, heteroaryl, $C_{1-6}$ alkylheteroaryl, $C_{3-7}$ heterocycloalkyl-($C_{1-6}$)alkylheteroaryl, $C_{1-6}$ alkyl($C_{3-7}$)heterocycloalkyl ($C_{1-6}$)alkylheteroaryl, heteroaryl($C_{1-6}$)alkyl, heteroaryl ($C_{2-6}$)alkynyl, hydroxy, $C_{1-6}$ alkoxy, amino, di($C_{1-6}$) alkylamino, $C_{2-6}$ alkylcarbonylamino, $C_{1-6}$ alkylsulphonylamino, $C_{3-7}$ cycloalkyl($C_{1-6}$) alkylamino, di[($C_{3-7}$)cycloalkyl($C_{1-6}$)alkyl]amino, heteroaryl($C_{1-6}$)alkylamino, $C_{1-6}$ alkylaminocarbonylamino, amino($C_{1-6}$) alkylcarbonylamino, $C_{1-6}$ alkoxycarbonylamino-($C_{1-6}$) alkylcarbonylamino, $C_{1-6}$ alkoxycarbonyl, aminocarbonyl, halogen, cyano or nitro.

The present invention also provides a compound of formula II as depicted above, or a salt or prodrug thereof, wherein $R^3$, X, Y and $R^{10}$ are as defined above; and $R^{20}$ represents $C_{3-7}$ heterocycloalkyl, oxo($C_{3-7}$) heterocycloalkyl, $C_{1-6}$ alkyl($C_{3-7}$)heterocycloalkyl, $C_{2-6}$ alkoxycarbonyl($C_{3-7}$)heterocycloalkyl, $C_{3-7}$ heterocycloalkylcarbonyl, $C_{1-6}$ alkyl($C_{3-7}$) heterocycloalkylcarbonyl, heteroaryl, $C_{1-6}$ alkoxy, amino, di($C_{1-6}$)alkylamino, $C_{2-6}$ alkylcarbonylamino, $C_{1-6}$ alkylsulphonylamino, heteroaryl($C_{1-6}$)alkylamino, $C_{1-6}$ alkylaminocarbonylamino, amino($C_{1-6}$) alkylcarbonylamino, $C_{1-6}$ alkoxycarbonylamino-($C_{1-6}$) alkylcarbonylamino, halogen or nitro.

Suitably, X is CH.

Suitably, Y is CH.

Suitably, $R^{10}$ represents hydrogen, $C_{1-6}$ alkyl, $C_{1-6}$ alkoxy or halogen. Particular values of $R^{10}$ include hydrogen, methyl, methoxy, fluoro and chloro, especially chloro.

Representative values of $R^{20}$ include hydroxymethyl, benzylaminomethyl, pyridinylmethylaminomethyl, hydroxypropynyl, dimethylaminopropynyl, piperazinyl, morpholinyl, pyrrolidinonyl, methyl-piperazinyl, tert-butoxycarbonyl-piperazinyl, pyrrolidinylmethyl, pyrrolidinylcarbonyl, methyl-piperazinylcarbonyl, 1-oxa-8-azaspiro[4.5]dec-3-en-3-yl, pyridinyl, thienyl, thiazolyl, imidazolyl, azabenzimidazolyl, oxadiazolyl, triazolyl, methylimidazolyl, morpholinylmethyl-triazolyl, methylpiperazinylmethyl-triazolyl, pyridinylethyl, pyridinylethynyl, hydroxy, methoxy, amino, dimethylamino, acetylamino, methylsulphonylamino, cyclopropylmethyl-amino, di(cyclopropylmethyl)amino, pyridinylmethylamino, ethylaminocarbonylamino, 2-amino-2-methylpropionamido, tert-butoxycarbonylaminomethyl-carbonylamino, methoxycarbonyl, aminocarbonyl, chloro, iodo, cyano and nitro.

Particular values of $R^{20}$ include piperazinyl, morpholinyl, pyrrolidinonyl, methyl-piperazinyl, tert-butoxycarbonyl-piperazinyl, pyrrolidinylcarbonyl, methyl-piperazinylcarbonyl, pyridinyl, thienyl, imidazolyl, oxadiazolyl, triazolyl, methoxy, amino, dimethylamino, acetylamino, methylsulphonylamino, pyridinylmethylamino, ethylaminocarbonylamino, 2-amino-2-methylpropionamido, tert-butoxycarbonylaminomethyl-carbonylamino, chloro, iodo and nitro.

Specific compounds within the scope of the present invention include:

2,5-dihydro-2,7-diphenylpyrazolo[4,3-c]pyridin-3-one;

2,5-dihydro-2-phenyl-7-propylpyrazolo[4,3-c]pyridin-3-one;

2,5-dihydro-2-(4-methoxyphenyl)-7-propylpyrazolo[4,y3-c]pyridin-3-one;

2-(4-chlorophenyl)-2,5-dihydro-7-propylpyrazolo[4,3-c]pyridin-3-one;

7-benzyl-2-(4-chlorophenyl)-2,5-dihydropyrazolo[4,3-c]pyridin-3-one;

7-benzyl-2,5-dihydro-2-(4-methoxyphenyl)pyrazolo[4,3-c]pyridin-3-one;

3,5-dihydro-3-oxo-2-phenyl-2H-pyrazolo[4,3-c]pyridine-7-carboxylic acid propylamide;

3,5-dihydro-3-oxo-2-phenyl-2H-pyrazolo[4,3-c]pyridine-7-carboxylic acid thiazol-2-ylamide;

2-(4-chlorophenyl)-2,5-dihydro-6-methyl-7-phenylpyrazolo[4,3-c]pyridin-3-one;

2,5-dihydro-2-(4-methoxyphenyl)-6-methyl-7-phenylpyrazolo[4,3-c]pryidin-3-one;

2,5-dihydro-6-methyl-2,7-diphenylpyrazolo[4,3-c]pyridin-3-one;

2,5-dihydro-6-methyl-2-(4-methylphenyl)-7-phenylpyrazolo[4,3-c]pyridin-3-one;

2-(4-fluorophenyl)-2,5-dihydro-6-methyl-7-phenylpyrazolo[4,3-c]pryidin-3-one;

6-ethyl-2,5-dihydro-2-(4-methoxyphenyl)-7-phenylpyrazolo[4,3-c]pyridin-3-one;

6-ethyl-2,5-dihydro-2,7-diphenylpyrazolo[4,3-c]pyridin-3-one;

2,5-dihydro-2,7-bis(4-methoxyphenyl)-6-methylpyrazolo[4,3-c]pyridin-3-one;

2-(4-chlorophenyl)-2,5-dihydro-7-(4-methoxyphenyl)-6-methyl-pyrazolo[4,3-c]pyridin-3-one;

2,7-bis(4-chlorophenyl)-2,5-dihydro-6-methylpyrazolo[4,3-c]pyridin-3-one;

2-(4-chlorophenyl)-2,5-dihydro-7-(3-methoxyphenyl)-6-methyl-pyrazolo[4,3-c]pyridin-3-one;

2-(4-chlorophenyl)-2,5-dihydro-7-(2-methoxyphenyl)-6-methyl-pyrazolo[4,3-c]pyridin-3-one;

2-(4-chlorophenyl)-2,5-dihydro-6-methyl-7-(thiophen-2-yl)pyrazolo[4,3-c]pryidin-3-one;

2-(4-chlorophenyl)-2,5-dihydro-7-(3-iodophenyl)-6-methylpyrazolo[4,3-c]pyridin-3-one;

2-(4-chlorophenyl)-2,5-dihydro-6-methyl-7-[3-(pyridin-3-yl)phenyl]-pyrazolo[4,3-c]pyridin-3-one;

2-(4-chlorophenyl)-2,5-dihydro-6-methyl-7-[3-(thiophen-2-yl)phenyl]-pyrazolo[4,3-c]pyridin-3-one;

2-(4-chlorophenyl)-2,5-dihydro-6-methyl-7-[3-(3-methyl-1,2,4-oxadiazol-5-yl)phenyl]pyrazolo[4,3-c]pyridin-3-one;

2-(4-chlorophenyl)-2,5-dihydro-6-methyl-7-[3-(pyrrolidin-1-ylcarbonyl)phenyl]pyrazolo[4,3-c]pyridin-3-one;

2-(4-chlorophenyl)-2,5-dihydro-6-methyl-7-[3-(4-methylpiperazin-1-ylcarbonyl)phenyl]pyrazolo[4,3-c]pyridin-3-one;

2-(4-chlorophenyl)-2,5-dihydro-6-methyl-7-[3-(imidazol-1-yl)phenyl]-pyrazolo[4,3-c]pyridin-3-one;

2-(4-chlorophenyl)-2,5-dihydro-6-methyl-7-[4-(pyridin-3-yl)phenyl]-pyrazolo[4,3-c]pryidin-3-one;

2-(4-chlorophenyl)-2,5-dihydro-6-methyl-7-[4-(morpholin-4-yl)phenyl]-pyrazolo[4,3-c]pyridin-3-one;

2-(4-chlorophenyl)-2,5-dihydro-6-methyl-7-[3-nitrophenyl]pyrazolo[4,3-c]pryidin-3-one;

7-(3-aminophenyl)-2-(4-chlorophenyl)-2,5-dihydro-6-methylpyrazolo[4,3-c]pyridin-3-one;

2-(4-chlorophenyl)-2,5-dilhydro-6-methyl-7-[3-(3-pyrdylmethylamino)phenyl]pyrazolo[4,3-c]pyridin-3-one;

2-(4-chlorophenyl)-2,5-dihydro-6-methyl-7-[3-(dimethylamino)phenyl]-pyrazolo[4,3-c]pyridin-3-one;

N-{3-[2-(4-chlorophenyl)-3,5-dihydro-6-methyl-3-oxo-2H-pyrazolo[4,3-c]pyridin-7-yl]phenyl}methanesulphonamide;

2-(4-chlorophenyl)-2,5-dihydro-6-methyl-7-[3-(4H-1,2,4-triazol-4-yl)phenyl]pyrazolo[4,3-c]pryidin-3-one;

N-{3-[2-(4-chlorophenyl)-3,5-dihydro-6-methyl-3-oxo-2H-pyrazolo[4,3-c]pryidin-7-yl]phenyl}-N'(ethyl)urea;

2-(4- chlorophenyl) -2,5- dihydro-6-methyl-7-[3-(4-methylpiperazin-1-yl)phenyl]pyrazolo[4,3-c]pyridin-3-one;

2,5-dihydro-2-phenyl-7-(4-pyridyl)pyrazolo[4,3-c]pyridin-3-one;

7-(4-aminophenyl)-2-(4-chlorophenyl)-2,5-dihydro-6-methylpyrazolo[4,3-c]pyridin-3-one;

7-(4-acetamidophenyl)-2-(4-chlorophenyl)-2,5-dihydro-6-methyl-pyrazolo[4,3-c]pyridin-3-one;

7-[4-(4-(4-(tert-butoxycarbonyl)piperazin-1-yl)phenyl]-2-(4-chlorophenyl)-2,5-dihydro-6-methylpyrazolo[4,3-c]pyridin-3-one;

2-(4-chlorophenyl)-2,5-dihydro-6-methyl-7-[4-(piperazin-1-yl)phenyl]-pyrazolo[4,3-c]pyridin-3-one;

2-(4-chlorophenyl)-2,5-dihydro-6-methyl-7-[4-(pyrrolidin-2-on-1-yl)phenyl]pyrazolo[4,3-c]pryidin-3-one;

7-[4-(2-amino-2-methylpropionamido)phenyl]-2-(4-chlorophenyl)-2,5-dihydro-6-methylpyrazolo[4,3-c]pyridin-3-one;

2-(4-chlorophenyl)-2,5-dihydro-6-methyl-7-[4-(4-methylpiperazin-1-yl)phenyl]pyrazolo[4,3-c]pyridin-3-one;

7-[4-(N'-tert-butoxycarbonylglycinamido)phenyl]-2-(4-chlorophenyl)-2,5-dihydro-6-methylpyrazolo[4,3-c]pryidin-3-one;

2-(4-chlorophenyl)-2,5-dihydro-6-methyl-7-[4-(1,2,4-triazol-4-yl)phenyl]-pyrazolo[4,3-c]pyridin-3-one;

2-(4-chlorophenyl)-7-(4-cyanophenyl)-2,5-dihydro-6-methylpyrazolo[4,3-c]pyridin-3-one;

7-(3-cyanophenyl)-2-(4-chlorophenyl)-2,5-dihydro-6-methylpyrazolo[4,3-c]pyridin-3-one;

2-(4-chlorophenyl)-2,5-dihydro-6-methyl-7-[4-(pyridin-2-ylmethylamino)-phenyl]pyrazolo[4,3-c]pryidin-3-one;

2-(4-chlorophenyl)-7-[4-(N,N-di(cyclopropylmethyl)amino)phenyl]-2,5-dihydro-6-methylpyrazolo[4,3-c]pryidin-3-one;

2-(4-chlorophenyl)-7-[4-(N-cyclopropylmethylamino)phenyl]-2,5-dihydro-6-methylpyrazolo[4,3-c]pyridin-3-one;

7-(4-carboxamidophenyl)-2-(4-chlorophenyl)-2,5-dihydro-6-methyl-pyrazolo[4,3-c]pyridin-3-one;

2-(4-chlorophenyl)-2,5-dihydro-7-(3-methoxycarbonylphenyl)-6-methyl-pyrazolo[4,3-c]pyridin-3-one;

2-(4-chlorophenyl)-2,5-dihydro-6-methyl-7-[3-(pyridin-2-ylmethylaminomethyl)phenyl]pyrazolo[4,3-c]pyridin-3-one;

2-(4-chlorophenyl)-2,5-dihydro-6-methyl-7-[4-(pyridin-2-ylmethylaminomethyl)phenyl]pyrazolo[4,3-c]pyridin-3-one;

7-[4-(benzylaminomethyl)phenyl]-2-(4-chlorophenyl)-2,5-dihydro-6-methyl-pyrazolo[4,3-c]pyridin-3-one;

7-(3-carboxamidophenyl)-2-(4-chlorophenyl)-2,5-dihydro-6-methyl-pyrazolo[4,3-c]pyridin-3-one;

2-(4-chlorophenyl)-2,5-dihydro-6-methyl-7-[4-(pyrrolidin-1-ylmethyl)phenyl]-pyrazolo[4,3-c]pryidin-3-one;

2-(4-chlorophenyl)-2,5-dihydro-7-[4-(hydroxymethyl)phenyl]-6-methyl-pyrazolo[4,3-c]pyridin-3-one;

2-(4-chlorophenyl)-2,5-dihydro-7-(4-iodophenyl)-6-methylpyrazolo[4,3-c]pyridin-3-one;

2-(4-chlorophenyl)-2,5-dihydro-6-methyl-7-[4-(3-dimethylaminoprop-1-yn-1-yl)phenyl]pyrazolo[4,3-c]pyridin-3-one;

2-(4-chlorophenyl)-2,5-dihydro-7-[4-(imidazol-1-yl)phenyl]-6-methyl-pyrazolo[4,3-c]pyridin-3-one;

2-(4-chlorophenyl)-2,5-dihydro-7-[4-(imidazol-2-yl)phenyl]-6-methyl-pyrazolo[4,3-c]pyridin-3-one;

2-(4-chlorophenyl)-2,5-dihydro-6-methyl-7-[4-(1,2,3-triazol-5-yl)phenyl3-pyrazolo[4,3-c]pyridin-3-one;

2-(4-chlorophenyl)-2,5-dihydro-6-methyl-7-[4-(thiazol-2-yl)phenyl]-pyrazolo[4,3-c]pyridin-3-one;

2-(4-chlorophenyl)-2,5-dihydro-7-(4-hydroxyphenyl)-6-methylpyrazolo[4,3-c]pyridin-3-one;

2-(4-chlorophenyl)-2,5-dihydro-7-[4-(3-hydroxyprop-1-yn-1-yl)phenyl]-6-methylpyrazolo[4,3-c]pyridin-3-one;

7-[4-(6-azabenzimidazol-2-yl)phenyl]-2-(4-chlorophenyl)-2,5-dihydro -6-methylpyrazolo[4,3-c]pyridin-3-one;

7-(2-acetyl-2,3,4,9-tetrahydro-1H-pyrido[3,4-b]indol-6-yl)-2-(4-chlorophenyl)-2,5-dihydro-6-methylpyrazolo[4,3-c]pyridin-3-one;

2-(4-chlorophenyl)-7-(2-ethyl-2,3,4,9-tetrahydro-1H-pyrido[3,4-b]indol-6-yl)-2,5-dihydro-6-methylpyrazolo[4,3-c]pyridin-3-one;

2-(4-chlorophenyl)-2,5-dihydro-7-[2-(dimethylaminomethyl)indol-5-yl]-6-methylpyrazolo[4,3-c]pyridin-3-one;

7-(benzimidazol-5-yl)-2-(4-chlorophenyl)-2,5-dihydro-6-methylpyrazolo[4,3-c]pryidin-3-one;

2-(4-chlorophenyl)-2,5-dihydro-6-methyl-7-[4-(4-(morpholin-4-ylmethyl)-1,2,3-triazol-5-yl)phenyl]pyrazolo[4,3-c]pyridin-3-one;

2-(4-chlorophenyl)-2,5-dihydro-6-methyl-7-[4-(4-(morpholin-4-methyl)-1,2,3-triazol-5-yl)phenyl]pyrazolo[4,3-c]pyridin-3-one;
2-(4-chlorophenyl)-2,5-dihydro-6-methyl-7-[4-(2-(pyridin-2-yl)eth-1-yn-1-yl)phenyl]pyrazolo[4,3-c]pyridin-3-one;
2-(4-chlorophenyl)-2,5-dihydro-6-methyl-7-[4-(2-(pyridin-2-yl)ethyl)phenyl]pyrazolo[4,3-c]pyridin-3-one;
2-(4-chlorophenyl)-2,5-dihydro-6-methyl-7-[4-(1-methylimidazol-2-yl)phenyl]-pyrazolo[4,3-c]pyridin-3-one;
2-(4-chlorophenyl)-2,5-dihydro-6-methyl-7-[4-(1,2,4-triazol-3-yl)phenyl]-pyrazolo[4,3-c]pyridin-3-one;
2-(4-chlorophenyl)-2,5-dihydro-6-methyl-7-[4-(1-oxa-8-azaspiro[4.5]dec-3-en-3-yl)phenyl]pyrazolo[4,3-c]pyridin-3-one;
7-bromo-2-(4-chlorophenyl)-2,5-dihydro-6-methylpyrazolo[4,3-c]pyridin-3-one;
2-(4-chlorophenyl)-2,5-dihydro-7-iodo-6-methylpyrazolo[4,3-c]pyridin-3-one;
2-(4-chlorophenyl)-2,5-dihydro-7-(2-ethoxycarbonylethenyl)-6-methyl-pyrazolo[4,3-c]pyridin-3-one;
7-(2-carboxamidoethenyl)-2-(4-chlorophenyl)-2,5-dihydro-6-methylpyrazolo[4,3-c]pryidin-3-one;
2-(4-chlorophenyl)-2,5-dihydro-6-methyl-7-[2-(pyridin-4-yl)ethenyl]-pyrazolo[4,3-c]pyridin-3-one;
7-benzyl-2-(4-chlorophenyl)-2,5-dihydro-6-methylpyrazolo[4,3-c]pyridin-3-one;
2-(4-chlorophenyl)-2,5-dihydro-6-methyl-7-[2-(pyridin-4-yl)ethyl]pyrazolo[4,3-c]pyridin-3-one;
7-(2-carboxamidoethyl)-2-(4-chlorophenyl)-2,5-dihydro-6-methylpyrazolo[4,3-c]pyridin-3-one;
2-(4-chlorophenyl)-2,5-dihydro-6-methyl-7-[2-(pyridin-2-yl)ethenyl]-pyrazolo[4,3-c]pryidin-3-one;
2-(4-chlorophenyl)-2,5-dihydro-7-(3-dimethylaminoprop-1-ynyl)-6-methyl-pyrazolo[4,3-c]pyridin-3-one;
2-(4-chlorophenyl)-2,5-dihydro-6-methyl-7-(thien-3-yl)pyrazolo[4,3-c]pyridin-3-one;
2-(4-chlorophenyl)-3,5-dihydro-6-methyl-3-oxo-2H-pyrazolo[4,3-c]pyridine-7-carboxylic acid ethyl ester;
2-(4-chlorophenyl)-2,5-dihydro-7-[2-(imidazol-1-yl)ethenyl]-6-methyl-pyrazolo[4,3-c]pyridin-3-one;
2-(4-chlorophenyl)-2,5-dihydro-7-ethyl-6-methylpyrazolo[4,3-c]pyridin-3-one;
2-(4-chlorophenyl)-2,5-dihydro-7-(2-methylpropyl)-6-methylpyrazolo[4,3-c]pyridin-3-one;
2-(4-chlorophenyl)-2,5-dihydro-6-methyl-7-[2-(pyridin-2-yl)ethyl]pyrazolo[4,3-c]pyridin-3-one;
2-(4-chlorophenyl)-2,5-dihydro-6-methyl-7-[2-(piperidin-2-yl)ethyl]-pyrazolo[4,3-c]pyridin-3-one;
2-(4-chlorophenyl)-2,5-dihydro-6-methyl-7-[3-(morpholin-4-yl)prop-1-ynyl]-pyrazolo[4,3-c]pyridin-3-one;
2-(4-chlorophenyl)-2,5-dihydro-7-hydroxymethyl-6-methylpyrazolo[4,3-c]pyridin-3-one;
2-(4-chlorophenyl)-2,5-dihydro-6-methyl-7-[2-oxo-3-(1,2,4-triazol-1-yl)propyl]-pyrazolo[4,3-c]pyridin-3-one;
2-(4-chlorophenyl)-2,5-dihydro-7-[3-(imidazol-1-yl)-2-oxopropyl]-6-methyl-pyrazolo[4,3-c]pyridin-3-one;
2-(4-chlorophenyl)-2,5-dihydro-6-methyl-7-[N-(2-methyl-2H-1,2,4-triazol-3-ylmethyl)aminomethyl]pyrazolo[4,3-c]pyridin-3-one;
2-(4-chlorophenyl)-2,5-dihydro-7-(3-methoxycarbonylpropyl)-6-methylpyrazolo[4,3-c]pyridin-3-one;
7-(3-carboxamidopropyl)-2-(4-chlorophenyl)-2,5-dihydro-6-methylpyrazolo[4,3-c]pyridin-3-one;
7-(3-benzoyloxypropyl)-2-(4-chlorophenyl)-2,5-dihydro-6-methylpyrazolo[4,3-c]pyridin-3-one;
2-(4-chlorophenyl)-2,5-dihydro-6-methyl-7-[3-(3-methyl-1,2,4-oxadiazol-5-yl)propyl]pyrazolo[4,3-c]pyridin-3-one;
2-(4-chlorophenyl)-7-(3-cyanopropyl)-2,5-dihydro-6-methylpyrazolo[4,3-c]pyridin-3-one;
2-(4-chlorophenyl)-2,5-dihydro-6-methyl-7-(pyridin-3-yl)pyrazolo[4,3-c]pyridin-3-one;
2-(4-chlorophenyl)-2,5-dihydro-7-[3-(1H-imidazol-2-yl)propyl]-6-methyl-pyrazolo[4,3-c]pyridin-3-one;
2-(4-chlorophenyl)-2,5-dihydro-7-(3-hydroxypropyl)-6-methylpyrazolo[4,3-c]pyridin-3-one;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a hydrazine derivative of formula IV, or an acid addition salt thereof:

(III)

[Structure: pyridine ring with L at 4-position, Z at 3-position, R² at 5-position, R³ at 6-position, N at 1-position]

(IV)

R¹—NHNH₂ wherein $R^1$, $R^2$ and $R^3$ are as defined above, L represents a readily displaceable group, and Z represents a reactive carboxylate moiety.

The acid addition salt of the hydrazine derivative of formula IV is suitably a mineral acid addition salt, typically the hydrochloride salt.

The readily displaceable group L in the compound of formula III is suitably a halogen atom, e.g. chloro.

Suitable values for the reactive carboxylate moiety Z include esters, for example $C_{1-4}$ alkyl esters; acid anhydrides, including mixed anhydrides with $C_{1-4}$ alkanoic acids; acid halides, for example acid chlorides; and acylimidazoles. Typically, Z represents methoxycarbonyl or ethoxycarbonyl.

The reaction between compounds III and IV may conveniently be carried out by heating the reactants in a suitable solvent, e.g. a lower alkanol such as n-butanol or ethanol, typically at the reflux temperature.

A typical intermediate of formula III wherein the readily displaceable group L is chloro may conveniently be prepared by treating the compound of formula V:

(V)

[Structure: 4-pyridinone with Z at 3-position, R² at 5-position, R³ at 6-position, NH]

wherein $R^2$, $R^3$ and Z are as defined above; with phosphorus oxychloride.

Where they are not commercially available, the starting materials of formula IV and V may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art, including the methods described in the accompanying Examples.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk cells.

Reagents

Phosphate buffered saline (PBS).

Assay buffer: 10 mM $KH_2PO_4$, 100 mM KCl pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells Assay Can be carried out in deep 96-well plates or in tubes. Each tube contains:

300 pl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [3H]-flumazenil from the (α2 and/or α3 subunit of the human $GABA_A$ receptor of 100 nM or less.

EXAMPLE 1

2,5-Dihydro-2,7-diphenylyrazolo[4,3-c]pyridin-3-one a) Ethyl 4-chloro-3-phenyl-5-pyridinecarboxylate A mixture of ethyl 1,4-dihydro-4-oxo-3-phenyl-5-pyridinecarboxylate (prepared from phenylacetyl chloride according to the procedures described in *J. Org. Chem.* 1978, 43, 2087–2088 and *J. Heterocyclic Chem.* 1980, 17, 359–368) (3.82 g, 15.7 mmol) and phosphorus oxychloride (50 ml) was heated at reflux overnight. The excess solvent was removed in vacuo. The residue was partitioned between ice-cold aqueous $Na_2CO_3$ and ethyl acetate, and the organic layer was evaporated in vacuo to afford 3.72 g (90%) of the title compound as a brown solid; $^1$H NMR (250 MHz, $CDCl_3$) δ1.44 (3H, t, J 7.2 Hz), 4.47 (2H, q, J 7.2 Hz), 7.40–7.54 (5H, m), 8.62 (1H, s), 8.91 (1H, s); MS ($ES^+$) m/z 262/264 $[MH]^{30}$.

b) 2,5-Dihydro-2,7-diphenylpyrazolo[4,3-c]pyridin-3-one

A mixture of ethyl 4-chloro-3-phenyl-5-pyridinecarboxylate (0.300 g, 1.15 mmol) and phenylhydrazine (0.125 ml, 1.27 mmol) in 1-butanol (25 ml) was stirred at reflux under nitrogen for 24 h. More phenylhydrazine (0.125 ml, 1.27 mmol) was added and the mixture was stirred at reflux for a further 3 days. The solvent was removed in vacuo and dichloromethane, followed by hydrogen chloride in diethyl ether, was added. The solution was filtered, and the filtrate was washed with aqueous $NaHCO_3$ and evaporated in vacuo to give 31 mg (9%) of the title compound as a yellow solid; mp 280–285° C.; $^1$H NMR (250 MHz, DMSO-$d_6$) δ7.18 (1H, t, J 7.4 Hz), 7.41–7.56 (5H, m), 7.91 (1H, s), 8.17 (2H, d, J 7.1 Hz), 8.22 (2H, d, J 7.5 Hz), 8.58 (1H, s), 12.60 (1H, br s); MS ($ES^+$) m/z 288 $[MH]^+$. Anal. found: C, 70.03; H, 5.00; N, 13.41. $C_{18}H_{12}N_3O.1.3H_2O$ requires: C, 69.80; H, 4.75; N, 13.56%.

EXAMPLE 2

2,5-Dihydro-2-phenyl-7-propylpyrazolo[4,3-c]pyridin-3-one a) Ethyl 4-chloro-3-propyl-5-pyridinecarboxylate A mixture of ethyl 1,4-dihydro-4-oxo-3-propyl-5-pyridinecarboxylate (prepared from 3-oxoenanthic acid, ethyl ester as described in *J. Heterocyclic Chem.* 1980, 17, 359–368) (3.33 g, 15.9 mmol) and phosphorus oxychloride (50 ml) was heated at reflux for 2 h. The excess solvent was removed in vacuo and the residue was azeotroped with toluene. The residue was dissolved in dichloromethane (75 ml) and washed with saturated aqueous $NaHCO_3$ (100 ml). The aqueous layer was further extracted with dichloromethane (2×75 ml), and the combined organic extracts were dried ($Na_2SO_4$) and evaporated in vacuo. The residue was purified by flash chromatography (silica gel, 25% EtOAc/hexane) to yield 2.84 g (78%) of the title compound as a pale yellow oil; $^1$H NMR (250 MHz, $CDCl_3$) δ1.00 (3H, t, J 7.3 Hz), 1.42 (3H, t, J 7.1 Hz), 1.68 (2H, m), 2.77 (2H, m), 4.43 (2H, q, J 7.1 Hz), 8.51 (1H, s), 8.78 (1H, s); MS ($ES^+$) m/z 228/230 $[MH]^+$.

b) 2,5-Dihydro-2-phenyl-7-propylpyrazolo[4,3-c]pryidin-3-one

A mixture of ethyl 4-chloro-3-propyl-5-pyridinecarboxylate (0.5123 g, 2.25 mmol) and phenylhydrazine (0.32 ml, 3.25 mmol) in anhydrous 1-butanol (18 ml) was stirred at reflux under nitrogen for 50 h. The solvent was removed in vacuo and the residue was purified by flash chromatography (silica gel, 5–10% $MeOH/CH_2Cl_2$) to give 0.4767 g (84%) of the title compound as a yellow solid; mp 221–224° C. ($CH_2Cl_2$-EtOAc-hexane); $^1$H NMR (360 MHz, DMSO-$d_6$) δ0.95 (3H, t, J 7.3 Hz), 1.77 (2H, m), 2.63 (2H, t, J 7.3 Hz), 7.15 (1H, t, J 7.4 Hz), 7.36 (1H, s), 7.42 (2H, t, J 7.4 Hz), 8.19 (2H, d, J 7.5 Hz), 8.47 (1H, s), 12.14 (1H, br s); MS ($ES^+$) m/z 254 $[MH]^+$. Anal. found: C, 71.22; H, 5.59; N, 16.45. $C_{15}H_{15}N_3O$ requires: C, 71.13; H, 5.97; N, 16.59%.

EXAMPLE 3

2,5-Dihydro-2-(4-methoxyphenyl)-7propylpyrazolo[4,3-c]pyridin-3-one

Following a similar procedure to that described in Example 2, Step b, except using 4-methoxyphenylhydrazine hydrochloride instead of phenylhydrazine (and degassing the cold mixture by evaporating the flask under vacuum and refilling with nitrogen several times), the title compound was prepared in 32% yield as a yellow solid; mp 165° C. ($CH_2Cl_2$-EtOAc-hexane); $^1$H NMR (360 MHz, DMSO-$d_6$) δ0.94 (3H, t, J 7.4 Hz), 1.76 (2H, m), 2.63 (2H, t, J 7.4 Hz), 3.77 (3H, s), 6.99 (2H, d, J 9.2 Hz), 7.34 (1H, s), 8.07 (2H, d, J 9.2 Hz), 8.44 (1H, s), 12.12 (1H, br s); MS ($ES^+$) m/z 284 $[MH]^+$. Anal. found: C, 66.54; H, 6.12; N, 14.40. $C_{16}H_{17}N_3O_2.0.3H_2O$ requires: C, 66.56; H, 6.14; N, 14.55%.

EXAMPLE 4

2-(4-Chlorophenyl)-2,5-dihydro-7-propylpyrazolo[4,3-c]pyridin-3-one hydrochloride A mixture of ethyl 4-chloro-3-propyl-5-pyridinecarboxylate (0.3199 g, 1.40 mmol) and 4-chlorophenylhydrazine hydrochloride (0.3019 g, 1.69 mmol) in anhydrous 1-butanol (12 ml) was degassed by evaporating the flask under vacuum and refilling with nitrogen several times and then stirred at reflux under nitrogen for 4 h. After leaving to cool overnight, the mixture was filtered, and the solid was washed with ethyl acetate and dried at 60° C. under vacuum to afford 0.2454 g (54%) of the title compound as a yellow solid; mp 213–218° C. ($CH_2Cl_2$-MeOH-EtOAc); $^1$H NMR (360 MHz, DMSO-$d_6$) δ0.94 (3H, t, J 7.4 Hz), 1.76 (2H, m), 2.64 (2H, t, J 7.3 Hz), 7.41 (1H, s), 7.48 (2H, d, J 9.0 Hz), 8.24 (2H, d, J 8.9 Hz), 8.52 (1H, s), 12.36 (1H, br s); MS ($ES^+$) m/z 288/290 $[MH]^+$. Anal. found: C, 56.13; H, 4.64; N, 13.02. $C_{15}H_{14}ClN_3O.0.9HCl$ requires: C, 56.20; H, 4.69; N, 13.11%.

EXAMPLE 5

7-Benzyl-2-(4-chlorophenyl)-2,5dihydropyrazolo[4,3-c]pyridin-3-one hydrochloride a) Ethyl 3-oxo-5-phenylpentanoate To a stirred mixture of isopropylidene malonate (5.00 g, 34.7 mmol) in anhydrous dichloromethane (15 ml), cooled under nitrogen to 3° C., was added dropwise, over 7 min, dried pyridine (6.81 ml, 84.2 mmol). The resulting colourless solution was stirred at 3° C. for 3 min, then a solution of hydrocinnamoyl chloride (5.00 ml, 33.7 mmol) in anhydrous dichloromethane (13 ml) was added dropwise over 2.5 h, whilst maintaining the temperature below 6° C. The resulting orange cloudy mixture was stirred at 3° C. for 1 h, then at room temperature for 2.5 h. The mixture was diluted with dichloromethane (20 ml) and poured into ice-cold 1M aqueous HCl (42 ml). The aqueous layer was further extracted with dichloromethane (2×25 ml), and the combined organic extracts were washed with 1M aqueous HCl (2×25 ml), then saturated aqueous NaCl (25 ml), dried ($Na_2SO_4$) and evaporated in vacuo to leave 9.06 g of crude 5-benzylacetyl-2,2-dimethyl-1,3-dioxane-4,6-dione as an orange oil.

This was dissolved in ethanol (55 ml) and the solution was heated at reflux under nitrogen for 2.5 h. The solvent was removed in vacuo and the residue was purified by flash chromatography (silica gel, 10% EtOAc/hexane) to give 5.582 g (75%) of the title compound as a colourless oil; $^1$H NMR (250 MHz, $CDCl_3$) 1.26 (3H, t, J 7.1 Hz), 2.90 (4H, m), 3.42 (2H, s), 4.18 (2H, q, J 7.1 Hz), 7.17–7.32 (5H, m).

b) Ethyl 3-benzyl-1,4-dihydro-4-oxo-5-pyridinecarboxylate

To a solution of sodium (0.5835 g, 25.4 mmol) in ethanol (18 ml) under nitrogen, was added ethyl 3-oxo-5-phenylpentanoate (5.5752 g, 25.3 mmol) in ethanol (5 ml) and 1,3,5-triazine (2.0544 g, 25.3 mmol). The mixture was heated at reflux for 1 h, then allowed to cool. The solvent was removed in vacuo, and water (15 ml) was added to the residue. The pH was brought to 4 by the addition of concd HCl (3 ml) and the mixture was left overnight. The resulting solid was collected by filtration, washed with ethanol and dried under vacuum at 60° C. to yield 4.6324 g (71%) of the title compound as a buff solid; $^1$H NMR (360 MHz, DMSO-$d_6$) δ1.24 (3H, t, J 7.1 Hz), 3.64 (2H, s), 4.16 (2H, q, J 7.1 Hz), 7.15–7.28 (5H, m), 7.53 (1H, s), 8.18 (1H, s), 11.64 (1H, br s).

c) Ethyl 3-benzyl-4-chloro-5-pyridinecarboxylate

Following a similar procedure to that described in Example 2, Step a, except using ethyl 3-benzyl-1,4-dihydro-4-oxo-5-pyridinecarboxylate instead of ethyl 1,4-dihydro-4-oxo-3-propyl-5-pyridinecarboxylate, the title compound was prepared in 83% yield as a pale yellow oil; 1H NMR (360 MHz, $CDCl_3$) δ1.41 (3H, t, J 7.1 Hz), 4.16 (2H, s), 4.43 (2H, q, J 7.1 Hz), 7.17–7.33 (5H, m), 8.49 (1H, s), 8.83 (1H, s); MS ($ES^+$) m/z 276/278 $[MH]^+$.

d) 7-Benzyl-2-(4-chlorophenyl)-2,5-dihydropyrazolo[4,3-c]pryidin-3-one hydrochloride Following a similar procedure to that described in Example 4, except using ethyl 3-benzyl-4-chloro-5-pyridinecarboxylate instead of ethyl 4-chloro-3-propyl-5-pyridinecarboxylate, the title compound was prepared in 50% yield as a cream solid; mp 175–180° C. ($CH_2Cl_2$-MeOH—HCl-$Et_2$O-EtOAc); $^1$H NMR (360 MHz, DMSO-$d_6$) δ3.98 (2H, m), 7.21 (1H, t, J 7.3 Hz), 7.30 (2H, t, J 7.2 Hz), 7.36 (1H, s), 7.42 (2H, d, J 7.2 Hz), 7.49 (2H, d, J 8.9 Hz), 8.25 (2H, d, J 8.9 Hz), 8.52 (1H, s), 12.36 (1H, br s); MS ($ES^+$) m/z 336/338 $[MH]^+$. Anal. found: C, 62.16; H, 3.83; N, 11.36. $C_{19}H_{14}ClN_3O.0.9HCl$ requires: C, 61.91; H, 4.07; N, 11.40%.

EXAMPLE 6

7-Benzyl-2,5-dihydro-2-(4-methoxyphenyl)pyrazolo [4,3-c]pryidin-3-one hydrochloride Following a similar procedure to that described in Example 4, except using ethyl 3-benzyl-4-chloro-5-pyridinecarboxylate and 4-methoxyphenylhydrazine hydrochloride instead of ethyl 4-chloro-3-propyl-5-pyridinecarboxylate and 4-chlorophenylhydrazine hydrochloride, the title compound was prepared, after trituration with $CH_2Cl_2$-Me-OH—HCl—$Et_2$O, in 30% yield as a cream solid, mp 179–185° C.; $^1$H NMR (360 MHz, DMSO-$d_6$) δ3.78 (3H, s), 4.00 (2H, m), 7.01 (2H, d, J 9.2 Hz), 7.21 (1H, t, J 7.3 Hz), 7.31 (2H, t, J 7.3 Hz), 7.41 (1H, s), 7.42 (2H, d, J 7.0 Hz), 8.05 (2H, d, J 9.2 Hz), 8.56 (1H, s), 12.52 (1H, br s); MS ($ES^+$) m/z 332 $[MH]^+$. Anal. found: C, 65.36; H, 4.86; N, 11.25. $C_{20}H_{17}N_3O_2.HCl$ requires: C, 65.31; H, 4.93; N, 11.42%.

EXAMPLE 7

3,6-Dihydro-3-oxo-2-phenyl-2H-pyrazolo[4,3-c] pyridine-7-carboxylic acid propylamide a) Diethyl 4-chloro-3,5-pyridinedicarboxylate Following a similar procedure to that described in Example 1, Step a, except using diethyl 1,4-dihydro-4-oxo-3,5-pyridinedicarboxylate (prepared from diethyl 1,3-acetonedicarboxylate as described in *J. Heterocyclic Chem.* 1980, 17, 359–368) instead of ethyl 1,4-dihydro-4-oxo-3-phenyl-5-pyridinecarboxylate, the title compound was prepared, after purification by flash chromatography (silica gel, 10% EtOAc/hexane), in quantitative yield; $^1$H NMR (250 MHz, $CDCl_3$) δ1.43 (6H, t, J 7.1 Hz), 4.46 (4H, q, J 7.1 Hz), 8.98 (2H, s); MS ($ES^+$) m/z 258/260 $[MH]^+$.

b) 3,5-Dihydro-3-oxo-2-phenyl-2H-pyrazolo[4,3-c] pyridine-7-carboxylic acid ethyl ester A mixture of diethyl 4-chloro-3,5-pyridinedicarboxylate (3.09 g, 12.0 mmol) and phenylhydrazine (1.42 ml, 14.4 mmol) in ethanol (100 ml) was degassed by evaporating under vacuum and refilling with nitrogen several times. The mixture was then stirred at reflux for 17 h under nitrogen. The mixture was left to cool in the fridge for a few hours, then filtered from a solid, which was washed with ethanol and ethyl acetate. The combined filtrates were evaporated in vacuo, and the residue was purified by flash chromatography (silica gel, 5% MeOH/$CH_2Cl_2$) to afford 1.559 g (46%) as an orange solid; $^1$H NMR (360 MHz, DMSO-$d_6$) δ1.35 (3H t, J 7.1 Hz), 4.34 (2H, q, J 7.1 Hz), 7.18 (1H, t, J 7.3 Hz), 7.44 (2H, t, J 7.5 Hz), 8.14 (1H, s), 8.19 (2H, d, J 7.6 Hz), 8.57 (1H, s), 12.49 (1H, br s).

c) 3,5-Dihydro-3-oxo-2-phenyl-2H-pyrazolo[4,3-c] pyridine-7-carboxylic acid

A mixture of 3,5-dihydro-3-oxo-2-phenyl-2H-pyrazolo[4,3-c]pyridine-7-carboxylic acid ethyl ester (0.9522 g, 3.36 mmol) in 1N aqueous NaOH (16 ml, 16.0 mmol) was stirred at room temperature for 3.25 h. The mixture was filtered, and the filtrate was neutralised to pH 5 by the addition of 5N aqueous HCl (3 ml). The resulting solid was collected by filtration, washed with water, then hexane, and dried under vacuum at 70° C. to leave 0.6498 g (76%) of the title compound as an orange solid; mp 287–302° C.; $^1$H NMR (360 MHz, DMSO-$d_6$) δ7.18 (1H, t, J 7.4 Hz), 7.44 (2H, t, J 7.5 Hz), 8.12 (1H, s), 8.17 (2H, d, J 7.6 Hz), 8.56 (1H, s), 12.66 (1H, br s); MS ($ES^+$) m/z 256 $[MH]^+$. Anal. found: C, 59.81; H, 3.49; N, 16.27. $C_{13}H_9N_3O_3.0.3H_2O$ requires: C, 59.91; H, 3.71; N, 16.12%.

d) 3,5-Dihydro-3-oxo-2-phenyl-2H-pyrazolo[4,3-c] pyridine-7-carboxylic acid propylamide To a solution of 3,5-dihydro-3-oxo-2-phenyl-2H-pyrazolo [4,3-c]pyridine-7-carboxylic acid (50 mg, 0.196 mmol) in anhydrous N,N-dimethylacetamide (2 ml) was added propylamine (17.8 ml, 0.216 mmol), bis(2-oxo-3-oxazolidinyl) phosphinic chloride (55 mg, 0.216 mmol), then, dropwise, anhydrous triethylamine (60 ml, 0.430 mmol). The mixture was stirred under nitrogen at room temperature for 2 h. Water (5 ml) was then added and the mixture was stirred before collecting the solid by filtration. The solid was washed with water, then hexane, and dried under vacuum at 70° C. The solid was then purified by recrystallisation (CH$_2$Cl$_2$-MeOH-EtOAc) to afford 39.1 mg (67%) of the title compound as an orange solid; $^1$H NMR (360 MHz, DMSO-d$_6$) δ0.99 (3H, t, J 7.3 Hz), 1.62 (2H, sextet, J 7.2 Hz), 3.41 (2H, q, J 6.8 Hz), 7.21 (1H, t, J 7.4 Hz), 7.47 (2H, t, J 7.5 Hz), 8.16 (1H, s), 8.18 (2H, d, J 7.6 Hz), 8.68 (1H, s), 8.70 (1H, t), 12.69 (1H, br s); MS (ES$^+$) m/z 297 [MH]$^+$.

EXAMPLE 8

3,5-Dihydro-3-oxo-2-phenyl-2H-pyrazolo[4,3-c] pyridine-7-carboxylic acid thiazol-2-ylamide Following a similar procedure to that described in Example 7, Step d, except using 2-aminothiazole instead of propylamine, and purifying the solid by recrystallisation (CH$_2$Cl$_2$-MeOH), then by flash chromatography (silica gel, 5% MeOH/CH$_2$Cl$_2$) the title compound was prepared in 36% yield; $^1$H NMR (360 MHz, DMSO-d$_6$) δ7.26 (1H, t), 7.39 (1H, d, J 3.5 Hz), 7.53 (2H, t, J 7.6 Hz), 7.62 (1H, d, J 3.5 Hz), 8.19 (2H, d, J 7.7 Hz), 8.40 (1H, s), 8.78 (1H, s), 12.07 (1H, s), 13.02 (1H, br s); MS (ES$^+$) m/z 338 [MH]$^+$, 272, 186.

EXAMPLE 9

2-(4-Chlorophenyl)-2,5-dihydro-6-methyl-7-phenylpyrazolo[4.3-c]pryidin-3-one hydrochloride a) Diethyl aminomethylenemalonate To diethyl ethoxymethylenemalonate (50.13 g, 0.232 mmol), cooled to −20° C. under nitrogen, was added a 2.0 M solution of ammonia in ethanol (232 ml, 0.464 mmol) and the resulting solution was stirred at room temperature overnight. The solution was then evaporated in vacuo to give a quantitative yield of the title compound as a cream solid; $^1$H NMR (360 MHz, CDCl$_3$) 5 1.28 (3H, t, J 7.1 Hz), 1.35 (3H, t, J 7.1 Hz), 4.19 (2H, q, J 7.1 Hz), 4.26 (2H, q, J 7.1 Hz), 5.68 (1H, br s), 8.11 (1H, dd), 8.69 (1H, br s).

b) Ethyl 1,4-dihydro-2-methyl-4-oxo-3-phenyl-5-pyridinecarboxylate

A mixture of diethyl aminomethylenemalonate (5.00 g, 26.7 mmol), phenylacetone (3.51 ml, 26.7 mmol) and phosphorus pentoxide (6.67 g, 47.0 mmol) in anhydrous THF (40 ml) was stirred at room temperature under nitrogen for 2 days, during which time more phosphorus pentoxide (6.67 g, 47.0 mmol) was added. The solution was decanted from the paste, and the residue was washed with THF (18×30 ml). The combined washings were evaporated in vacuo and the residue was extracted with ethyl acetate (6×50 ml). The combined extracts were washed with saturated aqueous K$_2$CO$_3$ (75 ml), then saturated aqueous NaCl (75 ml), dried (MgSO$_4$) and evaporated in vacuo. The residue was purified by flash chromatography (silica gel, 20% EtOAc/hexane) to give 3.47 g of a mixture of enamines and phenylacetone.

This was added dropwise over 5 min to Dowtherm® A (35 ml), at reflux, and the resulting solution was heated at reflux for a further 5 min. After allowing to cool, the residue was purified by flash chromatography (silica gel, 0–2% MeOH/CH$_2$Cl$_2$) to afford 1.90 g (28%) of the title compound as a pale brown solid; $^1$H NMR (360 MHz, DMSO-d$_6$) δ1.25 (3H, t, J 7.1 Hz), 2.06 (3H, s), 4.18 (2H, q, J 7.1 Hz), 7.16 (2H, d, J 6.9 Hz), 7.30 (1H, t, J 7.3 Hz), 7.38 (2H, t, J 7.5 Hz), 8.15 (1H, br s), 11.74 (1H, br s); MS (ES$^+$) m/z 258 [MH]$^+$.

c) Ethyl 4-chloro-2-methyl-3-phenyl-5-pyridinecarboxylate

Following a similar procedure to that described in Example 2, Step a, except using ethyl 1,4-dihydro-2-methyl-4-oxo-3-phenyl-5-pyridinecarboxylate instead of ethyl 1,4-dihydro-4-oxo-3-propyl-5-pyridinecarboxylate, the title compound was prepared in 89% yield as a brown oil; $^1$H NMR (250 MHz, CDCl$_3$) δ1.42 (3H, t, J 7.1 Hz), 2.26 (3H, s), 4.44 (2H, q, J 7.1 Hz), 7.19 (2H, dd, J 7.9, J'1.5 Hz), 7.41–7.54 (3H, m), 8.86 (1H, s); MS (ES$^+$) m/z 276/278 [MH]$^+$.

d) 2-(4-Chlorophenyl)-2,5-dihydro-6-methyl-7-phenylpyrazolo[4,3-c]pyridin-3-one hydrochloride Following a similar procedure to that described in Example 4, except using ethyl 4-chloro-2-methyl-3-phenyl-5-pyridinecarboxylate instead of ethyl 4-chloro-3-propyl-5-pyridinecarboxylate, the title compound was prepared in 44% yield as a yellow solid; mp 346–348° C. (CH$_2$Cl$_2$-MeOH-HCl-Et$_2$O-EtOAc-hexane); $^1$H NMR (360 MHz, DMSO-d$_6$) δ2.25 (3H, s), 7.21 (1H, t, J 7.3 Hz), 7.41–7.45 (3H, m), 7.50–7.51 (4H, m), 8.12 (2H, d, J 9.0 Hz), 8.57 (1H, s), 12.54 (1H, br s); MS (ES$^+$) m/z 336 [MH]$^+$. Anal. found: C, 62.73; H, 4.10; N, 11.48. C$_{19}$H$_{14}$ClN$_3$O.0.8HCl requires: C, 62.53; H, 4.09; N, 11.51%.

EXAMPLE 10

2,5-Dihydro-2-(4-methoxyphenyl)-6-methyl-7-phenylpyrazolo[4,3-c]pyridin-3-one

Following a similar procedure to that described in Example 4, except using ethyl 4-chloro-2-methyl-3-phenyl-5-pyridinecarboxylate and 4-methoxyphenylhydrazine hydrochloride instead of ethyl 4-chloro-3-propyl-5-pyridinecarboxylate and 4-chlorophenylhydrazine hydrochloride, the title compound was prepared, after further purification by flash chromatography (silica gel, 5% MeOH/CH$_2$Cl$_2$) and recrystallization (CH$_2$Cl$_2$-MeOH-EtOAc), in 4% yield as a yellow solid; mp 300–310° C.; $^1$H NMR (360 MHz, DMSO-d$_6$) δ2.25 (3H, s), 3.74 (3H, s), 6.93 (2H, d, J 9.2 Hz), 7.43 (1H, m), 7.47–7.51 (4H, m), 7.95 (21H, d, J 9.1 Hz), 8.50(1H, s), 12.34 (1H, br s); MS (ES$^+$) m/z 332 [MH]$^+$. Anal. found: C, 72.15; H, 4.84; N, 12.66. C$_{20}$H$_{17}$ClN$_3$O$_2$ requires: C, 72.49; H, 5.17; N, 12.68%.

EXAMPLE 11

2,5-Dihydro-6-methyl-2,7-diphelpyenrazolo[4,3-c] pyridin-3-one hydrochloride

Following a similar procedure to that described in Example 4, except using ethyl 4-chloro-2-methyl-3-phenyl-5-pyridinecarboxylate and phenylhydrazine instead of ethyl 4-chloro-3-propyl-5-pyridinecarboxylate and 4-chlorophenylhydrazine hydrochloride, the title compound was prepared in 68% yield as a yellow solid; mp 237–243° C. (CH$_2$Cl$_2$-MeOH-HCl-Et$_2$O-EtOAc); $^1$H NMR (360 MHz, DMSO-d$_6$) δ2.28 (3H, s), 7.14 (1H, t, J 7.4 Hz), 7.38 (2m , t, J 7.5 Hz), 7.44 (1H, m), 7.49–7.53 (4H, 8n), 8.04 (2H, d, J 7.8 Hz), 8.59 (1H, s), 12.70 (1H, br s); MS (ES$^+$) m/z 302 [MH]$^+$. Anal. found: C, 67.41; H, 4.48; N, 12.32. C$_{19}$H$_{15}$N$_3$O.HCl requires: C, 67.56; H, 4.77; N, 12.44%.

EXAMPLE 12

2,5-Dihydro-6-methyl-2-(4-methplahenyl)-7-phenylpyrazolo[4,3-c]-pyridin-3-one hydrochloride Following a similar procedure to that described in Example 4, except using ethyl 4-chloro-2-methyl-3-phenyl-5-pyridinecarboxylate and p-tolylhydrazine hydrochloride instead of ethyl 4-chloro-3-propyl-5-pyridinecarboxylate and 4-chlorophenylhydrazine hydrochloride, the title compound was prepared in 28% yield as a pale yellow solid; mp 315–321° C. (CH$_2$Cl$_2$—HCl—Et$_2$O-EtOAc); $^1$H NMR (360 MHz, DMSO-d$_6$) δ2.27 (3H, s), 2.28 (3H, s), 7.18 (2H, d, J 8.6 Hz), 7.44 (1H, m), 7.51–7.52 (4H, m), 7.91 (2H, d, J 8.5 Hz), 8.57 (1H, s), 12.64 (1H, br s); MS (ES$^+$) m/z 316 [MH]$^+$. Anal. found: C, 66.93; H, 4.95; N, 11.67. C$_{20}$H$_{17}$N$_3$O.HCl.0.1CH$_2$Cl$_2$ requires: C, 67.00; H, 5.09; N, 11.66%.

EXAMPLE 13

2-(4-Fluorophenyl)-2,5-dihydro-6-methyl-7-phenylpyrazolo[4,3-c]pyridin-3-one Following a similar procedure to that described in Example 4, except using ethyl 4-chloro-2-methyl-3-phenyl-5-pyridinecarboxylate and 4-fluorophenylhydrazine hydrochloride instead of ethyl 4-chloro-3-propyl-5-pyridinecarboxylate and 4-chlorophenylhydrazine hydrochloride, the title compound was prepared, after further purification by flash chromatography (silica gel, 5% MeOH/CH$_2$Cl$_2$), in 19% yield as a yellow solid; mp 303–317° C. (CH$_2$Cl$_2$-MeOH-EtOAc); $^1$H NMR (360 MHz, DMSO-d$_6$) δ2.25 (3H, s), 7.20 (2H, t, J 9.0 Hz), 7.42 (1H, m), 7.50–7.51 (4H, m), 8.09 (2H, dd, J 9.2, J'5.2 Hz), 8.55 (1H, d), 12.43 (1H, br s); MS (ES$^+$) m/z 320 [MH]$^+$. Anal. found: C, 69.91; H, 4.15; N, 13.25. C$_{19}$H$_{14}$FN$_3$Oe.0.3H$_2$O requires: C, 70.27; H, 4.53; N, 12.94%.

EXAMPLE 14

6-Ethyl-2,5-dihydro-2-(4-methoxylhenyl)-7-phenylpyrazolo[4,3-c]pyridin-3-one a) Ethyl 2-ethyl-1,4-dihydro-4-oxo-3-phenyl-5-pyridinecarboxylate and ethyl 2-benzyl-1,4-dihydro-3-methyl-4-oxo-5-pyridinecarboxylate Following a similar procedure to that described in Example 9, Step b, except using 1-phenyl-2-butanone instead of phenylacetone, the title compounds were prepared as a 88:12 mixture in 25% yield; MS (ES$^+$) m/z 272 [MH]$^+$, 226 [M—OEt]$^+$.

b) Ethyl 4-chloro-2-ethyl-3-phenyl-5-pyridinecarboxylate and ethyl 2-benzyl-4-chloro-3-methyl-5-pyridinecarboxlate Following a similar procedure to that described in Example 2, Step a, except using the product mixture from Example 14, Step a, instead of ethyl 1,4-dihydro-4-oxo-3-propyl-5-pyridinecarboxylate, the title compounds were prepared in 99% yield as a 88:12 mixture. The title compounds were separated by flash chromatography (alumina, 20% Et$_2$O/hexane).

Ethyl 4-chloro-2-ethyl-3-phenyl-5-pyridinecarboxylate; $^1$H NMR (360 MHz, CDCl$_3$) δ1.14 (3H, t, J 7.5 Hz), 1.41 (3H, t, J 7.1 Hz), 2.59 (2H, t, J 7.5 Hz), 4.43 (2H, q, J 7.1 Hz), 7.19 (2H, dd, J 8.0, J'1.7 Hz), 7.42–7.51 (3H, m), 8.90 (1H, s); MS (ES$^+$) m/z 290/292 [MH]$^+$.

Ethyl 2-benzyl-4-chloro-3-methyl-5-pyridinecarboxylate; $^1$H NMR (360 MHz, CDCl$_3$) δ1.41 (3H, t, J 7.1 Hz), 2.36 (3H, s), 4.28 (2H, s), 4.42 (2H, q, J 7.1 Hz), 7.15 (2H, d, J 7.2 Hz), 7.20 (1H, t, J 7.2 Hz), 7.27 (2H, t, J 7.6 Hz), 8.78 (1H, s); MS (ES$^+$) m/z 290/292 [MH]$^+$.

c) 6-Ethyl-2,5-dihydro-2-(4-methoxyphenyl)-7-phenylpyrazolo4,3-c[pyridin-3-one

Following a similar procedure to that described in Example 3, except using ethyl 4-chloro-2-ethyl-3-phenyl-5-pyridinecarboxylate instead of ethyl 4-chloro-3-propyl-5-pyridinecarboxylate, the title compound was prepared in 5% yield as a yellow solid; mp 233–245° C.; $^1$H NMR (500 MHz, DMSO-d$_6$) δ1.14 (3H, t, J 7.5 Hz), 2.54 (2H, q, J 7.5 Hz), 3.74 (3H, s), 6.93 (2H, d, J 9.1 Hz), 7.42–7.46(3H, m), 7.51(2H, t, J 7.4 Hz), 7.93(2H, d, J 9.1 Hz), 8.52 (1H, s); MS (ES$^+$) m/z 346 [MH]$^+$.

EXAMPLE 15

6-Ethyl-2, 5-dihydro-2,7-diphenylpyrazolo[4,3-c] pyridin-3-one hydrochloride Following a similar procedure to that described in Example 4, except using ethyl 4-chloro-2-ethyl-3-phenyl-5-pyridinecarboxylate and phenylhydrazine instead of ethyl 4-chloro-3-propyl-5-pyridinecarboxylate and 4-chlorophenylhydrazine hydrochloride, the title compound was prepared in 35% yield as a yellow solid; mp 239–247° C.; $^1$H NMR (500 MHz, DMSO-d$_6$) δ1.14 (3H, t, J 7.5 Hz), 2.54 (2H, q, J 7.5 Hz), 7.12 (1H, t, J 7.4 Hz), 7.39 (2H, t, J 7.6 Hz), 7.42–7.54 (5H, m), 8.02 (2H, d, J 7.7 Hz), 8.58 (1H, s), 12.59 (1H, br s); MS (ES$^+$) m/z 316 [MH]$^+$; Anal. found: C, 68.03; H, 5.22; N, 11.79. C$_{20}$H$_{17}$N$_3$O.HCl requires: C, 68.28; H, 5.16; N, 11.94%.

EXAMPLE 16

2,5-Dihydro-2,7-bis(4-methoxyphenyl)-6-methylpyrazolo[4,3-c]pyridin-3-one a) Ethyl 1,4-dihydro-3-(4-methoxyhenyl)-2-methyl-4-oxo-5-pyridinecarboxylate Following a similar procedure to that described in Example 9, Step b, except using 4-methoxyphenylacetone instead of phenylacetone, the title compound was prepared in 6% yield as a pale brown solid; $^1$H NMR (360 MHz, CDCl$_3$) δ1.44 (3H, t, J 7.1 Hz), 2.37 (3H, s), 3.86 (3H, s), 4.46 (2H, q, J 7.1 Hz), 7.01 (2H, d, J 8.7 Hz), 7.19 (2H, t, J 8.7 Hz), 8.86 (1H, s), 11.34 (1H, br s); MS (ES$^+$) m/z 288 [MH]$^+$, 260, 242 [M—OEt]$^+$.

b) Ethyl 4-chloro-3-(4-methoxyphenyl)-2-methyl-5-pyridinecarboxylate

Following a similar procedure to that described in Example 2, Step a, except using ethyl 1,4-dihydro-3-(4-methoxyphenyl)-2-methyl-4-oxo-5-pyridinecarboxylate instead of ethyl 1,4-dihydro-4-oxo-3-propyl-5-pyridinecarboxylate, the title compound was prepared in 94% yield as an almost colourless oil; $^1$H NMR (360 MHz, CDCl$_3$) δ1.41 (3H, t, J 7.1 Hz), 2.36 (3H, s), 3.87 (3H, s), 4.43 (2H, q, J 7.1 Hz), 7.01 (2H, d, J 8.7 Hz), 7.11 (2H, d, J 8.8 Hz), 8.82 (1H, s); MS (ES$^+$) m/z 308/306 [MH]$^+$, 278/280.

c) 2,5-Dihydro-2,7-bis(4-methoxyphenyl)-6-methylpyrazolo[4,3-c]pyridin-3-one

A mixture of ethyl 4-chloro-3-(4-methoxyphenyl)-2-methyl-5-pyridinecarboxylate (0.1842 g, 0.602 mmol) and 4-methoxyphenylhydrazine hydrochloride (0.1000 g, 0.724 mmol) in anhydrous 1-butanol (7 ml) was degassed by evaporating the flask under vacuum and refilling with nitrogen several times. The mixture was then stirred at reflux under nitrogen for 32 h, during which time more 4-methoxyphenylhydrazine hydrochloride (0.1001 g, 0.724 mmol) was added. The solvent was removed in vacuo and the residue was purified by flash chromatography (silica gel, 3–7% MeOH/CH$_2$Cl$_2$) to give 45.5 mg (21%) of the title compound as a yellow solid; mp 274–282° C. (CH$_2$Cl$_2$-MeOH-EtOAc); $^1$H NMR (360 MHz, DMSO-d$_6$) δ2.40 (3H, s), 3.88 (3H, s), 3.96 (3H, s), 7.08 (2H, d, J 9.2 Hz), 7.19 (2H, d, J 8.7 Hz), 7.59 (2H, d, J 8.7 Hz), 8.11 (2H, d, J 9.1 Hz), 8.61 (1H, s), 12.43 (1H, br s); MS (ES$^+$) m/z 362 MH]$^+$.

Anal. found: C, 69.95; H, 5.02; N, 11.60. $C_{21}H_{19}N_3O_3$ requires: C, 69.79; H, 5.30; N, 11.63%.

EXAMPLE 17

2-(4-Chlorophenyl)-2,5-dihydro-7-(4-methoxyphenyl)-6-methyl-pyrazolo[4,3-c]pyridin-3-one hydrochloride Following a similar procedure to that described in Example 4, except using ethyl 4-chloro-3-(4-methoxyphenyl)-2-methyl-5-pyridinecarboxylate instead of ethyl 4-chloro-3-propyl-5-pyridinecarboxylate, the title compound was prepared in 75% yield as a yellow solid; mp 271–281° C. ($CH_2Cl_2$-MeOH-HCl-$Et_2$O-EtOAc); $^1$H NMR (360 MHz, DMSO-$d_6$) δ2.27 (3H, s), 3.83 (3H, s), 7.06 (2H, d, J 8.7 Hz), 7.42 (2H, d, J 9.2 Hz), 7.45 (2H, d, J 8.9 Hz), 8.13 (2H, d, J 9.0 Hz), 8.54 (1H, s), 12.50 (1H, br s); MS (ES$^+$) m/z 366/368 [MH]$^+$. Anal. found: C, 60.75; H, 4.19; N, 10.84. $C_{20}H_{16}N_3O_2 \cdot 0.8HCl$ requires: C, 60.82; H, 4.29; N, 10.64%.

EXAMPLE 18

2,7-Bis(4-chlorophenyl)-2,5-dihydro-6-methylpyrazolo[4,3-c]pyridin-3-one hydrochloride a) Ethyl 3-(4-chlorophenyl)-1,4-dihydro-2-methyl-4-oxo-5-p)pyridinecarboxylate A mixture of diethyl aminomethylenemalonate (5.066 g, 27.1 mmol), 4-chlorophenylacetone (4.563 g, 27.1 mmol) and phosphorus pentoxide (6.77 g, 47.7 mmol) in anhydrous THF (40 ml) was stirred at room temperature under nitrogen for 7 days. The solution was decanted from the paste, and the residue was washed with THF (8×50 ml), then dichloromethane (24×50 ml). The combined washings were evaporated in vacuo and the residue was extracted with ethyl acetate (5×50 ml). The combined extracts were washed with saturated aqueous $K_2CO_3$ (75 ml), then saturated aqueous NaCl (75 ml), dried (MgSO$_4$) and evaporated in vacuo. The residue was purified by flash chromatography (alumina, 50% $CH_2Cl_2$/hexane) to give 2.15 g of a mixture of enamines and 4-chlorophenylacetone.

This was added dropwise over 5 min to Dowtherm® A (22 ml), at reflux, and the resulting solution was heated at reflux for a further 3 min. After allowing to cool overnight, the resulting precipitate was collected by filtration, washed with diethyl ether, and dried at 60° C. under vacuum to afford 0.988 g (13%) of the title compound; $^1$H NMR (360 MHz, DMSO-$d_6$) δ1.24 (3H, t, J 7.1 Hz), 2.07 (3H, s), 4.18 (2H, q, J 7.1 Hz), 7.20 (2H, d, J 8.4 Hz), 7.43 (2H, t, J 8.4 Hz), 8.15 (1H, s), 11.79 (1H, br s); MS (ES$^+$) m/z 292/294 [MH]$^+$.

b) Ethyl 4-chloro-3-(4-chlorophenyl)-2-methyl-5-pyridinecarboxylate

Following a similar procedure to that described in Example 2, Step a, except using ethyl 3-(4-chlorophenyl)-1,4-dihydro-2-methyl-4-oxo-5-pyridinecarboxylate instead of ethyl 1,4-dihydro-4-oxo-3-propyl-5-pyridinecarboxylate, the title compound was prepared in 90% yield as a buff solid; $^1$H NMR (360 MHz, CDCl$_3$) δ1.41 (3H, t, J 7.1 Hz), 2.35 (3H, s), 4.43 (2H, q, J 7.1 Hz), 7.13 (2H, d, J 8.4 Hz), 7.47 (2H, d, J 8.3 Hz), 8.86 (1H, s); MS (ES$^+$) m/z 310/312/314 [H]$^+$.

c) 2,7-Bis(4-chlorophenyl) -2,5-dihydro-6-methylpyrazolo[4,3-c]pyridin-3-one hydrochloride Following a similar procedure to that described in Example 4, except using ethyl 4-chloro-3-(4-chlorophenyl)-2-methyl-5-pyridinecarboxylate instead of ethyl 4-chloro-3-propyl-5-pyridinecarboxylate, the title compound was prepared in 70% yield as a yellow solid; mp 333–337° C. (MeOH-HCl-$Et_2$O); $^1$H NMR (360 MHz, DMSO-$d_6$) δ2.26 (3H, s), 7.42 (2H, d, J 8.9 Hz), 7.56 (4H, s), 8.12 (2H, d, J 9.0 Hz), 8.57 (1H, s), 12.55 (1H, br s); MS (ES$^+$) m/z 370/372/374 [MH]$^+$. Anal. found: C, 57.56; H, 3.89; N, 10.19. $C_{19}H_{13}Cl_2N_3O \cdot 0.6HCl \cdot 0.44CH_4O$ requires: C, 57.48; H, 3.81; N, 10.34%.

EXAMPLE 19

2-(4-Chlorophenyl)-2,5-dihydro-7-(3-methoxyphenyl)-6-methyl-pyrazolo[4,3-c]pyridin-3-one hydrochloride a) Ethyl 1,4-dihydro-3-(3-methoxyphenyl)-2-methyl-4-oxo-5-pyridinecarboxylate A mixture of diethyl aminomethylenemalonate (5.764 g, 30.8 mmol), 3-methoxyphenylacetone (5.000 g, 30.5 mmol) and phosphorus pentoxide (7.604 g, 53.6 mmol) in anhydrous dichloromethane (45 ml) was stirred at room temperature under nitrogen overnight. The solution was decanted from the solid, and the residue was scraped from the flask and washed with dichloromethane (5×35 ml). The combined washings were evaporated in vacuo, and the residue was taken up in ethyl acetate (100 ml), washed with saturated aqueous $K_2CO_3$ (40 ml), then saturated aqueous NaCl (40 ml), dried (MgSO$_4$) and evaporated in vacuo. The residue was purified by flash chromatography (alumina, 40% $CH_2Cl_2$/hexane) to give 0.873 g of a mixture of enamines.

This was added dropwise over 8 min to Dowtherm® A (20 ml), at reflux, and the resulting solution was heated at reflux for a further 4 min. After allowing to cool, the residue was purified by flash chromatography (silica gel, 0–2% MeOH/$CH_2Cl_2$) to afford 0.656 g (8%) of the title compound; $^1$H NMR (250 MHz, CDCl$_3$) δ1.45 (3H, t, J 7.1 Hz), 2.37 (3H, s), 3.84 (3H, s), 4.46 (2H, q, J 7.1 Hz), 6.79–6.86 (2H, m), 6.95 (1H, m), 7.39 (1H, t, J 7.9 Hz), 8.88 (1H, s); MS (ES$^+$) m/z 288 [MH]$^+$, 242 [M—OEt]$^+$.

b) Ethyl 4-chloro-3-(3-methoxyphenyl)-2-methyl-5-pyridinecarboxylate

Following a similar procedure to that described in Example 2, Step a, except using ethyl 1,4-dihydro-3-(3-methoxyphenyl)-2-methyl-4-oxo-5-pyridinecarboxylate instead of ethyl 1,4-dihydro-4-oxo-3-propyl-5-pyridinecarboxylate, the title compound was prepared in 27% yield as an almost colourless oil; $^1$H NMR (250 MHz, CDCl$_3$) δ1.42 (3H, t, J 7.1 Hz), 2.37 (3H, s), 3.84 (3H, s), 4.43 (2H, q, J 7.1 Hz), 6.71–6.79 (2H, m), 6.98 (1H, m), 7.41 (1H, t, J 8.0 Hz), 8.85 (1H, s); MS (ES$^+$) m/z 306/308 [MH]$^+$.

c) 2-(4-Chlorophenyl)-2,5-dihydro-7-(3-methoxyphenyl)-6-methyl-pyrazolo[4,3-c]pyridin-3-one hydrochloride Following a similar procedure to that described in Example 4, except using ethyl 4-chloro-3-(3-methoxyphenyl)-2-methyl-5-pyridinecarboxylate instead of ethyl 4-chloro-3-propyl-5-pyridinecarboxylate, the title compound was prepared in 47% yield as a yellow solid; mp 244–246° C. ($CH_2Cl_2$-MeOH-HCl-$Et_2$O-EtOAc); $^1$H NMR (360 MHz, DMSO-$d_6$) δ2.26 (3H, s), 3.80 (3H, s), 7.00 (1H, m), 7.06 (1H, m), 7.07 (1H, s), 7.42 (1H, m), 7.43 (2H, d, J 8.9 Hz), 8.12 (2H, d, J 9.1 Hz), 8.56 (1H, s), 12.52 (1H, br s); MS (ES$^+$) m/z 366/368 [MH]$^+$. Anal. found: C, 60.18; H, 4.01; N, 10.29. $C_{20}H_{16}ClN_3O_2 \cdot 0.9HCl$ requires: C, 60.26; H, 4.27; N, 10.54%.

EXAMPLE 20

2-(4-Chlorophenyl)-2,5-dihydro-7-(2-methoxynhenyl)-6-methyl-pyrazolo[4,3-c]pyridin-3-one a) Ethyl 1,4-dihydro-3-(2-methoxyphenyl)-2-methyl-4-oxo-5-pyridinecarboxylate Following a similar procedure to that described in Example 9, Step b, except using 2-methoxyphenylacetone instead of phenylacetone, the title compound was prepared in 11% yield as a white solid; $^1$H NMR (250 MHz, CDCl$_3$) δ1.44 (3H, t, J 7.1 Hz), 2.37 (3H, s), 3.77 (3H, s), 4.45 (2H, q, J 7.1 Hz), 7.02 (1H, d, J 8.2 Hz), 7.07 (1H, td, J 7.3, J'0.8 Hz), 7.14 (1H, dd, J 7.5, J'2.0 Hz), 7.41 (1H, m), 8.88 (1H, s), 11.28 (1H, br s); MS (ES$^+$) m/z 288 [MH]$^+$, 242 [M—OEt]$^+$.

b) Ethyl 4-chloro-3-(2-methoxylphenyl)-2-methyl-5-pyridinecarboxylate

Following a similar procedure to that described in Example 2, Step a, except using ethyl 1,4-dihydro-3-(2-methoxyphenyl)-2-methyl-4-oxo-5-pyridinecarboxylate instead of ethyl 1,4-dihydro-4-oxo-3-propyl-5-pyridinecarboxylate, the title compound was prepared in 92% yield as a pale brown solid; $^1$H NMR (360 MHz, CDCl$_3$) δ1.42 (3H, t, J 7.1 Hz), 2.34 (3H, s), 3.75 (3H, s), 4.43 (2H, q, J 7.1 Hz), 7.02 (1H, d, J 8.3 Hz), 7.06–7.10 (2H, m), 7.44 (1H, m), 8.87 (1H, s); MS (ES$^+$) m/z 306/308 [MH]$^+$.

c) 2-(4-Chlorophenyl)-2,5-dihydro-7-(2-methoxyphenyl)-6-methyl-pyrazolo[4,3-c]pyridin-3-one A mixture of ethyl 4-chloro-3-(2-methoxyphenyl)-2-methyl 5-pyridinecarboxylate (0.101 g, 0.330 mmol) and 4-chlorophenylhydrazine hydrochloride (71.3 mg, 0.398 mmol) in anhydrous 1-butanol (4 ml) was degassed by evaporating the flask under vacuum and refilling with nitrogen several times and then stirred at reflux under nitrogen for 3 h. After leaving to cool overnight, the solvent was removed in vacuo, and the residue was purified by flash chromatography (silica gel, 3–5% MeOH/CH$_2$Cl$_2$) to afford 94.7 mg (78%) of the title compound as a yellow solid; mp 267–278° C. (CH$_2$Cl$_2$-EtOAc); $^1$H NMR (360 MHz, DMSO-d$_6$) δ2.08 (3H, s), 3.75 (3H, s), 7.07 (1H, t, J 7.5 Hz), 7.17 (1H, d, J 8.2 Hz), 7.31 (1H, dd, J 7.5, J'1.7 Hz), 7.40 (2H, d, J 9.1 Hz), 7.43 (1H, m), 8.09 (2H, d, J 8.9 Hz), 8.54 (1H, d), 12.42 (1H, br d); MS (ES$^+$) m /z 366/368 [MH]$^+$. Anal. found: C, 65.74; H, 4.41; N, 11.31. C$_{20}$H$_{16}$ClN$_3$O$_2$ requires: C, 65.67; H, 4.41; N, 11.49%.

EXAMPLE 21

2-(4-Chlorophenyl)-2,5-dihydro-6-methyl-7-(thiophen-2-yl)pyrazolo[4,3-c]pyridin-3-one hydrochloride a) Ethyl 1,4-dihydro-2-methyl-4-oxo-3-(thiophen-2-yl)-5-pyridinecarboxylate Following a similar procedure to that described in Example 19, Step a, except using 2-thiophenylacetone instead of 3-methoxyphenylacetone, the title compound was prepared in 13% yield as a pale brown solid; $^1$H NMR (250 MHz, CDCl$_3$) δ1.45 (3H, t, J 7.1 Hz), 2.48 (3H, s), 4.47 (2H, q, J 7.1 Hz), 7.03 (1H, dd, J 3.5, J'1.2 Hz), 7.16 (1H, dd, J 5.2, J'3.6 Hz), 7.49 (1H, dd, J 5.2, J'1.2 Hz), 8.87 (1H, s), 11.56 (1H, br s); MS (ES$^+$) m/z 264 [MH]$^+$, 236, 218 [M—OEt]$^+$.

b) Ethyl 4-chloro-2-methyl-3-(thiophen-2-yl)-5-pyridinecarboxylate

Following a similar procedure to that described in Example 2, Step a, except using ethyl 1,4-dihydro-2-methyl-4-oxo-3-(thiophen-2-yl)-5-pyridinecarboxylate instead of ethyl 1,4-dihydro-4-oxo-3-propyl-5-pyridinecarboxylate, the title compound was prepared in 87% yield as a brown oil; $^1$H NMR (250 MHz, CDCl$_3$) δ1.42 (3H, t, J 7.1 Hz), 2.46 (3H, s), 4.43 (2H, q, J 7.1 Hz), 6.96 (1H, dd, J 3.5, J'1.2 Hz), 7.17 (1H, dd, J 5.1, J'3.5 Hz), 7.51 (1H, dd, J 5.1, J'1.2 Hz), 8.87 (1H, s); MS (ES$^+$) m/z 282/284 [MH]$^+$.

c) 2-(4-Chlorophenyl)-2,5-dihydro-6-methyl-7-(thiophen-2-yl)pyrazolo[4,3-c]pyridin-3-one hydrochloride Following a similar procedure to that described in Example 4, except using ethyl 4-chloro-2-methyl-3-(thiophen-2-yl)-5-pyridinecarboxylate instead of ethyl 4-chloro-3-propyl-5 -pyridinecarboxylate, the title compound was prepared in 57% yield as a pale brown solid; mp 310° dec (CH$_2$Cl$_2$-MeOH-HCl-Et$_2$O-EtOAc); $^1$H NMR (360 MHz, DMSO-d$_6$) δ2.49 (3H, s), 7.24 (1H, dd, J 5.2, J'3.8 Hz), 7.47 (2H, d, J 9.0 Hz), 7.55 (1H, dd, J 3.8, J'1.2 Hz), 7.76 (1H, dd, J 5.2, J'1.2 Hz), 8.22 (2H, d, J 9.0 Hz), 8.54 (1H, d), 12.58 (1H, br s); MS (ES$^+$) m/z 342/344 [MH]$^+$. Anal. found: C, 55.83; H, 3.33; N, 11.29. C$_{17}$H$_{12}$ClN$_3$O.0.6HCl requires: C, 56.14; H, 3.49; N, 11.55%.

EXAMPLE 22

2-(4-Chlorophenyl)-2,5-dihydro-7-(3-iodophenyl)-6-methylpyrazolo[4,3-c]pyridin-3-one a) Ethyl 1,4-dihydro-3-(3-iodophenyl)-2-methyl-4-oxo-5-pyridinecarboxylate Following a similar procedure to that described in Example 19, Step a, except using 3-iodophenylacetone (prepared from 3-iodophenylacetonitrile as described in *J. Med. Chem.* 1970, 13, 1040–1042) instead of 3-methoxyphenylacetone, the title compound was prepared in 29% yield as a pale brown solid; $^1$H NMR (250 MHz, CDCl$_3$) δ1.45 (3H, t, J 7.1 Hz), 2.36 (3H, s), 4.47 (2H, q, J 7.1 Hz), 7.18–7.27 (2H, m), 7.64 (1H, t, J 1.4 Hz), 7.75 (1H, dt, J 6.7, J'1.7 Hz), 8.88 (1H, s), 11.38 (1H, br s); MS (ES$^+$) m/z 384 [MH]$^+$, 338 [M—OEt]$^+$.

b) Ethyl 4-chloro-3-(3-iodophenyl)-2-methyl-5-pyridinecarboxylate

Following a similar procedure to that described in Example 2, Step a, except using ethyl 1,4-dihydro-3-(3-iodophenyl)-2-methyl-4-oxo-5-pyridinecarboxylate instead of ethyl 1,4-dihydro-4-oxo-3-propyl-5-pyridinecarboxylate, the title compound was prepared in 68% yield as an almost colourless oil; $^1$H NMR (250 MHz, CDCl$_3$) δ1.42 (3H, t, J 7.1 Hz), 2.36 (3H, s), 4.43 (2H, q, J 7.1 Hz), 7.17 (1H, dt, J 7.7, J'1.5 Hz), 7.24 (1H, t, J 7.6 Hz), 7.57 (1H, t, J 1.4 Hz), 7.79 (1H, dt, J 7.6, J'1.5 Hz), 8.87 (1H, s); MS (ES$^+$) m/z 402/404 [MH]$^+$.

c) 2-(4-Chlorophenyl)-2,5-dihydro-7-(3-iodophenyl)-6-methylpyrazolo[4,3-c]pyridin-3-one Following a similar procedure to that described in Example 4, except using ethyl 4-chloro-3-(3-iodophenyl)-2-methyl-5-pyridinecarboxylate instead of ethyl 4-chloro-3-propyl-5-pyridinecarboxylate, the title compound was prepared, after further purification by flash chromatography (3–5% MeOH/CH$_2$Cl$_2$), in 59% yield as a yellow-brown solid; mp 306–312° C. (CH$_2$Cl$_2$-MeOH-EtOAc); $^1$H NMR (360 MHz, DMSO-d$_6$) δ2.24 (3H, s), 7.32 (1H, t, J 7.8 Hz), 7.43 (2H, d, J 9.1 Hz), 7.53 (1H, d, J 7.6 Hz), 7.80 (1H, d, J 8.0 Hz), 7.87 (1H, t, J 1.5 Hz), 8.11 (2H, d, J 9.1 Hz), 8.57 (1H, d), 12.50 (1H, br d); MS (ES$^+$) m/z 462/464 [MH]$^+$; Anal. found: C, 46.51; H, 3.04; N, 8.11. C$_{19}$H$_{13}$ClN$_3$O.1.8H$_2$O requires: C, 46.19; H, 3.39; N, 8.50%.

EXAMPLE 23

2-(4-Chlorophenyl)-2,5-dihydro-6-methyl-7-[3-(pyridin-3-yl)phenyl]-pyrazolo[4,3-c]pyridin-3-one A mixture of 2-(4-chlorophenyl)-2,5-dihydro-7-(3-iodophenyl)-6-methylpyrazolo[4,3c]pyridin-3-one (0.1009 g, 0.217 mmol), 3-pyridineboronic acid (37.8 mg, 0.306 mmol), sodium carbonate (64.5 mg, 0.609 mmol), and tetrakis(triphenylphosphine)palladium(0) (20.6 mg, 0.0178 mmol) in ethylene glycol dimethyl ether (2.7 ml) and water (1 ml) was degassed by evaporating the flask under vacuum and refilling with nitrogen several times. The mixture was then stirred at 100° C. for 15 h under nitrogen. The solvent was removed it vacuo and the residue was purified by flash chromatography (silica gel, 3–5% MeOH/CH$_2$Cl$_2$) to afford 60.7 mg (68%) of the title compound as a yellow solid; mp 312–318° C. (CH$_2$Cl$_2$-MeOH-EtOAc); $^1$H NMR (360 MHz, DMSO-d$_6$) δ2.31 (3H, s), 7.42 (2H, d, J 9.1 Hz), 7.51 (1H, dd), 7.59 (1H, dt, J 7.7, J'1.3 Hz), 7.65 (1H, t, J 7.7 Hz), 7.80 (1H, d, J 7.8 Hz), 7.86 (1H, t, J 1.5 Hz), 8.13 (3H, m), 8.59 (2H, m), 8.96 (1H, s), 12.51 (1H, br d, J 6.0 Hz); MS (ES$^+$) m/z 413/415 [MH]$^+$. Anal. found: C, 68.81; H, 3.99; N, 13.18. C$_{24}$H$_{17}$ClN$_4$O.0.3H$_2$O requires: C, 68.92; H, 4.24; N, 13.39%.

EXAMPLE 24

2-(4-Chlorophenyl)-2,5-dihydro-6-methyl-7-[3-(thiophen-2-yl)phenyl]-pyyrazolo[4,3-c]pyridin-3-one Following a similar procedure to that described in Example 23, except using 2-thiopheneboronic acid instead of 3-pyridineboronic acid, the title compound was prepared in 78% yield as an orange solid; mp 266–272° C. (CH$_2$Cl$_2$-MeOH-EtOAc); $^1$H NMR (360 MHz, DMSO-d$_6$) δ2.29 (3H, s), 7.16 (1H, dd, J 4.9, J'3.6 Hz), 7.40–7.45 (3H, m), 7.53–7.58 (3H, m), 7.72 (1H, dt, J 7.9, J'1.3 Hz), 7.81 (1H, t, J 1.6 Hz), 8.13 (2H, d, J 9.0 Hz), 8.59 (1H, s), 12.49 (1H, s); MS (ES$^+$) m/z 418/420 [MH]$^+$. Anal. found: C, 65.58; H, 3.53; N, 9.64. C$_{23}$H$_{16}$ClN$_3$OS.0.1H$_2$O requires: C, 65.81; H, 3.89; N, 10.01%.

EXAMPLE 25

2-(4-Chlorophenyl)-2,5-dihydro-6-methyl-7-[3-(3-methyl-12,4-oxadiazol-5-yl)phenyl]pyrazolo[4,3-c]pyridin-3-one a) 3-[2-(4-Chlorophenyl)-3,5-dihydro-6-methyl-3-oxo-2H-pyrazolo[4,3-c]pyridin-7-yl]benzoic acid butyl ester Into a mixture of 2-(4-chlorophenyl)-2,5-dihydro-7-(3-iodophenyl)-6-methylpyrazolo[4,3-c]pyridin-3-one (0.50 g, 1.08 mmol), dichlorobis-(triphenylphosphine)palladium(II) (22.8 mg, 0.0325 mmol), and tributylamine (0.284 ml, 1.19 mmol) in anhydrous 1-butanol (15 ml) was bubbled carbon monoxide gas for 15 min. The mixture was then stirred at 100° C. for 17 h under a balloon of carbon monoxide. The solvent was removed in vacuo and the residue was purified by flash chromatography (silica gel, 3–5% MeOH/CH$_2$Cl$_2$) to give 0.4523 g (96%) of the title compound as a yellow solid; mp 185–190° C. (CH$_2$Cl$_2$-MeOH-EtOAc); $^1$H NMR (360 MHz, DMSO-d$_6$) δ0.91 (3H, t, J 7.4 Hz), 1.42 (2H, sextet, J 7.5 Hz), 1.70 (2H, quintet, J 6.9 Hz), 2.25 (3H, s), 4.30 (2H, t, J 6.5 Hz), 7.41 (2H, d, J 9.0 Hz), 7.67 (1H, t, J 7.6 Hz), 7.79 (1H, br d, J 7.7 Hz), 8.02 (1H, br d, J 7.7 Hz), 8.11 (3H, m), 8.60 (1H, s), 12.51 (1H, br s); MS (ES$^+$) m/z 436/438 [MH]$^+$. Anal. found: C, 63.58; H, 4.99; N, 9.31. C$_{24}$H$_{22}$ClN$_{3l}$ $_{O3}$.0.9H$_2$O requires: C, 63.76; H, 5.31; N, 9.29%.

b) 2-(4-Chlorophenyl)-2, 5-dihydro-6-methyl-7-[3-(3-methyl-1,2 4-oxadiazol-5-yl)phenyl]pyrazolo[4,3-c]pyridin-3-one To a mixture of acetamide oxime (57.8 mg, 0.780 mmol) in anhydrous DMF (10 ml) under nitrogen was added sodium hydride (60% dispersion in oil, 27.5 mg, 0.688 mmol) and the mixture was stirred at room temperature for 30 min. A solution of 3-[2-(4-chlorophenyl)-3,5-dihydro-6-methyl-3-oxo-2H-pyrazolo[4,3-c]pyridin-7-yl]benzoic acid butyl ester (100 mg, 0.229 mmol) in anhydrous DMF (5 ml) was then added dropwise and the mixture was stirred at 80° C. for 2.5 h under nitrogen. The solvent was removed it vacuo and the residue was purified by flash chromatography (silica gel, 3–5% MeOH/CH$_2$Cl$_2$) to yield 74.6 mg (78%) of the title compound as an orange solid; mp 318–320° C. (CH$_2$Cl$_2$-MeOH-EtOAc); $^1$H NMR (360 MHz, DMSO-d$_6$) δ2.25 (3H, s), 2.43 (3H, s), 7.41 (2H, d, J 9.1 Hz), 7.76 (1H, t, J 7.6 Hz), 7.85 (1H, dt, J 7.8, J'1.5 Hz), 8.10–8.15 (3H, m), 8.22 (1H, t, J 1.5 Hz), 8.61 (1H, s), 12.54 (1H, br s); MS (ES$^+$) m/z 418/420 [MH]$^+$. Anal. found: C, 58.82; H, 4.05; N, 15.20. C$_{22}$H$_{16}$ClN$_5$O$_2$.1.8H$_2$O requires: C, 58.68; H, 4.39; N, 15.55%.

EXAMPLE 26

2-(4-Chlorophenyl)-2,5-dihydro-6-methyl-7-[3-(pyrrolidin-1-ylcarbonyl)phenyl]pyrazolo[4,3-c]pyridin-3-one a) 3-[2-(4-Chlorophenyl)-3,5-dihydro-6-methyl-3-oxo-2H-pyrazolo[4,3-c]pyridin-7-yl]benzoic acid A mixture of 3-[2-(4-chlorophenyl)-3,5-dihydro-6-methyl-3-oxo-2H-pyrazolo[4,3-c]pyridin-7-yl]benzoic acid butyl ester (from Example 25, Step a) (0.350 g, 0.803 mmol) in 1M aqueous NaOH (3.9 ml) was stirred at room temperature overnight. The mixture was then filtered from a little dark orange solid, which was washed with water, and the combined filtrates were neutralised to pH 5 by the addition of 5M aqueous HCl. The resulting yellow solid was collected by filtration, washed with water, then hexane, and dried at 70° C. under vacuum to afford 0.223 g (73%) of the title compound; $^1$H NMR (250 MHz, DMSO-d$_6$) δ2.25 (3H, s), 7.43 (2H, d, J 9.0 Hz), 7.65 (1H, t, J 7.7 Hz), 7.77 (1H, dt, J 7.8, J'1.5 Hz), 8.01 (1H, dt, J 7.7, J'1.4 Hz), 8.07 (1H, t, J 1.4 Hz), 8.12 (2H, d, J 9.0 Hz), 8.60 (1H, d), 12.57 (1H, d, J 6.3 Hz), 13.09 (1H, br s); MS (ES$^+$) m/z 380/382 [MH]$^+$.

b) 2-(4-Chlorophenyl)-2, 5-dihydro-6-methyl-7-[3-(pyrrolidin-1-ylcarbonyl)phenyl]pyrazolo[4,3-c]pyridin-3-one To a solution of 3-[2-(4-chlorophenyl)-3,5-dihydro-6-methyl-3-oxo-2H-pyrazolo[4,3-c]pyridin-7-yl]benzoic acid (65 mg, 0.171 mmol) in anhydrous N,N-dimethylacetamide (2 ml) was added pyrrolidine (15.7 ml, 0.188 mmol), bis(2-oxo-3-oxazolidinyl)phosphinic chloride (48.0 mg, 0.188 mmol), then, dropwise, anhydrous triethylamine (52.5 ml, 0.376 mmol). The mixture was stirred under nitrogen at room temperature for 18 h. The solvent was removed in vacuo and the residue was purified by flash chromatography (silica gel, 3–5% MeOH/CH$_2$Cl$_2$) to give 63.2 mg (85%) of the title compound as a yellow solid; mp 253–255° C.; $^1$H NMR (360 MHz, DMSO-d$_6$) δ1.85 (4H, m), 2.29 (3H, s), 3.49 (4H, br q, J 6.9 Hz), 7.41 (2H, d, J 9.0 Hz), 7.55–7.59 (3H, m), 7.66 (1H, s), 8.12 (2H, d, J 9.0 Hz), 8.58 (1H, s), 12.49 (1H, br s); MS (ES$^+$) m/z 433/435 [H]$^+$. Anal. found: C, 63.85; H, 4.96; N, 12.33. C$_{24}$H$_{21}$ClN$_4$O$_2$.H$_2$O requires: C, 63.93; H, 5.14; N, 12.42%.

EXAMPLE 27

2-(4-Chlorophenyl)-2,5-dihydro-6-methyl-7-[3-(4-methylpiperazin-1-ylcarbonyl)phenyl]pyrazolo[4,3-c]pyridin-3-one Following a similar procedure to that described in Example 26, except using 1-methylpiperazine instead of pyrrolidine, the title compound was prepared in 98% yield as a yellow solid; mp 318–322° C.; ¹H NMR (360 MHz, DMSO-d₆) δ2.30 (3H, s), 2.37 (3H, br s), 2.64 (4H, br m), 3.61 (4H, br m), 7.43 (2H, d, J 8.9 Hz), 7.47 (1H, m), 7.55 (1H, s), 7.58–7.63 (2H, m), 8.11 (2H, d, J 9.0 Hz), 8.54 (1H, s), 12.74 (1H, br s); MS (ES⁺) m/z 462/464 [MH]⁺.

EXAMPLE 28

2-(4-Chlorophenyl)-2,5-dihydro-6-methyl-7-[3-(imidazol-1-yl)phenyl]-pyrazolo[4,3-c]pyridin-3-one A mixture of 2-(4-chlorophenyl)-2,5-dihydro-7-(3-iodophenyl)-6-methylpyrazolo[4,3-c]pyridin-3-one (0.100 g, 0.217 mmol), imidazole (33.9 mg, 0.498 mmol), potassium carbonate (29.9 mg, 0.216 mmol), and copper bronze (1 mg) in 1-methyl-2-pyrrolidinone (0.6 ml) was heated at 140° C. under nitrogen for 90 h. Purification by flash chromatography (silica gel, 3–10% MeOH/CH₂Cl₂) gave 30.3 mg (35%) of the title compound. This was recrystallised from CH₂Cl₂-MeOH-EtOAc; ¹H NMR (400 MHz, DMSO-d₆) δ2.29 (3H, s), 7.16 (1H, br s), 7.42 (2H, d), 7.50 (1H, d, J 7.6 Hz), 7.65 (1H, t J 7.8 Hz), 7.73 (1H, d, J 8.1 Hz), 7.80 (1H, s), 7.85 (1H, br s), 8.11 (2H, d), 8.36 (1H, br s), 8.61 (1H, s), 12.53 (1H, br d, J 5.6 Hz); MS (ES⁺) m/z 402/404 [MH]⁺.

EXAMPLE 29

2-(4-Chloronhenyl)-2,5-dihydro-6-methyl-7-[4-pyridin-3-yl)phenyl]-pyrazolo[4,3-c]pyridin-3-one a) Ethyl 3-(4-bromophenyl)-1,4-dihydro-2-methyl-4-oxo-5-pyridinecarboxylate Following a similar procedure to that described in Example 19, Step a, except using 4-bromophenylacetone instead of 3-methoxyphenylacetone, the title compound was prepared, by collection of the precipitated solid after leaving the reaction mixture to cool overnight, followed by washing with diethyl ether and drying at 60° C. under vacuum, in 26% yield as a whitish solid; ¹H NMR (250 MHz, DMSO-d₆) δ1.24 (3H, t, J 6.9 Hz), 2.07 (3H, s), 4.17 (2H, q, J 7.1 Hz), 7.14 (2H, d, J 8.1 Hz), 7.57 (2H, t, J 8.1 Hz), 8.16 (1H, s), 11.86 (1H, br s); MS (ES⁺) m/z 336/338 [MH]⁺.

b) Ethyl 3-(4-bromophenyl)-4-chloro-2-methyl-5-pyridinecarboxylate

Following a similar procedure to that described in Example 2, Step a, except using ethyl 3-(4-bromophenyl)-1,4-dihydro-2-methyl-4-oxo-5-pyridinecarboxylate instead of ethyl 1,4-dihydro-4-oxo-3-propyl-5-pyridinecarboxylate, the title compound was prepared in 88% yield as an orange oil; ¹H NMR (360 MHz, CDCl₃) δ1.41 (3H, t, J 7.1 Hz), 2.35 (3H, s), 4.43 (2H, q, J 7.1 Hz), 7.07 (2H, d, J 8.4 Hz), 7.63 (2H, d, J 8.3 Hz), 8.86 (1H, s); MS (ES⁺) m/z 354/356/358 [MH]⁺.

c) 7-(4-Bromophenyl)-2-(4-chlorophenyl)-2,5-dihydro-6-methyl-pyrazolo[4,3-c]pyridin-3-one hydrochloride Following a similar procedure to that described in Example 4, except using ethyl 3-(4-bromophenyl)-4-chloro-2-methyl-5-pyridinecarboxylate instead of ethyl 4-chloro-3-propyl-5-pyrdinecarboxylate, the title compound was prepared in 68% yield as a yellow solid; mp 328–335° C. (MeOH-HCl-Et₂O); ¹H NMR (360 MHz, DMSO-d₆) δ2.25 (3H, s), 7.42 (2H, d, J8.8 Hz), 7.49 (2H, d, J8.4 Hz), 7.70 (2H, d, J 8.4 Hz), 8.12 (2H, d, J8.8 Hz), 8.57 (1H, s), 12.56 (1H, br s); MS (ES⁺) m/z 414/416/418[MH]⁺. Anal. found: C, 51.84; H, 2.98; N, 9.26. C₁₉H₁₃BrClN₃O.0.7HCl.0.21CH₃OH requires: C, 51,62; H, 3.28; N, 9.40% d) 2-(4-Chlorophenyl)-2,5-dihydro-6-methyl-7-[4-(pyridin-3-yl)phenyl]-pyrazolo[4,3-c]pyridin-3-one Following a similar procedure to that described in Example 23, except using 7-(4-bromophenyl)-2-(4-chlorophenyl)-2,5-dihydro-6-methyl-pyrazolo[4,3-]pyridin-3-one instead of 2-(4-chlorophenyl)-2,5-dihydro-7-(3-iodophenyl)-6-methylpyrazolo[4,3-c]pyridin-3-one, the title compound was prepared in 75% yield as a yellow solid; mp 308–309° C (CH₂Cl₂-MeOH-EtOAc); ¹H NMR (400 MHz, DMSO-d₆) δ2.31 (3H, s), 7.42 (2H, d, J 9.0 Hz), 7.53 (1H, dd, J 7.9, J'4.8 Hz), 7.67 (2H, d, J 8.2 Hz), 7.88 (2H, d, J 8.2 Hz), 8.14 (2H, d, J 9.0 Hz), 8.19 (1H, d, J 7.8 Hz), 8.59 (1H, s), 8.61 (1H, d, J 4.8 Hz), 9.00 (1H, d, J 1.5 Hz), 12.51 (1H, br d, J 6.6 Hz); MS (ES⁺) m/z 413/415[MH]⁺.

EXAMPLE 30

2-(4-Chlorophenyl)-2,5-dihydro-6-methyl-7-[4-(morpholin-4-yl)phenyl]-pyrazolo[4,3-c]pyridin-3-one A mixture of 7-(4-bromophenyl)-2-(4-chlorophenyl)-2,5-dihydro-6-methylpyrazolo[4,3-c]pyridin-3-one (69.1 mg, 0.167 mmol), morpholine (34.9 ml, 0.400 mmol) and sodium tert-butoxide (61.1 mg, 0.636 mmol) in Ianhydrous DMF (3 ml) was degassed by evaporating the flask under vacuum and refilling with nitrogen several times. Solid (S)-(–)-2,2'-bis(diphenylphosphino)-1,1'-binaphthyl [(S)-BINAP] (10.5 mg, 0.0169 mmol) and tris (dibenzylideneacetone)dipalladium(0) (7.6 mg, 0.0083 mmol) were added and the mixture was stirred at 80° C. under nitrogen for 47 h, adding more (S)-BINAP (10.7 mg, 0.172 mmol) and tris(dibenzylideneacetone)dipalladium(0) (7.9 mg, 0.0086 mmol) after 23 h. The solvent was removed in vacuo and the residue was purified by flash chromatography (silica gel, 3–5% MoOH/CH₂Cl₂) and preparative HPLC (YMCSIL D column, 7% MeOH/1-chlorobutane) to give 17.9 mg (26%) of the title compound; mp 306–315° C. (CH₂Cl₂-MeOH-EtOAc); ¹H NMR (360 MHz, DMSO-d₆) δ2.27 (3H, s), 3.20 (4H, m), 3.77 (4H, m), 7.05 (2H, d, J8.8 Hz), 7.40 (2H, d), 7.42 (2H, d, J8.9 Hz), 8.15 (2H, d, J9.0 Hz), 8.51 (1H, s), 12.35 (1H, br s); MS (ES⁺) m/z 421/423 [MH]⁺. Anal. found: C, 65.57; H, 4.84; N, 13.22. C₂₃H₂₁CIN₄O₂ requires: C, 65.63; H, 5.03; N, 13.31%.

EXAMPLE 31

2-(4-Chlorophenyl)-2,5-dihydro-6-methyl-7-[3-nitrophenyl]pyrazolo[4,3-c]pyridin-3-one a) Ethyl 1,4-dihydro-2-methyl-3-(3-nitrophenyl)-4-oxo-5-pyridinecarboxylate Following a similar procedure to that described in Example 19, Step a, except using 3-nitrophenylacetone (Shtacher, G.; Dayagi, S. *J. Med. Chem.* 1972, 15, 1174) instead of 3-methoxyphenylacetone, the title compound was prepared, by collection of the precipitated solid after leaving the reaction mixture to cool overnight, followed by washing with diethyl ether and drying at 60° C. under vacuum, in 37% yield as a whitish solid; ¹H NMR (250 MHz, CDCl₃) δ1.46 (3H, t, J 7.1 Hz), 2.38 (3H, s), 4.48 (2H, q, J 7.1 Hz), 7.59–7.70 (2H, m), 8.19 (1H, d, J 1.6 Hz), 8.28 (1H, dt, J 7.4, J'2.0 Hz), 8.93 (1H, s), 11.47 (1H, br s); MS (ES⁺) in/z 303[MH]⁺.

b) Ethyl 4-chloro-2-methyl-3-(3-nitrophenyl)-5pyridinecarboxylate

Following a similar procedure to that described in Example 2, Step a, except using ethyl 1,4-dihydro-2-methyl- 3-(3-nitrophenyl)-4-oxo-5-pyridinecarboxylate instead of ethyl 1,4-dihydro-4-oxo-3-propyl-5-pyridinecarboxylate, the title compound was prepared in 79% yield as a brown oil; $^1$H NMR (250 MHz, DMSO-d$_6$) δ1.34 (3H, t, J 7.1 Hz), 2.29 (3H, s), 4.38(2H, q, J 7.1 Hz), 7.84–7.89(2H, m), 8.27(1H, m), 8.35(1H, m), 8.87 (1H, s); MS (ES$^+$) m/z 321/323 MH]$^+$.

c) 2-(4-Chlorophenyl)-2,5-dihydro-6-methyl-7-(3-nitrophenyl)pyrazolo[4, 3-c]pyridin-3-one hydrochloride Following a similar procedure to that described in Example 4, except using ethyl 4-chloro-2-methyl-3-(3-nitrophenyl)-5-pyridinecarboxylate instead of ethyl 4-chloro-3-propyl-5-pyridinecarboxylate, the title compound, after trituration in boiling ethanol, was prepared in 40% yield as a yellow solid; mp 346–348° C.; $^1$H NMR (360 MHz, DMSO-d$_6$) δ2.28 (3H, s), 7.42 (2H, d, J 8.9 Hz), 7.81 (1H, t, J 8.1 Hz), 8.01 (1H, dt, J 7.6, J'1.0 Hz), 8.12 (2H, d, J 9.0 Hz), 8.30 (1H, dt), 8.40 (1H, t, J 1.9 Hz), 8.62 (1H, d), 12.56 (1H, br d, J 5.6 Hz). Anal. found: C, 57.12; H, 3.78; N, 13.82. C$_{19}$H$_{13}$ClN$_4$O$_3$. 0.5HCl requires: C, 57.19; H, 3.41; N, 14.04%.

EXAMPLE 32

7-(3-Aminophenyl)-2-(4-chlorophenyl)-2,5-dihydro-6-methylyvrazolo[4,3-c]pyridin-3-one To a stirred preformed mixture of copper(II) acetylacetonate (0.577 g, 2.20 mmol) and sodium borohydride (2.00 g, 52.9 mmol) in ethanol (550 ml) was added 2-(4-chlorophenyl)-2,5-dihydro-6-methyl-7-(3-nitrophenyl)-pyrazolo[4,3-c]pyridin-3-one (4.60 g, 11.0 mmol) and the solution was heated at 60° C. for 20 min, then stirred at room temperature for 1.5 h. The solvent was removed in vacuo and the residue was purified by flash chromatography (silica gel, 5–20% MeOH/CH$_2$Cl$_2$) to afford 3.61 g (94%) of the title compound as a yellow solid; mp 338–342° C. (CH$_2$Cl$_2$-MeOH-EtOAc); $^1$H NMR (360 MHz, DMSO-d$_6$) δ2.23 (3H, s), 5.14 (2H, br s), 6.56 (1H, d, J 7.5 Hz), 6.61 (1H, d, J 8.0 Hz), 6.67 (1H, s), 7.12 (1H, t, J 7.8 Hz), 7.42 (2H, d, J 9.0 Hz), 8.14 (2H, d, J 9.0 Hz), 8.52 (1H, s), 12.38 (1H, br s); MS (ES$^+$) m/z 351/353[MH]$^+$. Anal. found: C, 63.18; H, 4.19; N, 15.20. C$_{19}$H$_{15}$ClN$_4$O.0.6H$_2$O requires: C, 63.11; H, 4.52; N, 15.49%.

EXAMPLE 33

2-(4-Chlorophenyl)-2,5-dihydro-6-methyl-7-[3-(3-pyridylmethylamino)phenyl]pyrazolo [4,3-c]pyridin-3-one To a stirred mixture of 7-(3-aminophenyl)-2-(4-chlorophenyl)-2,5-dihydro-6-methylpyrazolo[4,3-c]pyridin-3-one (0.100 g, 0.285 mmol), 3-pyridinecarboxaldehyde (32.3 ml, 0.342 mmol), and acetic acid (65.5 ml, 1.14 mmol) in anhydrous methanol (4 ml) under nitrogen was added sodium cyanoborohydride (21.5 mg, 0.342 mmol) and the mixture was stirred for 3 h. The mixture was quenched with saturated aqueous K$_2$CO$_3$ (0.5 ml) and the solvent was removed in vacuo. The residue was purified by flash chromatography (silica gel, 5–10% MeOH/CH$_2$Cl$_2$) to give 0.1162 g (93%) of the title compound as a yellow solid; mp 284–287° C. (CH$_2$Cl$_2$ -MeOH-EtOAc); $^1$H NMR (360 MHz, DMSO-d$_6$) δ2.13 (3H, s), 4.34 (2H, d, J 6.1 Hz), 6.39 (1H, t, J 6.1 Hz), 6.64–6.68 (3H, m), 7.17 (1H, t, J 7.7 Hz), 7.35 (1H, dd, J 7.9, J'4.9 Hz), 7.42 (2H, d, J9.0 Hz), 7.77 (1H, dt), 8.11 (2H, d, J 9.0 Hz), 8.44 (1H, m), 8.51 (1H, s), 8.61 (1H, s), 12.34 (1H, br s); MS (ES$^+$) m/z 442/444[MH]$^+$, 221/222[(M2H)/2]$^+$. Anal. found: C, 67.08; H, 4.50; N, 15.54. C$_{25}$H$_{20}$ClN$_5$O.0.3H$_2$O requires: C, 67.13; H, 4.64; N, 15.66%.

EXAMPLE 34

2-(4-Chlorophenyl)-2,5-dihydro-6-methyl-7-[3-(dimethylamino)phenyl-pyrazolo[4,3-c]pyridin-3-one To a stirred mixture of 7-(3-aminophenyl)-2-(4-chlorophenyl)-2,5-dihydro-6-methylpyrazolo[4,3-c]pyridin-3-one (0.100 g, 0.285 mmol), formaldehyde (51.4 ml, 0.686 mmol), and acetic acid (65.5 ml, 1.14 mmol) in anhydrous methanol (4 ml) under nitrogen was added sodium cyanoborohydride (42.9 mg, 0.684 mmol) and the mixture was stirred for 7 h. More formaldehyde (50 ml, 0.667 mmol), sodium cyanoborohydride (40 mg, 0.637 mmol), acetic acid (65 ml, 1.14 mmol) and some dichloromethane was added and the mixture was heated to 50° C. for 1 h. The mixture was quenched with saturated aqueous K$_2$CO$_3$ (0.5 ml) and the solvent was removed in vacuo. The residue was purified by flash chromatography (silica gel, 3–5% MeOH/CH$_2$Cl$_2$) to give 0.0905 g (84%) of the title compound as a yellow solid; mp 268–272° C. (CH$_2$Cl$_2$-MeOH-EtOAc); $^1$H NMR (360 MHz, DMSO-d$_6$) δ2.26 (3H, s), 2.93 (6H, s), 6.73–6.78 (2H, m), 6.84 (1H, m), 7.29 (1H, t, J 7.8 Hz), 7.42 (2H, d, J 9.0 Hz), 8.14 (2H, d, J 9.0 Hz), 8.54 (1H, s), 12.40 (1H, br s); MS (ES$^+$) m/z 379/381 [MH]$^+$, 190/191[(M$^+$2H)/2]$^+$. Anal. found: C, 65.91; H, 4.93; N, 14.70. C$_{21}$H$_{19}$ClN$_4$O.0.2H$_2$O requires; C, 65.95; H, 5.11; N, 14.65%

EXAMPLE 35

N-{3-[2-(4-Chlorophenyl)-3, 5-dihydro-6-methyl-3-oxo-2H-pyrazolo[4,3-c]pyridin-7-yl] phenyl}methanesulphonamide To a stirred solution of 7-(3-aminophenyl)-2-(4-chlorophenyl)-2,5-dihydro-6-methylpyrazolo[4,3-c]pyridin-3-one (0.100 g, 0.285 mmol) in anhydrous ethylene glycol, dimethyl ether (5 ml) was added portionwise, over a few hours, pyridine (0.228 ml, 2.82 mmol) and methanesulphonyl chloride (0.174 ml, 2.25 mmol), and the mixture was heated at 50° C. for 1.5 h. The solvent was removed in vacuo and the residue was purified by flash chromatography (silica gel, 5–10% MeOH/CH$_2$Cl$_2$) to leave 0.1119 g (92%) of the title compound as a yellow solid; mp 332–341° C. (CH$_2$Cl$_2$-MeOH-EtOAc); $^1$H NMR (360 MHz, DMSO-d$_6$) δ2.28 (3H, s), 3.06 (3H, s), 7.24 (2H, dd, J 7.9, J'1.8 Hz), 7.40 (1H, m), 7.43 (2H, d, J 9.0 Hz), 7.46 (1H, t, J 8.0 Hz), 8.13 (2H, d, J 9.0 Hz), 8.56 (1H, s); MS (ES$^+$) m/z 429/431[MH]$^+$. Anal. found: C, 55.89; H, 4.06; N, 12.60. C$_{20}$H$_{17}$CLN$_4$O$_3$S.0.2H$_2$O requires: C, 55.54; H, 4.06; N, 12.95%.

EXAMPLE 36

2-(4-Chlorophenyl)-2,5-dihydro-6-methyl-7-[3-(4H-1,2, 4-triazol-4-yl)phenyl]pyrazolo [4,3-c]pyridin-3-one A mixture of 7-(3-aminophenyl)-2-(4-chlorophenyl)-2,5-dihydro-6-methylpyrazolo[4,3-c]pyridin-3-one (0.100 g, 0.285 mmol), N,N-dimethylformamide azine (Bartlett, R. K.; Humphrey, I. R. *J. Chemn. Soc. C* 1967, 1664) (41.3 mg, 0.290 mmol), and p-toluenesulfonic acid (10 mg, 0.053 mmol) in toluene (4 ml) was heated at reflux under nitrogen for 7 days, adding more p-toluenesulfonic acid (10 mg, 0.053 mmol) and some DMSO after 1 day. The solvents were removed in vacuo and the residue was purified by flash chromatography (silica gel, 5–15% MeOH/CH$_2$Cl$_2$), then trituration in hot MeOH-CH$_2$Cl$_2$, to leave 0.0436 g (38%) of the title compound as a yellow solid; mp >350° C.; $^1$H NMR (360 MHz, DMSO-d$_6$) δ2.29 (3H, s), 7.41 (2H, d, J 9.1 Hz), 7.59 (1H, d, J 7.7 Hz), 7.70 (1H, t, J 7.7 Hz), 7.79 (1H, dd), 7.87 (1H, fine t), 8.11 (2H, d, J 8.9 Hz), 8.62 (1H, s), 9.18 (2H, s), 12.52 (1H, br s); MS (ES$^+$) m/z 403/405 1MH]$^+$. Anal. found: C, 61.14; H, 3.79; N, 20.29. C$_{21}$H$_{15}$ClN$_6$O.0.5H$_2$O requires: C, 61.24; H, 3.92; N, 20.41%.

EXAMPLE 37

N-{3-[2-(4-Chloronhenyl)-3,5-dihydro-6-methyl-3-oxo-2H-pyrazolo[4 3-c]pyridin-7-yl]phenyl}-N'-(ethyl)urea To a stirred solution of 7-(3-aminophenyl)-2-(4-chlorophenyl)-2,5-dihydro-6-methylpyrazolo[4,3-c]pyridin-3-one (0.0902 g, 0.257 mmol) in anhydrous THF (5 ml), under nitrogen, was added dropwise ethyl isocyanate (22.2 ml, 0.283 mmol) and the solution was stirred at 60° C. for 3 days, adding more ethyl isocyanate (22.2 ml, 0.283 mmol) after 1 and 2 days. The mixture was filtered, and the collected solid was washed with ethyl acetate and dried at 60° C. under vacuum to leave 88.7 mg (82%) of the title compound as a yellow solid; mp 299–305° C. (CH$_2$Cl$_2$-MeOH-EtOAc); $^1$H NMR (360 MHz, DMSO-d$_6$) δ1.05 (3H, t, J 7.2 Hz), 2.24 (3H, s), 3.10 (2H, quintet, J 7.1 Hz), 6.10 (1H, t, J 5.6 Hz), 6.99 (1H, d, J 7.6 Hz), 7.33 (1H, t, J 7.7 Hz), 7.42 (2H, d, J 9.1 Hz), 7.45 (1H, m), 7.51 (1H, fine t), 8.13 (2H, d, J8.9 Hz), 8.51 (1H, s), 8.54 (1H, s), 12.40 (1H, br s); MS (ES$^+$) m/z 422/424[MH]$^+$. Anal. found: C, 61.67; H, 4.55; N, 16.33. C$_{22}$H$_{20}$ClN$_5$O$_2$.0.3H$_2$O requires: C, 61.84; H, 4.86; N, 16.39%.

EXAMPLE 38

2-(4-Chlorophenyl)-2 5-dihydro-6-methyl -7-[3-(4-methylpiperazin-1-yl)phenyl]pyrazolo[4,3-c]pyridin-3-one A stirred mixture of 7-(3-aminophenyl)-2-(4-chlorophenyl)-2,5-dihydro-6-methylpyrazolo[4,3-c]pyridin-3-one (0.1997 g, 0.570 mmol), and mechlorethamine hydrochloride (0.1293 g, 0.672 mmol) in anhydrous 1-butanol (4 ml) was heated at reflux under nitrogen for 50 h, adding sodium carbonate (24.7 mg, 0.233 mmol) after 22 h and more mechlorethamine hydrochloride (0.4807 g, 2.50 mmol) after 26 h. The solvent was removed in vacuo and the residue was purified by flash chromatography [silica gel, 5–30% MeOH/CH$_2$Cl$_2$; then silica gel, CH$_2$Cl$_2$-MeOH-NH$_3$ (95:5:0.5 to 93:7:0.7)], to afford 29.6 mg (12%) of the title compound as a yellow solid; mp 191–210° C. (CH$_2$Cl$_2$-EtOAc-hexane); $^1$H NMR (360 MHz, DMSO-d$_6$) δ2.25 (3H, s), 2.26 (3H, s), 2.50 (4H, m), 3.20 (4H, m), 6.89 (1H, d, J 7.5 Hz), 6.99 (1H, m), 7.05 (1H, s), 7.33 (1H, t, J 7.9 Hz), 7.42 (2H, d, J9.0 Hz), 8.13 (2H, d, J8.9 Hz), 8.54 (1H, s), 12.44 (1H, br s); MS (ES$^+$) m/z 434/436[MH]$^+$, 218[(M+2H)/]$^+$. Anal. found: C, 64.41; H, 5.63; N, 15.44. C$_{24}$H$_{24}$ClN$_5$O.0.7H$_2$O requires: C, 64.56; H, 5.73; N, 15.68%.

EXAMPLE 39

2,5-Dihydro-2-phenyl-7-(4-pyridyl)pyrazolo[4,3-c]pyridin-3-one

The title compound was prepared from ethyl 4-(4-pyridyl)acetoacetate according to the method of Example 1, isolated as a red solid hydrochloride salt. MS (ES$^+$) m/z 323/325 [MH]$^+$. Anal. found: C, 52.68; H, 3.86; N, 14.21. C$_{17}$H$_{11}$N$_4$OCl.HCl.1.5H$_2$O requires: C, 52.87; H, 3.91; N, 14.51%.

EXAMPLE 40

7-(4-Aminophenyl)-2-(4-chlorophenyl)-2,5-dihydro-6-methylpyrazolo[4,3-c]pyridin-3-one a) Ethyl 1,4-dihydro-2-methyl-3-(4-nitrophenyl)-4-oxo-5-pyridinecarboxylate To the product of Example 9(a) (15.6 g) was added 4-nitrophenylacetone (15 g) and dry methylene chloride (120 ml). Phosphorus pentoxide (24 g) was then added with stirring, and the mixture was stirred under an atmosphere of dry nitrogen for 18 hours. The solids were separated by filtration and washed with dry methylene chloride (100 ml). The combined filtrates were evaporated, and Dowtherm® A (100 ml) was added to the residue. The resulting mixture was heated rapidly to reflux under an atmosphere of dry nitrogen for 0.17 h. Upon cooling to room temperature, and allowing to age, the title compound crystallised, was collected by filtration, washed with diethyl ether, and dried in vacuo. Yield 9.5 g. $^1$H NMR (360 MHz, DMSO-d$_6$) δ12.15 (1H, br s), 8.42 (2H, d, J 8.6 Hz), 7.68 (2H, d, J 8.6 Hz), 4.36 (2H, q, J 6.8 Hz), 2.28 (3H, s), 1.43 (3H, t, J 7.2 Hz); MS (ES$^+$) m/z 303[MH]$^+$.

b) Ethyl 4-chloro-2-methyl-3-(4-nitrophenyl)-5-pyridinecarboxylate

To the product of Example 40(a) (9.5g, 31.45 mmol) was added phosphorus oxychloride (100 ml), and the mixture was heated at reflux for 2 h under an atmosphere of dry nitrogen. The volatiles were removed in vacuo and the residue was azeotroped with toluene. The residue was cooled in an ice bath, and quenched by cautious addition of saturated aqueous NaHCO$_3$ (100 ml). The aqueous layer was extracted with dichloromethane (3×100 ml), and the combined organic extracts were dried (Na$_2$SO$_4$) and evaporated in vacuo. The residue was purified by flash chromatography (silica gel, 25% ethyl acetate/dichloromethane) to yield 8.77 g (87%) of the title compound as a yellow solid; $^1$H NMR (360 MHz, CDCl$_3$) 67 8.93 (1H, s), 8.37 (2H, d, J 8.7 Hz), 7.40 (2H, d, J 8.7 Hz), 4.45 (2H, q, J 7.1 Hz), 2.35 (3H, s), 1.42 (3H, t, J 7.2 Hz); MS (ES$^+$) m/z 321/323[MH$^+$.

c) 2-(4-Chlorophenyl)-2,5-dihydro-6-methyl-7-(4-nitrophenyl]pyrazolo[4,3-c]pyridin-3-one The product of Example 40(b) (5.08 g, 15.8 mmol) and 4-chlorophenylhydrazine hydrochloride (3.50 g) in anhydrous 1-butanol (180 ml) was stirred at reflux under nitrogen for 4 hours. The mixture was then allowed to cool to room temperature, and allowed to age for 18 h. The orange solid was then collected by filtration, washed with ethanol, and dried in vacuo to give 4.01 g (67%) of the title compound as an orange solid; $^1$H NMR (360 MHz, DMSO-d$_6$) 67 12.57 (1H, br d, J 7.2 Hz), 8.60 (1H, d, J 7.2 Hz), 8.33 (2H, d, J 8.8 Hz), 8.10 (2H, d, J 8.8 Hz), 7.82 (2H, d, J 9.0 Hz), 7.40 (2H, d, J 9.0 Hz), 2.26 (3H, s); MS (ES$^+$) m/z 381/383 [MH]$^+$. Anal. found: C, 59.93; H, 3.44; N, 14.71. C$_{19}$H$_{13}$N$_4$O$_3$Cl requires: C, 59.96; H, 3.47; N, 14.40%.

d) 7-(4-Aminophenyl)-2-(4-chlorophenyl)-2 5-dihydro-6-methyl-pyrazolol[4, 3-c]pyridin-3-one The product of Example 40(c) (1.75 g, 4.6 mmol) was added as a solid to a pre-formed mixture of copper(II) acetylacetonate (0.356 g, 0.92 mmol), ethanol (70 ml) and sodium borohydride (0.521 g). The mixture was then warmed briefly to give a dark red solution, then stirred at room temperature for 1 h. The solvent was then evaporated

EXAMPLE 41

7-(4-Acetamidophenyl)-2-(4-chlorophenyl)-2,5-dihydro-6-methyl-pyrazolo[4,3-c]pyridin-3-one To the product of Example 40(d) (0.102 g, 0.29 mmol) in dry pyridine (1 ml) was added acetyl chloride (0.035 ml). The mixture was warmed briefly to give a homogeneous solution, and then stirred at room temperature for 18 h. The mixture was diluted with excess aqueous sodium hydrogencarbonate, and the yellow solid collected by filtration, washed with water, and then diethyl ether. The resulting solid was boiled in ethanol (4 ml), then allowed to stand at room temperature. The yellow solid was collected by filtration and dried in vacuo to afford 0.077 g (68%) of the title compound; $^1$H NMR (360 MHz, DMSO-$d_6$) 67 12.42 (1H, br s), 10.05 (1H, s), 8.54 (1H, s), 8.13 (2H, d, J 9.0 Hz), 7.68 (2H, d, J 8.5 Hz), 7.43 (4H, m), 2.26 (3H, s), 2.09 (3H, s); MS (ES$^+$) m/z 393/395[MH]$^+$. Anal. found: C, 60.06; H, 4.78; N, 12.95. $C_{21}H_{17}N_4O_2Cl.1.5H_2O$ requires: C, 60.07; H, 4.80; N, 13.34%.

EXAMPLE 42

7-[4-(4-(tert-Butoxycarbonyl)piperazin-1-yl)phenyl]-2-(4-chlorophenyl)-2,5-dihydro-6-methylpyrazolo[4.3-c]pyridin-3-one To the product of Example 40(d) (0.329 g, 0.94 mmol) and bis(2-chloroethyl)amine hydrochloride (0.208 g) was added dry dimethylformamide (2 ml) and water (1 ml). The mixture was then heated at 95° C., with stirring, under nitrogen for 24 h. The mixture was then allowed to cool to room temperature, and di-tert-butyldicarbonate (0.80 g) and solid sodium hydrogencarbonate (1.0 g) were added. The mixture was then stirred at room temperature for 18 h. The solvent was stripped at reduced pressure, and the residue was purified by flash chromatography (silica gel, 5% methanol/dichloromethane) to yield 0.1 g (20%) of the title compound, after recrystallisation from hot toluene, as a yellow solid; MS (ES$^+$) 7?m/z 520/522 NH]$^+$.

EXAMPLE 43

2-(4-Chlorophenyl)-2,5-dihydro-6-methyl-7-[4-(piperazin-1-yl)phenyl]-pyrazolo[4,3-c]pyridin-3-one bis(hydrochloride)

To the product of Example 42 (0.042 g, 0.08 mmol) was added a saturated solution of hydrogen chloride in methanol, and the resulting solution was allowed to age for 18 h. The solvent was then evaporated, and the residue was azeotroped with toluene. The residue was crystallised from methanol-ethyl acetate, and recrystallised from hot ethanol to afford the title compound as a yellow solid; $^1$H NMR (500 MHz, DMSO-$d_6$) 67 12.47 (br s), 9.05 (br s), 8.52 (1H, s), 8.14 (2H, d, J 9.0 Hz), 7.43 (4H, m), 7.10 (2H, d, J8.8 Hz), 3.46 (4H, m), 3.26 (4H, m), 2.28 (3H, s); MS (ES$^+$) m/z 420/422[MH]$^+$.

EXAMPLE 44

2-(4-Chlorophenyl)-2,5-dihydro-6-methyl-7-[4-(pyrrolidin-2-on-1-yl)phenyl]pyrazolo[4,3-c]pyridin-3-one 4-Chlorobutyryl chloride (0.36 ml) was dissolved in dichloromethane (10 ml), and 1.5 ml of the resulting solution was added to the product of Example 40(d) (0.102 g, 0.29 mmol). To the mixture was then added pyridine (0.3 ml). The reaction mixture was then stirred for 1 h at room temperature. A precipitate formed which was redissolved by the addition of dry dimethylformamide (1 ml). The reaction mixture was then diluted with toluene (20 ml), and solvents stripped at reduced pressure. The residue was redissolved in dry dimethylformamide (2 ml), and sodium hydride (0.057 g of a 60% dispersion in oil) was added, and the resulting mixture stirred at room temperature for 0.5 h. The reaction mixture was then diluted with water (20 ml), and dichloromethane (20 ml), stirred vigorously briefly, then allowed to stand. The solid was collected by filtration, and washed with water, then diethyl ether. The solid was then suspended in boiling ethanol, allowed to cool to room temperature, and the solid collected by filtration and dried in vacuo, to afford 0.066 g (54%) of the title compound; $^1$H NMR (360 MHz, DMSO-$d_6$) 67 12.44 (1H, br s), 8.55 (1H, s), 8.13 (2H, d, J 9.0 Hz), 7.78 (2H, d, J 8.7 Hz), 7.52 (2H, d, J 8.6 Hz), 7.42 (2H, d, J8.9 Hz), 3.91 (2H, m), 2.54 (2H, m), 2.27 (3H, s), 2.10 (2H, m); MS (ES$^+$) m/z 419/421[MH]$^+$. Anal. found: C, 62.80; H, 4.75; N, 12.27. $C_{23}H_{19}N_4O_2Cl.1.25H_2O$ requires; C, 62.58; H, 4.91; N, 12.69%.

EXAMPLE 45

7-[4-(2-Amino-2-methylpropionamido)phenyl]-2-(4-chlorophenyl)-2,5-dihydro-6-methylnyrazolo[4 3-c]pyridin-3-one To N-tert-butoxycarbonyl α-methylalanine (3.5 g) was added thionyl chloride (40 ml) and catalytic dry dimethylformamide (3 drops). The mixture was then stirred at room temperature for 4 h. The thionyl chloride was then evaporated at reduced pressure, and the residue azeotroped with toluene and evaporated at reduced pressure. To the residue was added dry dichloromethane (17 ml). A portion of this mixture (3 ml) was then added to the product of Example 40(d) (0.10 g, 0.28 mmol) and the mixture was stirred at room temperature under nitrogen for 5 h. Methanol (10 ml) was added, and the mixture was then poured into aqueous sodium carbonate. The organic phase was separated, and the aqueous phase extracted with dichloromethane. The combined organic phases were evaporated at reduced pressure, and the residue was purified by flash chromatography (silica gel, 10% methanol/dichloromethane) to yield the title compound, (0.02 g, 16%) after crystallisation from hot ethyl acetate, as a yellow solid; $^1$H NMR (500 MHz, DMSO-$d_6$), 8 8.54 (1H, s), 8.13 (2H, d, J9 Hz), 7.78 (2H, d, J8.5 Hz), 7.46 (2H, d, J8.5 Hz), 7.42 (2H, d, J 9 Hz), 3.32 (2H, s), 2.27 (3H, s), 1.35 (6H, s); MS (ES$^+$) m/z 436/438[MH]$^+$.

EXAMPLE 46

2-(4-Chlorophenyl)-2,5-dihydro-6-methyl-7-f4-(4-methylpiperazin-1-yl)phenylipyrazolo[4, 3-c]pyridin-3-one To the product of Example 40(d) (0.106 g, 0.30 mmol) and mechlorethamine hydrochloride (0.10 g) was added dry ethanol (2 ml). The mixture was then heated at reflux, with stirring, under nitrogen for 18 h. Further mechlorethamine hydrochloride (0.10 g) was added, and heating at reflux continued for a further 24 h. The mixture was then allowed to cool to room temperature and diluted with dichloromethane (20 ml) and washed with aqueous sodium hydrogencarbonate (10 ml). The organic phase was separated, evaporated at reduced pressure, and the residue was purified by thin layer chromatography (silica gel, 10% methanol/dichloromethane) to yield 0.01 g (8%) of the title compound, after recrystallisation from hot ethyl acetate, as a yellow solid; $^1$H NMR (500 MHz, DMSO-$d_6$), 8 12.4 (1H, br s), 8.51 (1H, s), 8.15 (2H, d, J 9 Hz), 7.42 (2H, d, J 8.5 Hz), 7.38 (2H, d, J 8.5 Hz), 7.04 (2H, d, J 9 Hz), 3.24 (4H, m), 2.53 (4H, m), 2.27 (6H, s); MS (ES$^+$) m/z 434/436[MH]$^+$.

EXAMPLE 47

7-f4-(N'tert-Butoxycarbonylglycinamido)phenyl]-2-(4-chloronhenyl)-2, 5-dihydro-6-methylpyrazolo[4,3-cl pyridin-3-one To N-tert-butoxycarbonylglycine (1.2 g) and 1-hydroxybenzotriazole (0.93 g) in dry dimethylformamide (7 ml), under nitrogen, was added with stirring 1-(3-dimethylaminopropyl)-3-ethylcarbodiumide hydrochloride (1.32 g). The mixture was stirred at room temperature for 1 h, then the product of Example 40(d) (1.00 g, 2.85 mmol) was added. The mixture was stirred at room temperature for 3 h, then diluted with water (100 ml), and the resulting yellow solid recovered by filtration, washed with water and ethyl acetate, and dried in vacuo to yield 1.18 g (82%) of the title compound, as a yellow solid; $^1$H NMR (360 MHz, DMSO-$d_6$) δ12.43 (1H, br s), 10.05 (1H, br s), 8.54 (1H, s), 8.14 (2H, d, J 9.0 Hz), 7.69 (2H, d, J 8.5 Hz), 7.46 (2H, d, J 8.5 Hz), 7.42 (2H, d, J 9.0 Hz), 7.08 (1H, m), 3.76 (2H, d, J 6.0 Hz), 2.27 (3H, s), 1.41 (9H, s); MS (ES$^+$) m/z 508/510 [MH]$^+$.

EXAMPLE 48

2-(4-Chlorophenyl)-2, 5-dihydro-6-methyl-7-[4-(1,2, 4-triazol-4-yl)phenyl]-pyrazolo[4, 3-c]pyridin-3-one To the product of Example 40(d) (0.153 g, 0.436 mmol) was added dimethylformamide azine (0.062 g), p-toluenesulfonic acid (0.005 g), toluene (3 ml), and dry dimethylsulfoxide (1 ml). The mixture was then heated at reflux, with stirring, under nitrogen for 24 h. Further portions of dimethylformamide azine (0.062 g) and p-toluenesulfonic acid (0.005 g) were then added, and heating at reflux was continued for a further 48 h. The mixture was then allowed to cool to room temperature, the solvent was removed at reduced pressure, and the residue was purified by flash chromatography (silica gel, 10% methanol/dichloromethane) to yield 0.065 g (37%) of the title compound, after recrystallisation from hot methanol/ethyl acetate, as a yellow solid; $^1$H NMR (360 MHz, DMSO-$d_6$) δ12.53 (1H, br s), 9.22 (1H, s), 8.60 (1H, br s), 8.13 (2H, d, J 9.0 Hz), 7.85 (2H, d, J 8.6 Hz), 7.73 (2H, d, J 8.6 Hz), 7.43 (2H, d, J 9.0 Hz), 2.30 (3H, s); MS (ES$^+$) m/z 403/405[MH]$^+$.

EXAMPLE 49

2-(4-Chlorophenyl)-7-(4-cyanophenyl)-2. 5-dihydro-6-methylpyrazolo[4,3-c]pyridin-3-one a) Ethyl 3-(4-cyanophenyl)-1.4-dihydro-2-methyl-4-oxo-5-pyridinecarboxylate To the product of Example 9a (4.59 g) was added 4-cyanophenylacetone (prepared according to the procedure described in J. Org. Chem., 1985, 50, 1373–1381) (3.55 g) and dry CH$_2$Cl$_2$ (10 ml). Phosphorus pentoxide (1 g) was then added with stirring, and the mixture was stirred under an atmosphere of dry nitrogen for 18 hours. The solids were separated by filtration and washed with dry methylene chloride (10 ml). The combined filtrates were evaporated, and Dowtherm® A (20 ml) was added to the residue. The resulting mixture was heated rapidly to reflux under an atmosphere of dry nitrogen for 0.17 hours. Upon cooling to room temperature, and allowing to age, the title compound crystallised, was collected by filtration, washed with diethyl ether, and dried in vacuo, to give a cream coloured solid (1.71 g). $^1$H NMR (250 MHz, DMSO-$d_6$) δ11.44 (1H, br s), 8.91 (1H, s), 7.73 (2H, d, J 8.6 Hz), 7.40 (2H, d, J 8.6 Hz), 4.47 (2H, q, J 6.8 Hz), 2.35 (3H, s), 1.46 (3H, t, J 7.2 Hz).

b) Ethyl 4-chloro-3-(4-cyanophenyl)-2-methyl-5-pyridinecarboxylate To the product of Example 49a (1.7 g, 6.0 mmol) was added phosphorus oxychloride (40 ml), and the mixture was heated at reflux for 2 h under an atmosphere of dry nitrogen. The volatiles were removed in vacuo and the residue was azeotroped with toluene. The residue was cooled in an ice bath, and quenched by cautious addition of saturated aqueous NaHCO$_3$ (60 ml). The aqueous layer was extracted with CH$_2$Cl$_2$ (3×40 ml), and the combined organic extracts were dried (Na$_2$SO$_4$) and evaporated ill vacuo. The residue was purified by flash chromatography (silica gel, eluent 10% ethyl acetate/CH2Cl2) to yield 1.62 g of the title compound as a pale yellow solid; $^1$H NMR (250 MHz, CDCl$_3$) 6 8.92 (1H, s), 7.80 (2H, d, J 8.7 Hz), 7.33 (2H, d, J 8.7 Hz), 4.44 (2H, q, J 7.1 Hz), 2.34 (3H, s), 1.42 (3H, t, J 7.2 Hz); MS (ES$^+$) m/z 301/303[MH]$^+$.

c) 2-(4-Chlorophenyl)-7-(4-cyanophenyl)-2,5-dihydro-6-methylpyrazolo[4,3-c]pyridin-3-one The product of Example 49b (1.60 g, 5.32 mmol) and 4-chlorophenylhydrazine hydrochloride (1.14 g; 6.38 mmol) in anhydrous 1-butanol (50 ml) was stirred at reflux under nitrogen for 4 hours. The mixture was then allowed to cool to room temperature, and allowed to age for 18 hours. The orange solid was then collected by filtration, washed with ethanol, and dried in vacuo to give 1.4 g (72%) of the title compound as an orange solid; 1H NMR (360 MHz, DMSO-$d_6$) δ12.54 (1H, br d, J 5.2 Hz), 8.60 (1H, d, J 7.2 Hz), 8.11 (2H, d, J 8.8 Hz), 7.96 (2H, d, J 8.8 Hz), 7.75 (2H, d, J 9.0 Hz), 7.41 (2H, d, J 9.0 Hz), 2.26 (3H, s); MS (ES$^+$) m/z 361/363[MH]$^+$. Anal. found: C, 66.33; H, 3.63; N, 15.23. Cl$_9$Hl$_3$N$_4$O$_3$Cl requires: C, 66.58; H, 3.51; N, 15.53%.

EXAMPLE 50

7-(3-Cyanophenyl)-2-(4-chlorophenyl)-2,5-dihydro-6-methylnyrazolo[4,3-c]pyridin-3-one a) Ethyl 3-(3-cyanophenyl)-1,4-dihydro-2-methyl-4-oxo-5-pyridinecarboxylate Following a similar procedure to that described in Example 49a, except using 3-cyanophenylacetone (prepared by an analogous procedure to that described in J. Org. Chem., 1985, 50, 1373–1381) instead of 4-cyanophenylacetone, the title compound was prepared as a brown solid. $^1$H NMR (250 MHz, DMSO-dc) 611.43 (1H, br s), 8.91 (1H, s), 7.59 (4H, m), 4.45 (2H, q, J 6.8 Hz), 2.35 (3H, s), 1.40 (3H, t, J 7.2 Hz); MS (ES$^+$) m/z 283[MH]$^+$.

b) Ethyl 4-chloro-3-(3-cyanophenyl)-2-methyl-5-pyridinecarboxylate

Following a similar procedure to that described in Example 49b, except using ethyl 3-(3-cyanophenyl)-1,4-dihydro-2-methyl-4-oxo-5-pyridinecarboxylate instead of using ethyl 3-(4-cyanophenyl)-1,4-dihydro-2-methyl-4-oxo-5-pyridinecarboxylate, the title compound was produced as a pale yellow solid. $^1$H NMR (360 MHz, CDCl$_3$) δ8.91 (1H, s), 7.75 (1H, d, J 8.7 Hz), 7.63 (1H, dd, J 8.7, 8.7 Hz), 7.52 (1H, s), 7.45 (1H, d, J 8.7 Hz), 4.44 (2H, q, J 7.1 Hz), 2.34 (3H, s), 1.42 (3H, t, J 7.2 Hz); MS (ES$^+$) m/z 301/303[MH]$^+$.

c) 7-(3-Cyanophenyl)-2-(4-chlorophenyl)-2,5-dihydro-6-methylpyrazolo[4,3-c]pyridin-3-one Following a similar procedure to that described in Example 49c, except using ethyl 4-chloro-3-(3-cyanophenyl)-2-methyl-5-pyridinecarboxylate instead of using ethyl 4-chloro-3-(4-cyanophenyl)-2-methyl-5-pyridinecarboxylate, the title compound was produced as a pale yellow solid. $^1$H NMR (360 MHz, DMSO-d$_6$) δ12.52 (1H, s), 8.91 (1H, s), 8.12 (2H, d, J8.8 Hz), 8.10 (1H, s), 7.91 (2H, m), 7.72 (1H, dd, J8.7, 8.7 Hz), 7.42 (2H, d, J8.7 Hz), 2.25 (3H, s); MS (ES$^+$) m/z 361/363[MH]$^+$. Anal. found: C, 63.47; H, 3.81; N, 14.38. C$_{20}$H$_{13}$N$_4$O C1.0.5HCl requires: C, 63.31; H, 3.58; N, 14.66%.

EXAMPLE 51

2-(4-Chlorophenyl)-2,5-dihydro-6-methyl-7-[4-(pyridin-2-ylmethylamino)-phenyl]pyrazolo[4,3-c]pyridin-3-one To a stirred mixture of 7-(4-aminophenyl)-2-(4-chlorophenyl)-2,5-dihydro-6-methylpyrazolo[4,3-c]pyridin-3-one (0.150 g, 0.43 mmol), 2-pyridinecarboxaldehyde (81 μl, 0.85 mmol) and acetic acid (18 μl, 0.31 mmol) in anhydrous MeOH (3 ml) under nitrogen was added sodium cyanoborohydride (0.02 g, 0.32 mmol) and the mixture was stirred for 24 h. The mixture was quenched with saturated aqueous K$_2$CO$_3$ (0.5 ml) and the solvent was removed in vacuo. The residue was purified by flash chromatography (silica gel, 5–10% MeOH/CH$_2$Cl$_2$) to give 0.076 g (39.7%) of the title compound as a yellow solid; $^1$H NMR (360 MHz, DMSO-d$_6$) δ12.32 (1H, br s), 8.57 (1H, d, J 2.1 Hz), 8.47 (1H, s), 8.14 (2H, d, J 8.7 Hz), 7.77 (1H, t, J 7.5 Hz), 7.43 (3H, m), 7.25 (3H, m), 6.68 (2H, d, J 8.3 Hz), 6.56 (2H, t, J 2.5 Hz), 4.41 (2H, d, J 5.8 Hz), 2.26 (3H, s); MS (ES$^+$) m/z 442/444 [MH]$^+$, 221/222 [(M+2H)/2]$^+$.

EXAMPLE 52

2-(4-Chlorophenyl)-7-[4-(N,N-di(cyclopropylmethyl)amino)phenyl-2,5-dihydro-6-methylpyrazolo[4,3-c]pyridin-3-one To a stirred mixture of 7-(4-aminophenyl)-2-(4-chlorophenyl)-2,5-dihydro-6-methylpyrazolo[4,3-c]pyridin-3-one (0.150 g, 0.43 mmol), cyclopropane carboxaldehyde (80 μl, 1 mmol) and acetic acid (30 μl, 0.52 mmol) in anhydrous MeOH (3 ml) under nitrogen was added sodium cyanoborohydride (0.02 g, 0.32 mmol) and the mixture was stirred for 24 h. The mixture was quenched with saturated aqueous K$_2$CO$_3$ (0.5 ml) and the solvent was removed in vacuo. The residue was purified by flash chromatography (silica gel, 5–10% MeOH/CH$_2$Cl$_2$) to give 0.049 g (24.9%) of the title compound as a yellow solid; $^1$H NMR (360 MHz, DMSO-d$_6$) δ12.05 (1H, d, J 6.2 Hz), 8.18 (1H, d, J 6.5 Hz), 7.87 (2H, d, J 9.0 Hz), 7.12 (2H, d, J 8.9 Hz), 7.04 (2H, d, J 8.8 Hz), 6.56 (2H, d, J 8.8 Hz), 3.31 (4H, d, J 6.3 Hz), 1.99 (3H, s), 0.79 (2H, m), 0.18 (4H, m), 0.00 (4H, m); MS (ES$^+$) m/z 459/461 NH]$^+$. Anal. found: C, 69.51; H, 6.03; N, 11.94. C$_{27}$H$_{27}$N$_4$ClN$_4$O.0.5H$_2$O requires: C, 69.29; H, 6.03; N, 11.97%.

2-(4-Chlorophenyl)-7-[4-(N-cycloropylmethylamino)phenyl]-2,5-dihydro-6-methylpyrazolo[4,3-c]pyridin-3-one Also isolated from the above reaction as a yellow solid, 0.083 g (47.9%). $^1$H NMR (360 MHz, DMSO-d$_6$) δ12.07 (1H, d, J 6.3 Hz), 8.21 (1H, d, J 6.6 Hz), 7.91 (2H, d, J 8.9 Hz), 7.16 (2H, d, J 8.9 Hz), 6.99 (2H, d, J 8.9 Hz), 6.42 (2H, d, J 8.8 Hz), 5.62 (1H, br s), 2.70 (2H, d, J 2.9 Hz), 2.03 (3H, s), 0.83 (1H, m), 0.23 (2H, m), −0.01 (2H, m); MS (ES$^+$) m/z 405/407 [MH]$^+$.

EXAMPLE 53

7-(4-Carboxamidophenyl)-2-(4-chlorophenyl)-2,5-dihydro-6-methyl-pyrazolo[4,3-c]pyridin-3-one To sulfuric acid (5 ml; 85% v/v H$_2$O) was added the product of Example 49c (0.05 g, 0.14 mmol) and the solution heated at 85° C. for 4 hours. The reaction was poured into ice water (10 ml) and the solution adjusted to pH 7 with sodium carbonate. The yellow precipitate was filtered off and air dried. The resulting solid was recrystallised from MeOH/CH$_2$Cl$_2$/CH$_3$CO$_2$C$_2$H$_5$ to give the product as an orange solid, 0.045 g (85.7%). $^1$H NMR (360 MHz, DMSO-d$_6$) δ12.52 (1H, br s), 8.31 (1H, s), 8.12 (2H, d, J 12.9 Hz), 8.08 (1H, m), 8.04 (2H, d, J 12.0 Hz), 7.60 (2H, d, J 11.9 Hz), 7.44 (1H, m), 7.42 (2H, d, J 12.7 Hz), 2.26 (3H, s); MS (ES$^+$) m/z 379/381 [MH]$^+$. Anal. found: C, 56.54; H, 3.98; N, 12.87. C$_{20}$H$_{25}$ClN$_4$O$_2$.0.5H$_2$SO$_4$ requires: C, 56.14; H, 3.77; N, 13.10%.

EXAMPLE 54

2-(4-Chlorophenyl)-2,5-dihydro-7-(3-methoxycarbonylphenyl)-6-methyl-pyrazolo[4,3-c]pyridin-3-one Hydrogen chloride was bubbled through a suspension of the product of Example 50c (0.1 g, 0.27 mmol) in MeOH (5 ml) and CH$_2$Cl$_2$ (2 ml) at 0° C. for 30 minutes; the vessel was then sealed and stirred at 25° C. for 24 hours. The solvent was removed in vacuo and the residue dissolved in CH$_2$Cl$_2$/MeOH (10:1) and washed twice with sat. sodium hydrogen carbonate solution. The organic phase was then separated, dried (MgSO$_4$), filtered and evaporated to give a yellow solid. The crude product was purified by flash chromatography (silica gel, 7% MeOH/CH$_2$Cl$_2$) to afford the title compound as a yellow solid, 0.032 g (29.3%). $^1$H NMR (360 MHz, DMSO-d$_6$) δ12.51 (1H, br s), 8.31 (1H, s), 8.12 (3H, m), 8.08 (1H, m), 7.80 (1H, m), 7.77 (1H, m), 7.39 (2H, d, J 8.9 Hz), 3.88 (3H, s), 2.24 (3H, s); MS (ES$^+$) m/z 394/396 [MH]$^+$. Anal. found: C, 62.37; H, 4.20; N, 10.19. C$_{21}$H$_{16}$ClN$_3$O$_3$.0.5H$_2$O requires: C, 62.69; H, 4.13; N, 10.44%.

EXAMPLE 55

2-(4-Chlorophenyl)-2,5-dihydro-6-methyl-7-[3-(pyridin-2-ylmethylaminomethyl)phenyl]pyrazolo[4,3-c]pyridin-3-one a) 2-(4-Chlorophenyl)-7-(3-formylphenyl)-2,5-dihydro-6-methylpyrazolo[4,3-c]pyridin-3-one To a suspension of the product of Example 50c (0.1 g, 0.28 mmol) in CH$_2$Cl$_2$ (8 ml) at 0° C. was added diisobutylaluminium hydride (1.0 M CH$_2$Cl$_2$ soln.; 0.55 ml; 0.55 mmol) and the resulting solution stirred for 2 hours at 25° C. HCl (1.0 M; 0.5 ml) was added dropwise at 0° C. and the mixture stirred vigorously for 15 minutes. The reaction was then diluted with CH$_2$Cl$_2$ and the organic phase washed with saturated aqueous sodium hydrogen carbonate solution. The organic phase was separated, dried (MgSO$_4$), filtered and evaporated to give the product as a yellow solid, 0.100 g (99.2%) which was used without further purification in the subsequent step. MS (ES$^+$) m/z 364/366 [MH]$^+$.

b) 2-(4-Chlorophenyl)-2,5-dihydro-6-methyl-7-[3-(pyridin-2-ylmethylaminomethyl)phenyl]pyrazolo[4,3-c]pyridin-3-one To a solution of the product of Example 55a (0.1 g, 0.275 mmol) in methanol (5 ml) was added acetic acid (31 µl, 0.55 mmol), sodium cyanoborohydride (10.3 mg, 0.165 mmol) and 2-(aminomethyl)pyridine (0.17 ml, 1.65 mmol). After stirring for 18 hours the solvent was evaporated and the crude product purified by flash chromatography (silica gel, 10% MeOH/CH$_2$Cl$_2$) to afford the title compound as a yellow solid, 0.023 g (18.4%). $^1$H NMR (360 MHz, CD$_3$OD) δ8.46 (1H, s), 8.43 (1H, s), 7.93 (2H, d, J 8.9 Hz), 7.73 (1H, m), 7.31 (8H, m), 3.93 (2H, s), 3.88 (2H, s 2.32 (3H, s); MS (ES$^+$) m/z 456/458 [MH]$^+$.

EXAMPLE 56

2-(4-Chlorophenyl)-2,5-dihydro-6-methyl-7-[4-(pyridin-2-ylmethylaminomethyl)phenyl]pyrazolo[4,3-c]pyridin-3 -one a) 2-(4-Chlorophenyl)-7-(4-formylphenyl)-2,5-dihydro-6-methylpyrazolo[4,3-c]pyridin-3-one Following a similar procedure to that described in Example 55a, except using the product of Example 49c instead of the product of Example 50c, the title compound was prepared as a yellow solid. MS (ES$^+$) m/z 364/366 [MH]$^+$.

b) 2-(4-Chlorophenyl)-2,5-dihydro-6-methyl-7-[4-(pyridin-2-ylmethylaminomethyl)phenyl]pyrazolo[4,3-c]pyridin-3-one Following a similar procedure to that described in Example 55b, except using the product of Example 56a, the title compound was prepared as a yellow solid. $^1$H NMR (360 MHz, CD$_3$OD) δ8.52 (1H, s), 8.40 (1H, s), 7.91 (2H, d, J 8.9 Hz), 7.82 (1H, m), 7.41 (8H, m), 3.93 (2H, s 3.88 (2H, s), 2.29 (3H, s); MS (ES$^+$) m/z 456/458 [MH]$^+$.

EXAMPLE 57

7-[4-(Benzylaminomethyl)phenyl]-2-(4-chlorophenyl)-2,5-dihydro-6-methyl-pyrazolo[4,3-c]pyridin-3-one Following a similar procedure to that described in Example 55b, except using the product of Example 56a, and benzylamine instead of 2-(aminomethyl)pyridine, the title compound was prepared as a yellow solid.

$^1$H NMR (360 MHz, CD$_3$OD) δ7.77 (1H, s), 7.33 (2H, d, J 9.9 Hz), 6.84 (4H, s), 6.70 (7H, m), 3.20 (2H, s), 3.18 (2H, s), 1.68 (3H, s); MS (ES$^+$) m/z 455/457 [MH]$^+$.

EXAMPLE 58

7-(3-Carboxamidophenyl)-2-(4-chlorophenyl)-2,5-dihydro-6-methyl-pyrazolo[4,3-c]pyridin-3-one Following a similar procedure to that described in Example 53, except using the product of Example 50c instead of the product of 49c, the title compound was prepared as a yellow solid. $^1$H NMR (360 MHz, DMSO-d$_6$) δ12.45 (1H, br s), 8.61 (1H, s), 8.12 (2H, d, J 8.9 Hz), 8.00 (3H, m), 7.60 (2H, m), 7.40 (2H, d, J 9.0 Hz), 2.24 (3H, s); MS (ES$^+$) m/z 379/381 [MH]$^+$.

EXAMPLE 59

2-(4-Chlorophenyl)-2,5-dihydro-6-methyl-7-[4-(pyrrolidin-1-ylmethyl)phenyl]-pyrazolo[4,3-c]pyridin-3-one Following a similar procedure to that described in Example 55b, except using the product of Example 56a, and pyrrolidine instead of 2-(aminomethyl)pyridine, the title compound was prepared as a yellow solid.

$^1$H NMR (360 MHz, CD$_3$OD) δ8.26 (1H, s), 7.91 (2H, d, J 8.9 Hz), 7.38 (4H, s), 7.24 (2H, d, J 8.9 Hz), 3.63 (2H, s), 2.54 (4H, br s), 2.24 (3H, s), 1.76 (4H, br s); MS (ES$^+$) m/z 419/421 [MH]$^+$.

EXAMPLE 60

2-(4-Chlorophenyl)-2,5-dihydro-7-[4-(hydroxymethyl)phenyl]-6-methyl-pyrazolo[4,3-c]pyridin-3-one a) 2-(4-Chlorophenyl)-2,5-dihydro-7-(4-methoxycarbonylphenyl)-6-methyl-pyrazolo[4,3-c]pyridin-3-one Following a similar procedure to that described in Example 54 except using the product of Example 49c the title compound was prepared as a yellow solid. $^1$H NMR (360 MHz, DMSO-d$_6$) δ12.51 (1H, d, J 6.0 Hz), 8.60 (1H, d, J 6.6 Hz), 8.12 (2H, d, J 8.2 Hz), 8.10 (2H, d, J 8.3 Hz), 7.68 (2H, d, J 8.2 Hz), 7.40 (2H, d, J 8.2 Hz), 3.90 (3H, s), 2.26 (3H, s); MS (ES$^+$) m/z 394/396 [MH]$^+$. Anal. found: C, 61.55; H, 4.45; N, 9.74. C$_{21}$H$_{16}$ClN$_3$O$_3$.H$_2$O requires: C, 61.24; H, 4.40; N, 10.20%.

b) 2-(4-Chlorophenyl)-2,5-dihydro-7-[4-(hydroxymethyl)phenyl]-6-methyl-pyrazolo[4,3-c]pyridin-3-one To a suspension of the product from Example 60a (0.025 g, 0.06 mmol) in CH$_2$Cl$_2$ (5 ml) at −10° C. was added diisobutylaluminium hydride (1.0 M CH$_2$Cl$_2$ soln.; 0.2 ml, 0.2 mmol) and the resulting solution was stirred for 12 hours at 25° C. HCl (1.0 M; 0.5 ml) was added dropwise at 0° C. and the mixture stirred vigorously for 15 minutes. The reaction was then diluted with CH$_2$Cl$_2$ and the organic phase was washed with saturated aqueous sodium hydrogen carbonate solution. The organic phase was separated, dried (AgSO$_4$), filtered and evaporated to give the product as a yellow solid. The crude product was purified by flash chromatography (silica gel, 10% MeOH/CH$_2$Cl$_2$) to afford the title compound as a yellow solid, 0.016 g (68.8%). $^1$H NMR (360 MHz, DMSO-d$_6$) δ12.43 (1H, br s), 8.58 (1H, s), 8.13 (2H, d, J 9.0 Hz), 7.43 (6H, m), 5.25 (1H, t, J 5.7 Hz), 4.57 (2H, d, J 5.5 Hz), 2.25 (3H, s); MS (ES$^+$) m/z 366/368 [MH]$^+$.

EXAMPLE 61

2-(4-Chlorophenyl)-2,5-dihydro-7-(4-iodophenyl)-6-methylpyrazolo[4,3-c]pyridin-3-one a) 2-(4-Chlorophenyl)-7-(4-diazophenyl)-2,5-dihydro-6-methylpyrazolo[4,3-c]pyridin-3-one fluoroborate To the product of Example 40 (5.0 g, 14.3 mmol) in N,N-dimethylformamide (200 ml) containing tetrafluoroboric acid (3.6 ml, 28.5 mmol) was added dropwise isoamyl nitrite (3.8 ml, 28.5 mmol). After 4 hours the reaction was poured into ice water (800 ml) with vigorous stirring. After stirring for 30 minutes the precipitate was filtered off washing with cold ethanol and diethyl ether. Drying under high vacuum gave the product as a purple solid (78%). MS (ES$^+$) m/z 334/336 [M-N$_2$]$^+$.

b) 2-(4-Chlorophenyl)-2,5-dihydro-7-(4-iodophenyl)-6-methylpyrazolo[4,3-c]pyridin-3-one To a solution of potassium iodide (1.77 g, 10.6 mmol) and iodine (1.2 g, 4.72 mmol) at 10° C. was added dropwise a solution of the product of Example 61a (4.0 g, 9.0 mmol) in dimethylsulphoxide (15 ml). After stirring for 1 hour the temperature was raised to 40° C. for 30 minutes. After cooling to room temperature saturated aqueous sodium bisulfite solution (30 ml) was added in one portion with vigorous stirring, and then the reaction further diluted with ice water (200 ml). The solid was collected by filtration, and washed with water, cold ethanol, and diethyl ether. Drying under high vacuum gave the title product as a yellow solid, 3.99 g (97%). $^1$H NMR (360 MHz, DMSO-dr) δ12.52 (1H, br s), 8.60 (1H, br s), 8.12 (2H, d, J 12.8 Hz), 7.87 (2H, d, J 11.7 Hz), 7.42 (2H, d, J 12.8 Hz), 7.33 (2H, d, J 11.8 Hz), 2.25 (3H, s); MS (ES$^+$) m/z 462/464 [MH]$^+$.

EXAMPLE 62

2-(4-Chlorophenyl)-2,5-dihydro-6-methyl-7-[4-(3-dimethylaminoprop-1-yn-1-yl)phenyl]pyrazolo[4,3-c]pyridin-3-one To the product of Example 61b (0.3 g, 0.7 mmol) and N,N-dimethylpropargylamine (52 μl, 0.48 mmol) in piperidine (5 ml) was added copper(I) iodide (0.0006 g, 3.2 μmol) and tetrakis(triphenylphosphine)-palladium(0) (0.0037 g, 3.2 1mol), and the mixture heated at 80° C. for 12 hours. The solvent was removed in vacuo and the crude product purified by flash chromatography (silica gel, 7% MeOHICH$_2$Cl$_2$). Recrystallisation from MeOH/CH$_2$Cl$_2$/CH$_3$CO$_2$C$_2$H$_5$ afforded the title compound as a yellow solid, 0.087 g (64.3%). $^1$H NMR (360 MHz, DMSO-d$_6$) δ12.43 (1H, br s), 8.59 (1H, s), 8.13 (2H, d, J 9.0 Hz), 7.54 (2H, m), 7.41 (2H, d, J 9.0 Hz), 3.60 (2H, s), 2.34 (6H, s), 2.26 (3H, s); MS (ES$^+$) m/z 417/419 [MH]$^+$, 209 [(M+2H)/2]$^+$.

EXAMPLE 63

2-(4-Chlorophenyl)-2,5-dihydro-7-[4-(imidazol-1-yl)phenyl]-6-methyl-pyrazolo[4,3-c]pnyridin-3-one To a solution of the product of Example 61b (0.1 g, 0.22 mmol) and imidazole (0.034 g, 0.5 mmol) in 1-methyl-2-pyrrolidinone (1 ml) was added potassium carbonate (0.060 g, 0.43 mmol) and copper bronze (0.002 g, 31 μmol) and the mixture heated at 140° C. for 12 hours. The solvent was removed in vacuo and the crude product purified by flash chromatography (silica gel, 7% MeOH/CH$_2$Cl$_2$). Recrystallisation from MeOH/CH$_2$Cl$_2$/CH$_3$CO$_2$C$_2$H$_5$ afforded the title compound as a sandy coloured solid, 0.037 g (42.5%). $^1$H NMR (360 MHz, DMSO-d$_6$) δ12.53 (1H, br s), 9.82 (1H, br s), 8.62 (1H, s), 8.13 (2H, d, J 9.0 Hz), 8.01 (1H, br s), 7.96 (2H, d, J 9.0 Hz), 7.82 (2H, d, J 9.1 Hz), 7.43 (2H, d, J 9.0 Hz), 3.60 (2H, s), 2.34 (6H, s), 2.31 (3H, s); MS (ES$^+$) m/ 402/404 [MH]$^+$, 201 [(M+2H)/2]$^+$.

EXAMPLE 64

2-(4-Chlorophenyl)-2,5-dihydro-7-[4-(imidazol-2-yl)phenyl]-6-methyl-pyrazolo[4,3-c]pyridin-3-one a) 2-(4-Chlorophenyl)-2,5-dihydro-6-methyl-7-[4-(1-(trimethylsilyloxyethoxy-methyl)imidazol-2-yl)phenyl]pyrazolo[4,3-c]pyridin-3-one To a solution of N-(trimethylsilyloxyethoxymethyl) imidazole (0.98 g, 1 mmol) in THF (5 ml) at −78° C. was added n-butyllithium (1.6 M sol. in hexanes; 0.65 ml, 1.04 mmol) dropwise with stirring. After 15 minutes the reaction was allowed to warm to room temperature. After stirring for 10 minutes zinc chloride (0.5 M sol. in THF; 2.0 ml, 1.0 mmol) was added in one portion and the reaction stirred for 1 hour. To this solution was added a solution of the product of Example 61b (0.313 g, 0.68 mmol) and tetrakis (triphenylphosphine)palladium(0) (0.08 g, 0.07 mmol) in N,N-dimethylformamide (5 ml) dropwise and then the temperature was raised to 50° C. with stirring for 10 hours. The solvent was removed it vacuo and the crude product was purified by flash chromatography (silica gel, 6% MeOH/CH$_2$Cl$_2$). Recrystallisation from MeOH/CH$_2$Cl$_2$/CH$_3$CO$_2$C$_2$H$_5$ afforded the title compound as a yellow solid, 0.12 g (33.0%). $^1$H NMR (250 MHz, DMSO-d$_6$) δ12.56 (1H, br s), 8.64 (1H, br s), 8.62 (1H, s), 8.19 (2H, d, J 8.9 Hz), 7.95 (2H, d, J 9.0 Hz), 7.68 (2H, d, J 9.0 Hz), 7.56 (1H, s), 7.45 (2H, d, J 8.9 Hz), 7.12 (1H, s), 5.49 (2H, s), 3.65 (2H, t, J 7.8 Hz), 2.35 (3H, s), 0.93 (2H, t, J 7.8 Hz), 0.00 (9H, s); MS (ES$^+$) m/z 532/534 [MH]$^+$.

b) 2-(4-Chlorophenyl)-2,5-dihydro-7-[4-(imidazol-2-yl)phenyl]-6-methyl-pyrazolo[4,3-c]pyridin-3-one hydrochloride salt The product from Example 64a (0.1 g, 0.19 mmol) was dissolved in HCl (5.0 M, 5 ml) and ethanol (10 ml) and the solution warmed to 50° C. for 12 hours. The reaction was allowed to cool and then adjusted to pH 7 by the addition of sodium hydroxide solution. The precipitate was collected by filtration washing with water, cold ethanol and diethyl ether. The crude product was purified by flash chromatography (silica gel, 6% MeOH/CH$_2$Cl$_2$). The solid obtained was taken up in the minimum amount of methanol, diluted with ethyl acetate, and hydrogen chloride was then bubbled through the solution. The precipitate was collected by filtration washing with ethyl acetate to give the product as a pale yellow solid, 0.56 g (68.0%). $^1$H NMR (360 MHz, DMSO-d$_6$) δ15.11 (1H, br s), 12.73 (1H, d, J 2.3 Hz), 8.60 (1H, d, J 2.3 Hz), 8.27 (2H, d, J 8.4 Hz), 8.13 (2H, d, J 8.7 Hz), 7.85 (2H, s), 7.82 (2H, d, J 8.4 Hz), 7.42 (2H, d, J 8.5 Hz), 2.31 (3H, s); MS (ES$^+$) m/z 402/404 [MH]$^+$.

EXAMPLE 65

2-(4-Chlorophenyl)-2,5-dihydro-6-methyl-7-[4-(1,2,3-triazol-5-yl)phenyl]-pyrazolo[4,3-c]pyridin-3-one a) 2-(4-Chlorophenyl)-2,5-dihydro-6-methyl-7-[4-(1-(trimethylsilyloxyethoxy-methyl)-1,2,3-triazol-5-yl)phenyl]pyrazolo[4,3-c]pyridin-3-one Following a similar procedure to that described in Example 64a, except using 1-(trimethylsilyloxyethoxymethyl)-1,2,3-triazole instead of N-(trimethylsilyloxyethoxymethyl)imidazole the title compound was prepared as a yellow solid. $^1$H NMR (250 MHz, DMSO-d$_6$) δ12.08 (1H, br s), 8.64 (1H, s), 8.62 (1H, s), 8.20 (1H, s), 8.19 (2H, d, J 8.2 Hz), 7.92 (2 d, J 8.4 Hz), 7.67 (2H, d, J 8.3 Hz), 7.48 (2H, d, J 8.2 Hz), 5.89 (2H, s), 3.74 (2H, t, J 8.1 Hz), 2.35 (3H, s), 0.93 (2H, t, J 8.1 Hz), 0.00 (9H, s); MS (ES$^+$) m/z 533/535 [MH]$^+$.

b) 2-(4-Chlorophenyl)-2,5-dihydro-6-methyl-7-[4-(1,2,3-triazol-5-yl)phenyl]-pyrazolo[4,3-c]pyridin-3-one Following a similar procedure to that described in Example 64b, except using the product from Example 65a, the title compound was prepared as a yellow solid. $^1$H NMR (360 MHz, DMSO-d$_6$) δ12.49 (1H, d, J 6.13 Hz), 8.58 (1H, d, J 6.13 Hz), 8.15 (2H, d, J 8.2 Hz), 7.98 (2H, d, J 8.3 Hz), 7.62 (2H, d, J 8.2 Hz), 7.41 (2H, d, J 8.2 Hz), 2.31 (3H, s); MS (ES$^+$) m/Z 403/405 [MH]$^{+b}$, $^{202}$ [(M+2H)/2]$^+$. Anal. found: C, 61.87; H, 3.57: N, 20.19. C$_{21}$H$_{15}$ClN$_6$O.0.3H$_2$O requires: C, 61.78; H, 3.85; N, 20.59%.

EXAMPLE 66

2-(4-Chlorophenyl)-2,5-dihydro-6-methyl-7-[4-(thiazol-2-yl)phenyl]-pyrazolo[4,3-c]pyridin-3-one Following a similar procedure to that described in Example 64a, except using thiazole instead of N-(trimethylsilyloxyethoxymethyl)imidazole the title compound was prepared as a yellow solid. $^1$H NMR (360 MHz, DMSO-d$_6$) δ12.50 (1H, br s), 8.64 (1H, s), 8.60 (1H, s), 8.14 (2H, d, J 9.0 Hz), 8.07 (2H, d, J 8.9 Hz), 7.97 (1H, d, J 3.3 Hz), 7.83 (1H, d, J 3.3 Hz), 7.67 (2H, d, J 8.9 Hz), 7.41 (2H, d, J 8.9 Hz), 2.30 (3H, s); MS (ES$^+$) m/z 419/421 [MH]$^+$.

EXAMPLE 67

2-(4-Chlorophenyl)-2,5-dihydro-7-(4-hydroxypheny)-6-methylpyrazolo[4,3-c]pyridin-3-one The product of Example 61a (0.15 g, 0.33 mmol) in sulfuric acid (0.05 M, 8 ml) was heated at 75° C. for 3 hours. After cooling to room temperature the yellow precipitate was collected by filtration, and washed with water. The crude product was purified by flash chromatography (silica gel, 6% MeOH/CH$_2$Cl$_2$) to give the title product as a yellow solid, 0.85 g (72.0%). $^1$H NMR (360 MHz, DMSO-d$_6$) δ12.37 (1H, br s), 9.59 (1H, br s), 8.51 (1H, s), 8.14 (2H, d, J 8.6 Hz), 7.42 (2H, d, J 8.5 Hz), 7.32 (2H, d, J 8.6 Hz), 6.87 (2H, d, J 8.9 Hz), 2.26 (3H, s); MS (ES$^+$) m/z 352/354 [MH]$^+$.

EXAMPLE 68

2-(4Chlorophenyl)-2,5-dihydro-7-[4-(3-hydroxyprop-1-yn-1-yl)phenyl]-6-methylpyrazolo[4,3-c]pyridin-3-one Following a similar procedure to that described in Example 62 except using propargyl alcohol instead of N,N-dimethylpropargylamine the title compound was prepared as a yellow solid. $^1$H NMR (360 MHz, DMSO-d$_6$) δ12.44 (1H, br s), 8.59 (1H, s), 8.13 (2H, d, J 9.0 Hz), 7.54 (4H, s), 7.42 (2H, d, J 9.0 Hz), 5.38 (1H, t, J 6.0 Hz), 4.35 (2H, d, J 5.6 Hz), 2.26 (3H, s); MS (ES$^+$) m/z 390/392 [MH]$^+$.

EXAMPLE 69

7-[4-(6-Azabenzimidazol-2-yl)phenyl]-2-(4-chlorophenyl)-2,5-dihydro-6-methylpyrazolo[4,3-c]pyridin-3-one di(hydrochloride)

The product of Example 60 was dissolved in dry dimethylsulfoxide (4 ml), and dry triethylamine (2.6 ml) added. To this mixture was added slowly with stirring pyridine-sulfur trioxide complex (0.50 g). After stirring for an additional 0.5 hours the reaction mixture was purified by flash chromatography (silica gel, eluent 5% methanol/dichloromethane) to yield 0.133 g (97%) of the benzaldehyde (also prepared in Example 56a).

To the benzaldehyde (0.015 g) and 3,4-diaminopyridine (0.005 g) was added dry N,N-dimethylformamide (1 ml), and the mixture was heated in air at 140° C. for 30 hours. After removal of the N,N-dimethylformamide at reduced pressure, the residue was purified by preparative thin layer chromatography (silica gel, eluent 10% methanol/dichloromethane). The resulting product was exposed to methanolic hydrogen chloride, and evaporated to afford the title compound; $^1$H NMR (500 MHz, DMSO-d$_6$) 9.50 (1H, s), 8.63 (2H, m), 8.45 (2H, m), 8.21 (1H, m), 8.14 (2H, m), 7.85 (2H, m), 7.43 (2H, m), 2.34 (3H, s); MS (ES$^+$) m/z 453/455 [MH]$^+$.

EXAMPLE 70

7-(2-Acetyl-2,3,4,9-tetrahydro-1H-pyrido[3,4-b]indol-6-yl)-2-(4-chlorophenyl)-2,5-dihydro-6-methylpyrazolo[4,3-c]pyridin-3-one To tin(II) chloride (0.475 g) was added water (0.5 ml), 10 M aqueous hydrochloric acid (0.5 ml) and methanol (7 ml). The mixture was cooled to −15° C. and the product of Example 61a (0.260 g, 0.375 mmol) was added slowly portionwise with stirring over 0.25 hours. After stirring for an additional 0.5 hours, 1-acetyl-4-piperidone (0.100 ml) was added, followed by pyridine (2 ml), and the mixture was allowed to warm to room temperature. On dilution with water (50 ml) the yellow precipitate was recovered by filtration, washed with water, then diethyl ether, and dried in vacuo at 50° C. The crude hydrazone thus obtained was dissolved in dry pyridine (3 ml), and pyridinium tosylate (0.132 g) added. This mixture was heated at reflux under nitrogen for 6 days. After removal of the pyridine at reduced pressure, the residue was partitioned between aqueous NaHCO$_3$ and 10% methanol/dichloromethane. The organic extracts were evaporated and the residue was purified by flash chromatography (silica gel, eluent 6–10% methanol/dichloromethane) to yield the title compound, after crystallisation from hot methanol; $^1$H NMR (360 MHz, DMSO-d$_6$) δ12.43 (1H, br d), 11.05 (1H, br d), 8.54 (1H, in), 8.11 (2H, m), 7.52 (1H, m), 7.39 (3H, m), 7.15 (1H, in), 4.65 (2H, br d), 3.86 (1H, m), 3.79 (1H, m), 2.90 (1H, m), 2.79 (1H, m), 2.26 (3H, s), 1.98+1.93 (3H, rotamers 1:1); MS (ES$^+$) m/z 472/474 [H]$^+$.

EXAMPLE 71

2-(4-Chlorophenyl)-7-(2-ethyl-2,3,4,9-tetrahydro-1H-pyrido[3,4-b]indol-6-yl)-2,5-dihydro-6-methylpyrazolo[4,3-c]pyridin-3-one By the method of Example 70, reaction with 1-ethyl-4-piperidone gave the title compound, after crystallisation from hot methanol/ethyl acetate; $^1$H NMR (500 MHz, DMSO-d$_6$) δ12.35 (1H, br), 10.91 (1H, br s), 8.54 (1H, s), 8.11 (2H, m), 7.40 (4H, m), 7.11 (1H, m), 3.60 (2H, br s), 2.82 (4H, br s), 2.62 (2H, br s), 2.25 (3H, s), 1.13 (3H, m); MS (ES$^+$) m/ z 458/460 [MH]$^+$.

EXAMPLE 72

2-(4-Chlorophenyl)-2,5-dihydro-7-[2-(dimethylaminomethyl)indol-5-yl]-6-methylpyrazolo[4,3-c]pyridin-3-one a) 7-(4-Amino-3-bromophenyl)-2-(4-chlorophenyl)-2,5-dihydro-6-methylpyrazolo[4,3-c]pynridin-3-one To 7-(4-aminophenyl)-2-(4-chlorophenyl)-2,5-dihydro-6-methylpyrazolo[4,3-c]pyridin-3-one (2.0 g, 5.7 mmol) and solid sodium hydrogen carbonate (2.0 g, 23.8 mmol), under nitrogen, was added dry N,N-dimethylformamide (20 ml). To the stirred mixture was added bromine (0.35 ml, 6.8 mmol) dropwise. After stirring for an additional 0.7 hours, ethyl acetate (50 ml) and water (50 ml) was added. The organic extracts were dried (Na$_2$SO$_4$), evaporated and the residue triturated with diethyl ether to afford the title compound as an orange solid (2.2 g, 90%).

b) 7-[4-Amino-3-(3-dimethylaminoprop-1-yn-1-yn)phenyl]-2-(4-chlorophenyl)-2,5-dihydro-6-methylnyrazolo[4,3-c]pyridin-3-one To the product of Example 72a (0.401 g, 0.93 mmol) and copper(I) iodide (0.005 g), under nitrogen, was added dry piperidine (5 ml) and dry N,N-dimethylformamide (10 ml), followed by N,N-dimethylpropargylamine (0.30 ml), and tetrakis(triphenylphosphine)palladium(0) (0.020 g). The mixture was then heated at 100° C. for 24 hours. A further portion of N,N-dimethylpropargylamine (0.30 ml) was then added and heating continued for a further 48 hours. The mixture was then allowed to cool to room temperature, the solvent was removed at reduced pressure, and the residue was purified by flash chromatography (silica gel, eluent 10% methanol/dichloromethane) to yield 0.28 g (70%) of the title compound, after recrystallisation from hot ethyl acetate, as a yellow solid; $^1$H NMR (360 MHz, DMSO-d$_6$) δ12.40 (1H, br s), 8.50 (1H, br s), 8.14 (2H, m), 7.42 (2H, m), 7.35 (1H, m), 7.26 (1H, m), 6.83 (1H, d, J 8.5 Hz), 5.74 (2H, br s), 4.17 (2H, s), 2.76 (6H, s), 2.27 (3H, s); MS (ES$^+$) m/z 432/434 [MH]$^+$.

c) 2-(4-Chlorophenyl)-2,5-dihydro-6-methyl-7-[4-trifluoroacetamido-3-(3-dimethylaminoprop-1l-yn-1-yl)phenyl]pyrazolo[4,3-c]pyridin-3-one To the product of Example 72b (0.535 g, 1.24 mmol) in dry pyridine (10 ml) at 4° C. was added trifluoroacetic anhydride (1.0 ml). The mixture was then stirred at room temperature for 1 hour. The solvent was removed at reduced pressure, and the residue was partitioned between dichloromethane and aqueous NaHCO$_3$. The organic layer was separated, evaporated, and the residue purified by flash chromatography (silica gel, eluent 10% methanol/dichloromethane) to yield 0.39 g (60%) of the title compound. MS (ES$^+$) m/z 528/530 [MH]$^+$.

0d) 2-(4-Chlorophenyl)-2,5-dihydro-7-[2-(dimethylaminomethyl)indol-5-yl]-6-methylpyrazolo[4 3-c]pyridin-3-one To the product of Example 72c (0.361 g, 0.68 mmol) and copper(I) iodide (0.361 g), under nitrogen, was added dry N,N-dimethylformamide (15 ml). The mixture was then heated at 105° C. for 2 hours. The mixture was then allowed to cool to room temperature, diluted with 10% methanol/dichloromethane (50 ml), filtered, and the filtrate washed with aqueous ammonium hydroxide, brine, and then the organic extracts were evaporated at reduced pressure. The residue was purified by flash chromatography (alumina grade III, eluent 5% methanol/dichloromethane) to yield 0.206 g (70%) of the title compound, after recrystallisation from hot ethyl acetate, as a yellow solid; $^1$H NMR (360 MHz, DMSO-d$_6$) δ12.38 (1H, br s), 11.13 (1H, br s), 8.53 (1H, s), 8.12 (2H, m), 7.55 (1H, br s), 7.40 (3H, m), 7.13 (1H, m), 6.31 (1H, m), 3.57 (2H, s), 2.26 (3H, s), 2.22 (6H, s); MS (ES$^+$) δ7ii/z 432/434 [MH]$^+$.

EXAMPLE 73

7-(Benzimidazol-5-yl)-2-(4-chlorophenyl)-2,5-dihydro-6-methylpyrazolo[4,3-c]pyridin-3-one a) Ethyl 3-(4-acetamidohenyl)-4-chloro-2-methyl-5-pyridinecarboxylate To a mixture of copper(II) acetylacetone (0.122 g) and ethanol (24 ml) was added sodium borohydride (0.18 g), followed by the product of Example 40b (0.508 g, 1.58 mmol). The reaction mixture was warmed briefly until homogeneous, and then stirred for 1 hour at room temperature. The mixture was then filtered, and the filtrate evaporated at reduced pressure. The residue was treated with 20% ethyl acetate in dichloromethane, filtered, and evaporated. The residue was dissolved in dry pyridine (5 ml), cooled to 4° C. under nitrogen and acetyl chloride (0.22 ml) added. The mixture was warmed to room temperature, stirred for 0.25 hour, the solvent evaporated at reduced pressure, and the residue was partitioned between dichloromethane and aqueous NaHCO$_3$. The organic layer was separated, dried (Na$_2$SO$_4$), and evaporated, to yield 0.441 g of the title compound. MS (ES$^+$) m/z 333/335 [H]$^+$.

b) Ethyl 3-(4-acetamido-3-nitrophenyl)-4-chloro-2-methyl-5-pyridinecarboxylate

To the product of Example 73a (0.441 g) was added sulfolane (3 ml) and dichloromethane (2 ml). The mixture was cooled to 4° C. under nitrogen and nitronium fluoroborate (0.250 g) added. The mixture was warmed to room temperature, stirred for 18 hours, then diluted with aqueous NaHCO$_3$, and extracted with dichloromethane (50 ml), then ethyl acetate (50 ml). The combined organic layers were dried (Na$_2$SO$_4$), and evaporated, and the residue was purified by flash chromatography (silica gel, eluent 25% ethyl acetate/dichloromethane) to yield the title compound. MS (ES$^+$) m/z 378/380 [MH]$^+$.

c) 7-(4-Acetamido-3-nitrophenyl)-2-(4-chlorophenyl)-2,5-dihydro-6-methylpyrazolo[4,3-c]pyridin-3-one The product from Example 73b and 4-chlorophenylhydrazine hydrochloride (0.35 g) in anhydrous 1-butanol (18 ml) was stirred at reflux under nitrogen for 7 hours. The mixture was then allowed to cool to room temperature, solvent evaporated, and the residue boiled with ethyl acetate (25 ml). The solid was then collected by filtration, and dried tit vacuo to give 0.249 g of the title compound; MS (ES$^+$) m/z 396/398 [MH]$^+$.

d) 7-(Benzimidazol-5-yl)-2-(4-chlorophenyl)-2,5-dihydro-6-methylpyrazolo[4,3-c]pyridin-3-one To the product of Example 73c and copper(II) acetylacetone (0.0225 g) in ethanol (4.5 ml) was added sodium borohydride (0.033 g). The reaction mixture was warmed briefly until homogeneous, and then stirred for 1 hour at room temperature. Formic acid (1 ml of 90%) and trimethyl orthoformate (5 ml) were added, and stirring continued for a further 1 hour at room temperature. The mixture was then filtered, and the filtrate evaporated at reduced pressure. The residue was treated with 20% methanol in trimethyl orthoformate (20 ml), and heated at reflux for 18 hours. The solvent was evaporated at reduced pressure, and the residue was chromatographed (alumina grade III, eluent 3%–20% methanol/dichloromethane; then silica, eluent 1% NH$_4$OH/7% methanol/dichloromethane) to yield 0.010 g of the title compound, after recrystallisation from hot 10% methanol/dichloromethane/ethyl acetate, as a yellow solid; $^1$H NMR (500 MHz, DMSO-d$_6$) δ8.58 (1H, m), 8.42 (1H, br s), 8.11 (2H, d, J 9 Hz), 7.75 (1H, br s), 7.72 (1H, d, J 8 Hz), 7.40 (2H, d, J 9 Hz), 7.35 (1H, m), 2.27 (3H, s); MS (ES$^+$) m/z 476/478 [MH]$^+$.

EXAMPLE 74

2-(4-Chlorophenyl)-2,5-dihydro-6-methyl-7-[4-(4-(morpholin-4-ylmethyl)-1,2,3-triazol-5-yl)phenyl]pyrazolo[4,3-c]pyridin-3-one a) 2-(4-Chlorophenyl)-7-[4-(3-chloroprop-1-yn-1-yl)phenyl]-2,5-dihydro-6-methylpyrazolo[4,3-c]pyridin-3-one To a solution of the product of Example 68 (0.6 g, 1.5 mmol), 2,6-lutidine (0.72 ml, 6.2 mmol) and lithium chloride (0.262 g, 6.2 mmol) in N,N-dimethylformamide (6 ml) at 0° C. was added methanesulphonyl chloride (0.36 ml, 4.6 mmol) dropwise and the solution allowed to warm to ambient temperature with stirring for 7 hours. The solvent was removed in vacuo and the crude product purified by flash chromatography (silica gel, 5% MeOH/CH$_2$Cl$_2$) to give the product as a yellow solid (0.463 g, 74%). $^1$H NMR (360 MHz, DMSO-d$_6$) δ12.49 (1H, br s), 8.59 (1H, s), 8.13 (2H, d, J 9.0 Hz), 7.59 (4H, m), 7.41 (2H, d, J 9.0 Hz), 4.75 (2H, s), 2.26 (3H, s); MS (ES$^+$) m/z 408/410/412 [MH]$^+$.

b) 2-(4-Chlorophenyl)-2,5-dihydro-6-methyl-7-[4-(4-(morpholin-4-methyl)-1,2,3-triazol-5-yl)phenyl]pyrazolo[4,3-c]pyridin-3-one To the product of Example 74a (0.2 g, 0.98 mmol) in dimethylsulphoxide (4 ml) was added sodium azide (0.075 g, 1.15 mmol) and the mixture stirred for 4 hours. Morpholine (0.25 ml) was added and the temperature raised to 110° C. for 8 hours. The solvent was removed lit vacuo and the crude product recrystallised from MeOH/CH$_2$Cl$_2$/CH$_3$CO$_2$C$_2$H$_5$ to give the product as a yellow solid (0.157 g, 63%). $^1$H NMR (360 MHz, DMSO-d$_6$) δ8.81 (1H, s), 8.43 (2H, d, J 8.3 Hz), 8.27 (2H, d, J 8.4 Hz), 7.89 (2H, d, J 8.3 Hz), 7.67 (2H, d, J 8.3 Hz), 4.00 (2H, s), 3.86 (4H, m), 2.73 (4H, m), 2.57 (3H, s); MS (ES$^+$) m/z 503/505 [MH]$^+$.

EXAMPLE 75

2-(4-Chlorophenyl)-2,5-dihydro-6-methyl-7-[4-(4-(morpholin-4-methyl)-1,2,3-triazol-5-yl)phenyl]pyrazolo[4,3-c]pyridin-3-one Following a similar procedure to that described in Example 74 except using 1-methylpiperazine instead of morpholine the title compound was prepared as a yellow solid. $^1$H NMR (360 MHz, DMSO-d$_6$) δ8.66 (1H, s), 8.33 (2H, d, J 9.35 Hz), 8.18 (2H, d, J 9.4 Hz), 7.77 (2H, d, J 9.4 Hz), 7.57 (2H, d, J 9.0 Hz), 3.87 (2H, s), 2.63 (4H, m), 2.47 (7H, m), 2.31 (3H, s MS (ES$^+$) m/z 515/517 [MH]$^+$.

EXAMPLE 76

2-(4-Chlorophenyl)-2,5-dihydro-6-methyl-7-[4-(2-(pyridin-2-yl)ethyl-1-yn-1-yl)phenyl]pyrazolo[4,3-c]pyridin-3-one To a degassed solution of the product of Example 61b (0.3 g, 0.65 mmol), copper iodide (0.001 g) and 2-ethynylpyridine (0.12 ml) in piperidine (5 ml) was added tetrakis(triphenylphosphine)palladium(0) (0.008 g, 6.3 [mol) and the solution heated at 80° C. for 12 hours. The solvent was removed in vacuo and the crude product purified by flash chromatography (silica gel, 5% MeOH/CH$_2$Cl$_2$) to give a solid which was recrystallised from MeOH/CH$_2$Cl$_2$/CH$_3$CO$_2$C$_2$H$_5$ to give a yellow solid (0.213 g, 75%).

$^1$H NMR (360 MHz, DMSO-d$_6$) δ12.52 (1H, d, J 6.2 Hz), 8.61 (1H, d, J 3.1 Hz), 8.59 (1H, d, J 5.9 Hz), 8.14 (2H, d, J 8.9 Hz), 7.90 (1H, m), 7.74 (5H, m), 7.41 (3H, m), 2.29 (3H, s); MS (ES$^+$) m/z 437/439 [MH]$^+$.

EXAMPLE 77

2-(4-Chlorophenyl)-2,5-dihydro-6-methyl-7-[4-(2-(pyridin-2-yl)ethyl)phenyl]pyrazolo[4,3-c]pyridin-3-one To a solution of the product of Example 76 (0.1 g, 0.22 mmol) in methanol (10 ml) was added palladium on charcoal (0.010 g, 10% Pd) and the mixture stirred vigorously under an atmosphere of hydrogen for 5 hours. The catalyst was filtered off, and the crude product purified by prep TLC (silica, 5% MeOH/CH$_2$Cl$_2$) to give the product as a yellow solid (0.065 g, 74%). $^1$H NMR (360 MHz, DMSO-d$_6$) δ12.43 (1H, br s), 8.53 (2H, m), 8.12 (2H, d, J 8.9 Hz), 7.70 (1H, m), 7.37 (7H, m), 7.20 (1H, m), 3.08 (4H, m), 2.25 (3H, s); MS (ES$^+$) m/z 441/439 [MH]$^+$, 221/222 [(M+2H)/2]$^+$. Anal. found: C, 68.02; H, 4.92; N, 12.14. C$_2$CH$_{21}$ClN$_4$O.H$_2$O requires: C, 68.04; H, 5.05; N, 12.21%.

EXAMPLE 78

2-(4-Chlorophenyl)-2,5-dihydro-6-methyl-7-[4-(1-methylimidazol-2-yl)phenyl]-pyrazolo[4,3-c[pnyridin-3-one Following a similar procedure to that described in Example 64a, except using 1-methylimidazole instead of N-(trimethylsilyloxyethoxymethyl)-imidazole, the title compound was prepared as a yellow solid. $^1$H NMR (360 MHz, DMSO-d$_6$) δ12.51 (1H, br s), 8.59 (1H, s), 8.14 (2H, d, J 8.9 Hz), 7.82 (2H, d, J 8.3 Hz), 7.63 (2H, d, J 8.3 Hz), 7.41 (2H, d, J 8.9 Hz), 7.32 (1H, s), 7.06 (1H, s), 3.83 (3H, s), 2.09 (3H, s); MS (ES$^+$) m/z 416/418 [MH]$^+$.

EXAMPLE 79

2-(4-Chlorophenyl)-2,5-dihydro-6-methyl-7-[4-(1,2,4-triazol-3-yl)phenyl]-pyrazolo[4,3-c]pyridin-3-one a) 2-(4-Chlorophenyl)-2,5-dihydro-6-methyl-7-[4-(1-(trimethylsilyloxyethoxy-methyl)-1,2,4-triazol-3-yl)phenyl]pyrazolo[4,3-c]pyridin-3-one Following a similar procedure to that described in Example 64a, except using 1-(trimethylsilyloxyethoxymethyl)-1,2,4-triazole instead of N-(trimethylsilyloxyethoxymethyl)imidazole, the title compound was prepared as a yellow solid. $^1$H NMR (360 MHz, DMSO-d$_6$) δ12.56 (1H, br s), 8.63 (1H, s), 8.20 (3H, m), 8.05 (2H, d, J 8.3 Hz), 7.78 (2H, d, J 8.3 Hz), 7.46 (2H, d, J 9.0 Hz), 5.70 (2H, s), 3.77 (2H, t, J 7.8 Hz), 2.35 (3H, s), 0.95 (2H, t, J 7.8 Hz), 0.00 (9H, s); MS (ES$^+$) m/z 533/535 [MH]$^+$.

b) 2-(4-Chlorophenyl)-2,5-dihydro-6-methyl-7-[4-(1,2,4-triazol-3-yl)phenyl]-pyrazolo[4,3-c]pyridin-3-one Following a similar procedure to that described in Example 64b, except using the product of Example 79a instead of the product of Example 64a, the title compound was prepared as a yellow solid. $^1$H NMR (360 MHz, DMSO-d$_6$) δ14.31 (1H, br s), 12.59 (1H, br s), 8.60 (1H, s), 8.40 (1H, br s), 8.15 (4H, m), 7.67 (2H, d, J 8.3 Hz), 7.41 (2H, d, J 9.4 Hz), 2.31 (3H, s); MS (ES$^+$) m/z 403/405 [MH]$^+$.

EXAMPLE 80

2-(4-Chlorophenyl)-2,5-dihydro-6-methyl-7-[4-(1-oxa-8-azaspiro[4.5]dec-3-en-3-yl)phenyl]pyrazolo[4,3-c]pyridin-3-one a) 7-[4-(8-tert-Butoxycarbonyl-1-oxa-8-azaspiro [4.5]dec-3-en-3-yl)phenyl]-2-(4-chlorophenyl)-2,5-dihydro-6-methylpyrazolo[4,3-c]pyridin-3-one To a degassed solution of the product of Example 61b (0.3 g, 0.65 mmol) and 3-tributylstannyl-1-oxa-8-azaspiro [4.5]dec-3-ene-8-carboxylic acid tert-butyl ester (0.515 g, 0.98 mmol) in N,N-dimethylformamide (5 ml) was added tetrakis (triphenylphosphine)palladium(0) (0.037 g, 32 mol) and the mixture heated at 80° C. for 18 hours. The solvent was removed in vacuo and the crude product purified by flash chromatography (silica gel, 5% MeOH/CH$_2$Cl$_2$) to give a yellow solid (0.265 g, 71 %). MS (ES$^+$) m/z 573/575 [MH]$^+$.
b) 2-(4-Chlorophenyl)-2,5-dihydro-6-methyl-7-[4-(1-oxa-8-azaspiro[4,5]dec-3-en-3-yl)]phenyl)]pyrazolo[4,3-c]pyridin-3-one To a suspension of the product of Example 80a (0.1 g, 0.17 mmol) in CH$_2$Cl$_2$ (10 ml) at 0° C. was added trifluoroacetic acid (2 ml). After stirring for 1 hour the solvent was removed in vacuo and the crude product purified by prep TLC (silica, 10% MeOH/CH$_2$Cl$_2$) to give the product as a yellow solid (0.058 g, 74%). $^1$H NMR (360 MHz, DMSO-d$_6$) δ12.59 (1H, br s), 8.60 (2H, br s), 8.12 (2H, d, J 8.9 Hz), 7.55 (4H, s), 7.41 (2H, d, J 9.0 Hz), 6.64 (1H, s), 5.03 (2H, s), 3.15 (4H, m), 2.27 (3H, s), 1.95 (2H, m), 1.80 (2H, m); MS (ES$^+$) m/z 403/405 [MH]$^+$.

EXAMPLE 81

7-Bromo-2-(4-chlorophenyl)-2,5-dihydro-6-methylpyrazolo[4,3-c]pyridin-3-one a) 3-Bromo-1,4-dihydro-2-methyl-4-oxo-5-pyridinecarboxylic acid To 6-methyl-4-(1H)-pyridone-3-carboxylic acid (prepared according to the procedure described in *J. Org. Chem.*, 1972, 37, 1145–1148) (10.0 g, 65.4 mmol) and dry pyridine (5.2 ml) in acetic acid (200 ml) at 100° C. was added bromine (14.6 g, 91.5 mmol) in acetic acid (30 ml) dropwise over 1 hour. Heating was continued for 2 hours then cooled to room temperature. The precipitate which formed on cooling was collected by filtration, and washed with methanol to give the product as a cream coloured solid (10.62 g, 70%). $^1$H NMR (250 MHz, DMSO-$d_6$) δ14.75 (1H, br s), 13.45 (1H, br s), 8.58 (1H, s), 2.53 (3H, s); MS (ES$^+$) m/z 232/234 MH]+, 214/216 [(M-($H_2$O))H]$^+$.

b) Methyl 3-bromo-4-chloro-2-methyl-5-pyridinecarboxylate

To the product of Example 81a (13.5 g, 58.1 mmol) was added phosphorus oxychloride (150 ml), and the mixture was heated at 60° C. for 3 hours under an atmosphere of dry nitrogen. The volatiles were removed in vacuo and the residue was azeotroped with toluene. The residue was diluted with $CH_2Cl_2$ (100 ml), cooled in an ice bath, methanol (15 ml) was added dropwise and the solution allowed to warm to ambient temperature over 1 hour. The residue was cooled in an ice bath, and quenched by cautious addition of saturated aqueous $NaHCO_3$. The aqueous layer was extracted with $CH_2Cl_2$ (3×100 ml), and the combined organic extracts were dried ($Na_2SO_4$) and evaporated in vacuo to give the product as a cream coloured solid which was dried under high vacuum at 60° C. for 18 hours (14.8 g, 96%). $^1$H NMR (250 MHz, CDCl$_3$) δ6 9.08 (1H, s), 4.18 (3H, s), 3.12 (3H, s); MS (ES$^+$) m/z 264/266/268 [MH]$^+$.

c) 7-Bromo-2-(4-chlorophenyl)-2,5-dihydro-6-methylpyrazolo[4,3-c]pyridin-3-one

Following a similar procedure to that described in Example 49c, except using the product of Example 81b instead of the product of Example 49b, the title compound was prepared as a yellow solid. $^1$H NMR (360 MHz, DMSO-$d_6$) δ12.77 (1H, br s), 8.60 (1H, s), 8.22 (2H, d, J 9.0 Hz), 7.96 (2H, d, J 9.0 Hz), 2.48 (3H, s); MS (ES$^+$) m/z 338/340/342 [MH]$^+$. Anal. found: C, 46.39; H, 2.49; N, 12.23. $C_{13}H_9BrClN_3O$ requires: C, 46.12; H, 2.68; N, 12.41%.

EXAMPLE 82

2-(4-Chlorophenyl)-2,5-dihydro-7-iodo-6-methylpyrazolo[4,3-c]pyridin-3-one a) 1,4-Dihydro-3-iodo-2-methyl-4-oxo-5-pyridinecarboxylic acid To 6-methyl-4-(1H)-pyridone-3-carboxylic acid (prepared according to the procedure described in *J. Org. Chem.*, 1972, 37, 1145–1148) (10.0 g, 65.4 mmol) and calcium carbonate (6.55 g, 65.4 mmol) in N,N-dimethylformamide (100 ml) was added iodine monochloride (21.2 g, 130.8 mmol) in N,N-dimethylformamide (20 ml). After 6 hours sodium bisulfite solution (30 ml) was added and the solution poured into ice water (500 ml). The precipitate was collected by filtration washing with water and methanol to give a cream coloured solid (15.7 g, 86%). $^1$H NMR (250 MHz, DMSO-$d_6$) δ15.42 (1H, br s), 13.33 (1H, br s), 8.50 (1H, s), 2.60 (3H, s); MS (ES$^+$) m/z 280 [MH]$^+$.

b) Methyl 4-chloro-3-iodo-2-methyl-5-pyridinecarboxylate

To phosphorus oxychloride (60 ml) at 95° C. was added the product of Example 82a (5.0 g, 58.1 mmol) in one portion and the mixture was heated at 60° C. for 35 minutes under an atmosphere of dry nitrogen. The volatiles were removed in vacuo and the residue was azeotroped with toluene. The residue was diluted with $CH_2Cl_2$ (100 ml), cooled in an ice bath, methanol (8 ml) was added dropwise and the solution allowed to warm to ambient temperature over 1 hour. The residue was cooled in an ice bath, and quenched by cautious addition of saturated aqueous $NaHCO_3$. The aqueous layer was extracted with $CH_2Cl_2$ (3×100 ml), and the combined organic extracts were dried ($Na_2SO_4$) and evaporated. The crude product was purified by flash chromatography (silica gel, $CH_2Cl_2$ followed by 10% $CH_3CO_2C_2H_5/CH_2Cl_2$) to give a cream coloured solid (4.67 g, 84%). $^1$H NMR (360 MHz, CDCl$_3$) δ8.78 (1H, s), 3.96 (3H, s), 2.91 (3H, s); MS (ES$^+$) m/z 312/314 [MH]+.

c) 2-(4-Chlorophenyl)-2,5-dihydro-7-iodo-6-methylpyrazolo[4 3-c]pyridin-3-one

Following a similar procedure to that described in Example 49c, except using the product of Example 82b instead of the product of Example 49b, the title compound was prepared as a yellow solid. $^1$H NMR (360 MHz, DMSO-$d_6$) δ12.66 (1H, br s), 8.54 (1H, s), 8.23 (2H, d, J 9.0 Hz), 7.48 (2H, d, J 9.0 Hz), 2.54 (3H, s); MS (ES$^+$) m/z 386/388 [MH]+. Anal. found: C, 40.73; H, 2.21; N, 10.66. $C_{13}H_9ClIN_3O$ requires: C, 40.49; H, 2.35; N, 10.90%.

EXAMPLE 83

2-(4-Chlorophenyl)-2,5-dihydro-7-(2-ethoxycarbonylethenyl)-6-methyl-pyrazolo[4,3-c]-pyridin-3-one To a degassed solution of the product of Example 81c (0.15 g, 0.44 mmol), ethyl acrylate (0.14 ml, 1.3 mmol) and triethylamine (0.19 ml, 1.3 mmol) in N,N-dimethylformamide (4 ml) in an ACE® pressure tube was added tri-o-tolylphosphine (0.004 g) and palladium acetate (0.001 g). The tube was flushed with nitrogen, sealed and heated at 100° C. for 18 hours. The solvent was removed it vacuo and the crude product was purified by flash chromatography (silica gel, 5% MeOH/$CH_2Cl_2$) to give the product as a red solid (0.082 g, 52%). 1H NMR (360 MHz, DMSO-$d_6$) δ12.69 (1H, br s), 8.54 (1H, s), 8.19 (2H, d, J 8.9 Hz), 7.73 (1H, d, J 15.4 Hz), 7.54 (2H, d, J 8.9 Hz), 7.49 (1H, d, J 15.4 Hz), 4.23 (2H, q, J 7.1 Hz), 2.57 (3H, s), 1.29 (3H, t, J 7.1 Hz); MS (ES$^+$) m/z 358/360 [MH]$^+$. Anal. found: C, 58.72; H, 4.67; N, 11.25. $C_{18}H_{16}ClN_3O_3 \cdot 0.5H_2O$ requires: C, 58.94; H, 4.67; N, 11.45%.

EXAMPLE 84

7-(2-Carboxamidoethenyl)-2-(4-chlorophenyl)-2,5-dihydro-6-methylpyrazolo[4,3-c]pyridin-3-one Ammonia gas was bubbled through a suspension of the product of Example 83 (0.06 g, 0.17 mmol) in methanol (5 ml) in an ACE® pressure tube at 0° C. for 30 minutes. The tube was then sealed and heated at 100° C. for 48 hours. The solvent was removed in vacuo and the crude product was purified by flash chromatography (silica gel, 10% MeOH/$CH_2Cl_2$) to give the product as an orange solid (0.023 g, 42%). $^1$H NMR (360 MHz, DMSO-$d_6$) δ12.57 (1H, br s), 8.50 (1H, s), 8.38 (2H, d, J 9.0 Hz), 7.85 (1H, s), 7.64 (1H, d, J 15.4 Hz), 7.57 (1H, d, J 15.4 Hz), 7.46 (2H, d, J9.0 Hz), 2.54 (3H, s); MS (ES$^+$) m/z 329/331 [MH]$^+$.

EXAMPLE 85

2-(4-Chlorophenyl)-2,5-dihydro-6-methyl-7-[2-(pyridin-4-yl)ethenyl]-pyrazolo[4,3-c]pyridin-3-one Following a similar procedure to that described in Example 83, except using 4-vinylpyridine instead of ethyl acrylate, the title compound was prepared as an orange solid. $^1$H NMR (360 MHz, DMS-d$_6$) δ12.57 (1H, br s), 8.59 (2H, d, J 5.4 Hz), 8.49 (1H, s), 8.32 (3H, m), 7.66 (3H, m), 7.51 (2H, d, J 8.9 Hz), 2.62 (3H, s); MS (ES$^+$) m/z 363/365 [MH]$^+$.

EXAMPLE 86

7-Benzyl-2-(4-chlorophenyl)-2,5-dihydro-6-methylpyrazolo[4,3-c]pyridin-3-one

To a degassed solution of the product of Example 82c (0.091 g, 0.24 mmol) and benzyltributylstannane (0.18 g, 0.47 mmol) in N,N-dimethylformamide (2 ml) was added tetrakis(triphenylphosphine)-palladium(0) (0.27 g, 0.02 mmol) and the solution heated at 120° C. for 24 hours. The solvent was removed in vacuo and the crude product was purified by flash chromatography (silica gel, 3% MeOH/CH$_2$Cl$_2$) to give the product as a yellow solid (0.029 g, 35%). $^1$H NMR (360 MHz, DMSO-d$_6$) δ12.29 (1H, br s), 8.48 (1H, s), 8.25 (2H, d, J9.0 Hz), 7.47 (2H, d, J9.0 Hz), 7.34 (2H, m), 7.26 (2H, m), 7.16 (1H, m), 4.04 (2H, s), 2.34 (3H, s); MS (ES$^+$) m/z 350/352 [MH]$^+$.

EXAMPLE 87

2-(4-Chlorophenyl)-2,5-dihydro-6-methyl-7-[2-(pyridin-4-yl)ethyl]pyrazolo[4,3-c]pyridin-3-one Following a similar procedure to that described in Example 77, except using the product of Example 85 instead of the product of Example 76, the title compound was prepared as a pale yellow solid. $^1$H NMR (360 MHz, DMSO-d$_6$) δ12.17 (1H, br s), 8.45 (3H, m), 8.25 (2H, d, J 9.0 Hz), 7.47 (2H, d, J 9.0 Hz), 7.25 (2H, d, J 5.9 Hz), 2.98 (2H, s), 2.18 (3H, s); MS (ES$^+$) m/z 365/367 [MH]$^+$.

EXAMPLE 88

7-(2-Carboxamidoethyl)-2-(4-chlorophenyl)-2,5-dihydro-6-methylpyrazolo[4,3-c]pyridin-3-one To a solution of the product of Example 84 (0.1 g, 0.3 mmol) in butanol (8 ml) was added platinum oxide (0.01 g, 44 μmol) and the mixture stirred vigorously under an atmosphere of hydrogen for 4 hours. The solvent was removed in vacuo and the crude product recystallised from CH$_3$CO$_2$C$_2$H$_5$/MeOH/CH$_2$Cl$_2$ to give the product as a yellow solid (0.061 g, 61%). $^1$H NMR (360 MHz, DMSO-d$_6$) δ12.20 (1H, br s), 8.44 (1H, s), 8.25 (2H, d, J 9.0 Hz), 7.46 (2H, d, J 9.0 Hz), 7.30 (1H, br s), 6.76 (1H, br s), 2.86 (2H, t, J 7.3 Hz), 2.47 (2H, t, J 7.3 Hz), 2.37 (3H, s); MS (ES$^+$) m/z331/333 [MH]$^+$.

EXAMPLE 89

2-(4-Chlorophenyl)-2,5-dihydro-6-methyl-7-[2-(pyridin-2-yl)ethenyl]-pyrazolo[4,3-c]pyridin-3-one Following a similar procedure to that described in Example 83, except using 2-vinylpyridine instead of ethyl acrylate, the title compound was prepared as an orange/red coloured solid. $^1$H NMR (360 MHz, DMSO-d$_6$) δ12.57 (1H, br s), 8.61 (2H, d, J 5.4 Hz), 8.49 (1H, s), 8.32 (3H, m), 7.82 (3H, m), 7.63 (1H, d, J 7.8 Hz), 7.53 (2H, d, J 8.9 Hz), 7.28 (1H, m), 2.60 (3H, s); MS (ES$^+$) m/z 363/365 [MH]$^+$. Anal. found: C, 64.63; H, 3.81; N, 14.86. C$_{20}$H$_{15}$ClN$_4$O.0.4H$_2$O requires: C, 64.91; H, 4.30; N, 15.14%.

EXAMPLE 90

2-(4-Chlorophenyl)-2,5-dihydro-7-(3-dimethylaminoprop-1-ynyl)-6-methyl-pyrazolo[4,3-c]pyridin-3-one To a degassed solution of the product of Example 82c (0.25 g, 0.64 mmol) and N,N-dimethylpropargylamine (0.11 ml, 1.0 mmol) in piperidine (4 ml) was added copper(I) iodide (0.0012 g, 6.5 μmol), tri(2-furyl)phosphine (0.03 g, 0.4 mmol) and tris(dibenzylideneacetone)dipalladium(0) (0.03 g, 30 μmol), and the mixture heated at 100° C. for 18 hours. The solvent was removed in vacuo and the crude product purified by flash chromatography (silica gel, 5% MeOH/CH$_2$Cl$_2$). Recrystallisation from MeOH/CH$_2$Cl$_2$/CH$_3$CO$_2$C$_2$H$_5$ afforded the title compound as a yellow/orange solid (0.089 g, 40.3%). $^1$H NMR (360 MHz, DMSO-d$_6$) δ12.53 (1H, br s), 8.52 (1H, s), 8.21 (2H, d, J 8.9 Hz), 7.47 (2H, d, J 8.9 Hz), 3.66 (2H, s), 2.49 (3H, s), 2.36 (6H, s); MS (ES$^+$) m/z 341/343 [MH]$^+$, 296/298 [(M-(NMe$_2$))H]$^+$.

EXAMPLE 91

2-(4-Chlorophenyl)-2,5-dihydro-6-methyl-7-(thien-3-yl)pyrazolo[4,3-c]pyridin-3-one To a degassed solution of the product of Example 81c (0.227 g, 0.8 mmol), thiophene-3-boronic acid (0.227 g, 1.7 mmol) and water (0.5 ml) in N,N-dimethylformamide (4 ml) in an ACE® pressure tube was added tetrakis(triphenylphosphine)palladium(0) (0.02 g, 17 μmol) and the mixture heated at 120° C. for 18 hours. The reaction was diluted with ethyl acetate and the solid which precipitated was collected by filtration, and washed with ethyl acetate. Recrystallisation from MeOH/CH$_2$Cl$_2$/CH$_3$CO$_2$C$_2$H$_5$ afforded the title compound as a yellow solid (0.234 g, 77%). $^1$H NMR (360 MHz, DMSO-d$_6$) δ12.44 (1H, br s), 8.56 (1H, s), 8.19 (2H, d, J 9.0 Hz), 7.87 (1H, dd, J4.7 Hz, J2.9 Hz), 7.67 (1H, m), 7.50 (1H, d, J 4.7 Hz), 7.43 (2H, d, J 9.0 Hz), 2.39 (3H, s); MS (ES$^+$) m/z 341/343 [MH]$^+$; Anal. found: C, 59.65; H, 3.34; N, 12.28. C$_{17}$H$_{12}$ClN$_3$OS requires: C, 59.74; H, 3.54; N, 12.28%.

EXAMPLE 92

2-(4-Chlorophenyl)-3,5-dihydro-6-methyl-3-oxo-2H-pyrazolo[4,3-c]pyridine-7-carboxylic acid ethyl ester Carbon monoxide was bubbled through a suspension of the product of Example 82c (0.25 g, 0.65 mmol), triethylamine (0.18 ml, 1.3 mmol), sodium carbonate (0.13 g, 1.3 mmol) and dichlorobis(triphenylphosphine)-palladium(II) (0.023 g, 32 μmol) in ethanol (8 ml) for 30 minutes, then the reaction was heated at reflux for 18 hours under an atmosphere of carbon monoxide. The solvent was removed in vacuo and the crude product purified by flash chromatography (silica gel, 5% MeOH/CH$_2$Cl$_2$) to give the title compound as an orange solid (0.182 g, 85%). $^1$NMR (400 MHz, DMSO-d$_6$) δ12.53 (1H, br s), 8.56 (1H, s), 8.20 (2H, d, J 9.0 Hz), 7.47 (2H, d, J 9.0 Hz), 3.36 (2H, q, J 7.0 Hz), 2.46 (3H, s), 1.35 (3H, t, J 7.0 Hz); MS (ES$^+$) m/z 332/334 [MH]$^+$.

EXAMPLE 93

2-(4-Chlorophenyl)-2,5-dihydro-7-[2-(imidazol-1-yl)ethenyl]-6-methyl-pyrazolo[4,3-c]pyridin-3-one To a degassed solution of the product of Example 81c (0.3 g, 0.88 mmol), 1-vinylimidazole (0.24 ml, 2.6 mmol), and triethylamine (0.24 ml, 2.6 mmol) in N,N-dimethylformamide (4 ml) in an ACE® pressure tube was added tri(2-furyl)phosphine (0.082 g, 0.35 mmol), tris (dibenzylideneacetone)-dipalladium(0) (0.04 g, 44 mol) and the mixture heated at 120° C. for 72 hours. The solvent was removed in vacuo and the crude product purified by flash chromatography (silica gel, 5% MeOH/CH$_2$Cl$_2$). Recrystallisation from MeOH/CH$_2$Cl$_2$/CH$_3$CO$_2$C$_2$H$_5$ afforded the title compound as a yellow solid (0.115 g, 37%). $^1$H NMR (360 MHz, DMSO-d$_6$) δ12.56 (1H, br s), 8.80 (1H, d, J 14.0 Hz), 8.48 (1H, s), 8.36 (2H, d, J 9.0 Hz), 8.26 (1H, s), 7.94 (1H, s), 7.48 (2H, d, J 9.0 Hz), 7.12 (1H, d, J 14.0 Hz), 7.09 (1H, s), 2.57 (3H, s); MS (ES$^+$) m/z 352/354 [MH]$^+$.

EXAMPLE 94

2-(4-Chlorophenyl)-2,5-dihydro-7-ethyl-6-methylpyrazolo[4,3-c]pyridin-3-one

Following a similar procedure to that described in Example 86, except using the product of Example 81c instead of the product of Example 82c and tetraethyltin instead benzyltributylstannane, the title compound was prepared as a yellow solid. $^1$H NMR (360 MHz, CD$_3$OD) δ8.20 (1H, s), 8.13 (2H, d, J8.9 Hz), 7.39 (2H, d, J8.9 Hz), 2.8 (2H, q, J7.5 Hz), 2.38 (3H, s), 1.27 (2H, t, J 7.5 Hz); MS (ES$^+$) m/l 288/290 [MH]$^+$.

EXAMPLE 95

2-(4-Chlorophenyl)-2,5-dihydro-7-(2-methylprolyl)-6-methyl]pyrazolo[4,3-c]pyridin-3-one Zinc dust (0.29 g, 6.0 mmol) and 1,2-dibromoethane (25 μl, 0.3 mmol) in N,N-dimethylformamide (2 ml) were heated at 50° C. for 20 minutes. 1-Iodo-2-methylpropane (0.7 ml, 6.1 mmol) was then added and the mixture heated at 50° C. for 3 hours. The resulting mixture was added in one portion to a solution of the product of Example 82c (0.24 g, 0.62 mmol), tri(2-furyl)phosphine (0.06 g, 0.3 mmol) and tris(dibenzylideneacetone)-dipalladium(0) (0.03 g, 33 μmol) at 50° C. The solution was then heated at 80° C. for 15 hours. The solvent was removed in vacuo and the crude product purified by flash chromatography (silica gel, 5% MeOH/CH$_2$Cl$_2$). Recrystallisation from CH$_2$Cl$_2$/isohexane afforded the title compound as a yellow solid (0.038 g, 19%). $^1$H NMR (360 MHz, DMSO-d$_6$) δ12.20 (1H, br s), 8.43 (1H, d, J 6.3 Hz), 8.23 (2H, d, J 8.9 Hz), 7.46 (2H, d, J8.9 Hz), 2.56 (2H, d, J7.3 Hz), 2.33 (3H, s), 2.18 (1H, m), 0.93 (6H, d, J 6.6 Hz); MS (ES$^+$) m/z 316/318 [MH]$^+$.

EXAMPLE 96

2-(4-Chlorophenyl)-2,5-dihydro-6-methyl-7-[2-(pyridin-2-yl)ethyl]pyrazolo[4,3-c]pyridin-3-one Following a similar procedure to that described in Example 77, except using the product of Example 89 instead of the product of Example 76, the title compound was prepared as a pale yellow solid. $^1$H NMR (360 MHz, DMSO-d$_6$) δ12.16 (1H, s), 8.51 (1H, m), 8.43 (1H, s), 8.26 (2H, d, J 9.0 Hz), 7.67 (1H, m), 7.47 (2H, d, J 9.0 Hz), 7.20 (2H, m), 3.07 (4H, m), 2.16 (3H, s); MS (ES$^+$) m/z 365/367 [MH]$^+$.

EXAMPLE 97

2-(4-Chlorophenyl)-2,5-dihydro-6-methyl-7-[2-(piperidin-2-yl)ethyl]-pyrazol[4,3-c]pyridin-3-one The title product was also isolated from the reaction of Example 96 as a yellow solid. $^1$H NMR (360 MHz, DMSO-d$_6$) δ12.16 (1H, s), 8.37 (1H, s), 8.28 (2H, d, J 9.0 Hz), 7.44 (2H, d, J 9.0 Hz), 2.95 (2H, d, J 12.3 Hz), 2.72 (2H, t, J 7.0 Hz), 2.44 (2H, m), 2.32 (3H, s), 1.66 (4H, m), 1.49 (1H, m), 1.28 (2H, m), 1.11 (1H, in); MS (ES$^+$) m/z 371/373 [MH]$^+$. Anal. found: C, 62.66; H, 6.15; N, 14.54. C$_{20}$H$_{23}$ClN$_4$O.0.75H$_2$O requires: C, 62.49; H, 6.42; N, 14.57%.

EXAMPLE 98

2-(4-Chlorphenyl)-2,5-dihydro-6-methyl-7-[3-(morpholin-4-yl)prop-1-ynyl]-pyrazolo[4,3-c]pyridin-3-one a) 2-(4-Chlorophenyl)-2,5-dihydro-7-(3-hydroxyprop-1-ynyl)-6-methyl-pyrazolo[4,3-c]pyridin-3-one Following a similar procedure to that described in Example 68, except using the product of Example 82c instead of the product of Example 61b, the title compound was prepared as a yellow solid. $^1$H NMR (400 MHz, DMSO-d) δ12.61 (1H, br s), 8.52 (1H, s), 8.21 (2H, d, J 8.9 Hz), 7.47 (2H, d, J 8.9 Hz), 5.43 (1H, t, J 5.9 Hz), 4.41 (2H, d, J 5.7 Hz), 2.48 (3H, s); MS (ES$^+$) m/z 314/316 [MH]$^+$.

b) 2-(4-Chlorophenyl)-7-(3-chloropro)-1-ynyl)-2 5-dihydro-6-methyl-pyrazolo[4,3-c]pyridin-3-one Following a similar procedure to that described in Example 74a, except using the product of Example 98a instead of the product of Example 68, the title compound was prepared as a yellow solid. m/z 332/334/336 [MH]$^+$.

c) 2-(4-Chlorophenyl)-2,5-dihydro-6-methyl-7-[3-(morpholin-4-yl)prop-1-ynyl]-pyrazolo[4,3-c]pyridin-3-one To a solution of the product of Example 98b (0.13 g, 0.4 mmol) in N,N-dimethylformamide (2 ml) was added morpholine (1 ml) and the solution stirred at ambient temperature for 2 hours. The solvent was removed in vacuo and the crude product purified by flash chromatography (silica gel, 10% MeOH/CH$_2$Cl$_2$) to give the title compound as a yellow solid (0.056 g, 37%). 1H NMR (360 MHz, DMSO-d$_6$) δ12.60 (1H, br s), 8.51 (1H, s), 8.22 (2H, d, J 9.0 Hz), 7.46 (2H, d, J 9.0 Hz), 3.66 (2H, s), 3.64 (4H, m), 2.62 (4H, m), 2.48 (3H, s); MS (ES$^+$) m/z 382/385 [MH]$^+$. Anal. found: C, 60.32; H, 5.02; N, 13.86. C$_{20}$H$_{19}$ClN$_4$O$_2$.1 H$_2$O requires: C, 59.93; H, 5.28; N, 13.98%.

EXAMPLE 99

2-(4-Chlorophenyl)-2,5-dihydro-7-hydroxymethyl-6-methylpyrazolo[4,3-c]pyridin-3-one To a degassed suspension of the product of Example 82c (1.5 g, 3.9 mmol) and tert-butyldimethylsilyloxymethyltributylstannane (3.4 g, 7.8 mmol) (prepared by an analogous procedure to that described in Synth. Commun., 1994, 24, 1117–1120) in N,N-dimethylformamide (10 ml) was added tetrakis (triphenylphosphine)palladium(0) (0.225 g, 0.38 mmol) and the mixture heated at 90° C. for 96 hours. After cooling to ambient temperature the reaction was filtered and the filtrate evaporated to give a brown oil. The oil was dissolved in ethanol (20 ml), pyridinium p-toluenesulfonate (0.5 g, 2.0 mmol) was added and the mixture was heated at 80° C. for 14 hours. The solvent was removed in vacuo and the crude product purified by flash chromatography (silica gel, 5–12% MeOH/CH$_2$Cl$_2$) to give the title compound as a yellow solid (0.563 g, 50%). $^1$H NMR (400 MHz, DMSO-d$_6$) δ12.25 (1H, br s), 8.46 (1H, d, J 4.2 Hz), 8.26 (2H, d, J 8.9 Hz), 7.46 (2H, d, J 8.9 Hz), 4.99 (1H, t, J 5.3 Hz), 4.60 (2H, d, J 5.4 Hz), 2.40 (3H, s); MS (ES$^+$) m/z 290/292 [MH]$^+$. Anal. found: C, 57.93; H, 4.19; N, 14.26. C$_{14}$Hl$_2$ClN$_3$0$_2$ requires: C, 58.04; H, 4.17; N, 14.50%.

EXAMPLE 100

2-(4-Chlorophenyl)-2,5-dihydro-6-methyl-7-[2-oxo-3-(1, 24-triazol-1-yl)propyl]-pyrazolo[4,3-c]pyridin-3-one Following a similar procedure to that described in Example 90, except using 3-(1,2,4-triazol-1-yl)prop-1-yne (prepared by an analogous procedure to that described in *Heterocycles*, 1994, 38, 1367–1374) instead of N,N-dimethylpropargylamine, the title compound was prepared as a yellow solid. $^1$H NMR (360 MHz, DMSO-$d_6$) $\delta$12.38 (1H, br s), 8.53 (1H, d, J 1.2 Hz), 8.45 (1H, s), 8.26 (2H, d, J 8.9 Hz), 7.99 (1H, s), 7.46 (2H, d, J 8.9 Hz), 5.52 (2H, s), 3.99 (2H, s), 2.29 (3H, s); MS (ES$^+$) m/z 383/38,5 [MH]$^+$. Anal. found: C, 56.22; H, 4.06; N, 21.66. $C_{18}H_{15}ClN_6O_2$ requires: C, 56.48; H, 3.95; N, 21.95%.

EXAMPLE 101

2-(4-Chlorphenyl)-2,5-dihydro-7-[3-(imidazol-1-yl)-2-oxopropyl]-6-methyl-pyrazolo[4.3-c]pyridin-3-one Following a similar procedure to that described in Example 90, except using 3-(imidazol-1-yl)prop-1-yne (prepared by an analogous procedure to that described in *Heterocycles*, 1994, 38, 1367–1374) instead of N,N-dimethylpropargylamine, the title compound was prepared as a yellow solid. 1H NMR (400 MHz, DMSO-$d_6$) $\delta$12.39 (1H, br s), 8.52 (1H, s), 8.27 (2H, d, J 8.9 Hz), 7.55 (1H, s), 7.46 (2H, d, J 8.9 Hz), 7.07 (1H, s), 6.90 (1H, s), 5.25 (2H, s), 3.94 (2H, s), 2.29 (3H, s); MS (ES$^+$) m/z 382/384 [MH]$^+$.

EXAMPLE 102

2-(4-Chlorophenyl)-2,5-dihydro-6-methyl-7-[N-(2-methyl-2H-1,2,4-triazol-3-ylmethyl)aminomethyl]pyrrazolo[4,3-c]pyridin-3-one To a solution of the product of Example 99 (0.1 g, 0.34 mmol), at −10° C. in pyridine (6 ml) was added methanesulfonyl chloride (32 μl, 4.2 mmol) and the solution stirred for 30 minutes at −10° C. then allowed to warm to room temperature over 2 hours. (2-Methyl-2H-1,2,4-triazol-3-yl)methylamine (prepared as described in EP-A-0421210) (0.5 g, 4.4 mmol) was added and the mixture heated to 60° C. for 2 hours. The solvent was removed in vacuo and the crude product purified by flash chromatography (silica gel, 8% MeOH/CH$_2$Cl$_2$) to give the title compound as a yellow solid (0.022 g, 16.9%). $^1$H NMR (360 MHz, DMSO-$d_6$) $\delta$12.55 (1H, br s), 8.59 (1H, s), 8.27 (2H, d, J 8.9 Hz), 8.06 (1H, s), 7.49 (2H, d, J 8.9 Hz), 4.47 (1s), 4.37 (1H, s), 3.84 (3H, s), 2.46 (3H, s); MS (ES$^+$) mi/z 384/386 [MH]$^+$.

EXAMPLE 103

2-(4-Chlorolphenyl)-2,5-dihydro-7-(3-methoxycarbonylpropyl)-6-methylpyrazolo[4,3-c]pyridin-3-one Following a similar procedure to that described in Example 95, except using methyl 4-iodobutyrate instead of 1-iodo-2-methylpropane, the title compound was prepared as a yellow solid. $^1$H NMR (360 MHz, DMSO-$_6$) $\delta$12.21 (1H, br s), 8.42 (1H, d, J 6.3 Hz), 8.23 (2H, d, J 8.9 Hz), 7.46 (2H, d, J 8.9 Hz), 3.57 (3H, s), 2.70 (2H, t, J 7.2 Hz), 2.39 (2H, t, J 7.2 Hz), 2.33 (3H, s), 1.90 (2H, t, J 7.2 Hz); MS (ES$^+$) 7m/z 360/362 [MH]$^+$. Anal. found: C, 59.64; H, 4.82; N, 11.30. $C_{18}H_{18}ClN_3O_3$.0.1 H$_2$O requires: C, 59.79; H, 5.07; N, 11.62%.

EXAMPLE 104

7-(3-Carboxamidopropyl)-2-(4-chlorophenyl)-2,5-dihydro-6-methyl-pyrazolo[4,3-c]pyridin-3-one Following a similar procedure to that described in Example 84, except using the product of Example 103 instead of the product of Example 83, the title compound was prepared as a yellow solid. $^1$H NMR (360 MHz, DMSO-$d_6$) $\delta$12.23 (1H, br s), 8.45 (1H, d, J 6.3 Hz), 8.24 (2H, d, J 9.0 Hz), 7.46 (2H, d, J 9.0 Hz), 7.27 (1H, s), 6.74 (1H, s), 2.67 (2H, t, J 7.2 Hz), 2.34 (3H, s), 2.13 (2H, t, J 7.2 Hz), 1.85 (2H, t, J 7.2 Hz); MS (ES$^+$) m/z 345/347 [MH]$^+$. Anal. found: C, 55.86; H, 5.08; N, 15.20. $C_{17}H_{17}ClN_4O_2$.1.15 H$_2$O requires: C, 55.86; H, 5.32; N, 15.33%.

EXAMPLE 105

7-(3-Benzoyloxypropyl)-2-(4-chlorophenyl)-2,5-dihydro-6-methylpyrazolo[4,3-c]pyridin-3-one Following a similar procedure to that described in Example 95, except using 3-Iodopropyl benzoate instead of 1-iodo-2-methylpropane, the title compound was prepared as a yellow solid. $^1$H NMR (360 MHz, DMSO-$_6$) $\delta$12.22 (1H, br s), 8.43 (1H, d, J 6.3 Hz), 8.20 (2H, d, J 8.9 Hz), 7.95 (2H, d, J 8.9 Hz), 7.68 (1H, m), 7.55 (2H, m), 7.37 (2H, d, J 8.9 Hz), 3.57 (3H, s), 4.33 (2H, t, J 7.2 Hz), 2.86 (2H, t, J 7.2 Hz), 2.35 (3H, s), 2.11 (2t, J 7.2 Hz); MS (ES$^+$) m/z 422/424.

EXAMPLE 106

2-(4-Chlorophenyl)-2,5-dihydro-6-methyl-7-[3-(3-methyl-1,2,4-oxadiazol-5-yl)propyl]pyrazolo[4,3-c]pyridin-3-one To a stirred suspension of ethanol (20 ml) and molecular sieves (4 Å, 5 g) was added sodium (0.18 g, 7.8 mmol); the mixture was warmed to reflux then allowed to cool to room temperature. To this mixture was added acetamide oxime (0.6 g, 8.0 mmol) followed after ten minutes by the product of Example 103 (0.250 g, 0.7 mmol) and the mixture heated at 80° C. for 2 hours. The reaction was filtered and the solvent evaporated from the filtrate in vacuo. The crude product was purified by flash chromatography (silica gel, 6% MeOH/CH$_2$Cl$_2$) to give the title compound as a yellow solid. Recrystallisation from MeOH/CH$_2$Cl$_2$/EtOAc afforded the title compound as a yellow solid (0.169 g, 63.6%). $^1$H NMR (360 MHz, DMSO-$d_6$) $\delta$12.21 (1H, br s), 8.44 (1H, d, J 6.3 Hz), 8.23 (2H, d, J 8.9 Hz), 7.46 (2H, d, J 8.9 Hz), 2.96 (2H, t, J 7.2 Hz), 2.77 (2H, t, J 7.2 Hz), 2.33 (3H, s), 2.30 (3H, s), 2.12 (2H, t, J 7.2 Hz); MS (ES$^+$) m/z 384/386 [MH]$^+$. Anal. found: C, 59.24; H, 4.44; N, 17.88. $C_{19}H_{18}ClN_{15}N_5O_2$ requires: C, 59.45; H, 4.73; N, 18.25%.

EXAMPLE 107

2-(4-Chlorophenyl)-7-(3-cyanopropyl)-2,5-dihydro-6-methylpyrazolo[4,3-c]pyridin-3-one Following a similar procedure to that described in Example 95, except using 4-iodobutyronitrile instead of 1-iodo-2-methylpropane, the title compound was prepared as a yellow solid. $^1$H NMR (360 MHz, DMSO-$_6$) $\delta$12.24 (1H, br s), 8.46 (1H, d, J 6.3 Hz), 8.26 (2H, d, J 8.9 Hz), 7.47 (2H, d, J 8.9 Hz), 2.77 (2H, t, J 7.2 Hz), 2.58 (2H, t, J 7.2 Hz), 2.36 (3H, s), 1.96 (2H, t, J 7.2 Hz); MS (ES$^+$) m/z 327/329 [MH]$^+$.

EXAMPLE 108

2-(4-Chlorophenyl)-2,5-dihydro-6-methyl-7-(pyridin-3-yl)pyrazolo[4,3-c]pyridin-3-one Following a similar procedure to that described in Example 86, except using 3-pyridyltributylstannane instead of benzyltributylstannane, the title compound was prepared as a yellow solid. $^1$H NMR (360 MHz, DMSO-$d_6$) δ12.54 (1H, br s), 8.76 (1H, d, J 1.9 Hz), 8.60 (2H, m), 8.13 (2H, d, J 9.0 Hz), 7.98 (1H, m), 7.55 (1H, m), 7.42 (2H, d, J 9.0 Hz), 2.28 (3H, s); MS (ES$^+$) m/z 337/339 [MH]$^+$.

EXAMPLE 109

2-(4-Chlorophenyl)-2,5-dihydro-7-[3-(1H-imidazol-2-yl)propyl]-6-methyl-pyrazolo[4,3-c]pyridin-3-one To a solution of the product of Example 107 (0.131 g, 0.4 mmol) and aminoacetaldehyde dimethylacetal (43 μl, 0.4 mmol) in DMSO (1 ml) was added copper(I) chloride (0.04 g, 0.4 mmol) and the mixture heated at 100° C. for 120 hours. The solvent was removed in vacuo and the residue suspended in formic acid (10 ml) and heated at 70° C. for 18 hours. The reaction was filtered and the solvent evaporated from the filtrate in vacuo. The crude product was purified by flash chromatography (silica gel, 6–10% MeOH/CH$_2$Cl$_2$) to give the title compound as a yellow solid (0.012 g, 8.1%). $^1$H NMR (360 MHz, CD$_3$OD) δ8.34 (1H, s), 8.02 (2H, d, J 8.7 Hz), 7.42 (2H, d, J8.7 Hz), 7.11 (2H, br s), 2.99 (2H, br s), 2.80 (2H, br s), 2.40 (3H, s), 2.05 (2H, br s); MS (ES$^+$) m/z 368/370 [MH]$^+$.

EXAMPLE 110

2-(4-Chlorophenyl)-2,5-dihydro-7-(3-hydroxypropyl)-6-methylpyrazolo[4,3-c]pyridin-3-one To a solution of sodium hydroxide (0.075 g, 1.88 mmol) in methanol (10 ml) was added the product of Example 105 (0.1 g, 0.42 mmol) and the mixture stirred for 18 hours. The solvent was evaporated in vacuo and the residue taken up in water and adjusted to pH 6 with 1N HCl. The yellow precipitate was extracted into 10% methanol/CH$_2$Cl$_2$ and the organic phase separated, dried, filtered and evaporated to give a yellow solid. Recrystallisation from MeOH/CH$_2$Cl$_2$/EtOAc afforded the title compound as a yellow solid (0.082 g, 60.5%). $^1$H NMR (360 MHz, DMSO-$d_6$) δ12.22 (1H, br s), 8.44 (1H, s), 8.23 (2H, d, J 8.9 Hz), 7.46 (2H, d, J 8.9 Hz), 4.54 (1H, t, J 5.3 Hz), 3.44 (2H, dt, J 5.5, J 6.2 Hz), 2.71 (2H, t, J 7.2 Hz), 2.35 (3H, s), 1.78 (2H, t, J 7.2 Hz); MS (ES$^+$) m/z 318/320 [MH]$^+$.

What is claimed is:

1. A compound of formula I, or a salt or prodrug thereof:

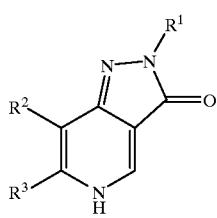

(I)

wherein

R$^1$ represents aryl or heteroaryl, either of which groups may be optionally substituted;

R$^2$ represents halogen; or C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{2-6}$ alkoxycarbonyl, C$_{1-6}$ alkylaminocarbonyl or heteroarylaminocarbonyl, any of which groups may be optionally substituted; and R$^3$ represents hydrogen, C$_{1-6}$ alkyl or trifluoromethyl.

2. A compound as claimed in claim 1 represented by formula II, and salts and prodrugs thereof.

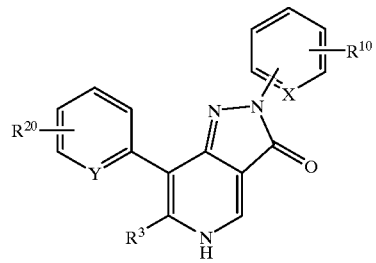

(II)

wherein

R$^3$ is as defined in claim 1;

X and Y independently represent CH or nitrogen;

R$^{10}$ represents hydrogen, C$_{1-6}$ alkyl, C$_{1-6}$ alkoxy, C$_{1-6}$ alkylsulphonyl, C$_{2-6}$ alkylcarbonyl, halogen, cyano or trifluoromethyl; and R$^{20}$ represents hydroxy(C$_{1-6}$)alkyl, aryl(C$_{1-6}$) alkylamino (C$_{1-6}$)alkyl, heteroaryl(C$_{1-6}$)alkylamino(C$_{1-6}$)alkyl, hydroxy(C$_{1-6}$)alkynyl, di(C$_{1-6}$)alkylamino(C$_{2-6}$) alkynyl, C$_{3-7}$ heterocycloalkyl, oxo(C$_{3-7}$) heterocycloalkyl, C$_{1-6}$ alkyl(C$_{3-7}$)heterocycloalkyl, C$_{2-6}$ alkoxycarbonyl(C$_{3-7}$)heterocycloalkyl, C$_{3-7}$ heterocycloalkyl(C$_{1-6}$)alkyl, C$_{3-7}$ heterocycloalkylcarbonyl, C$_{1-6}$ alkyl(C$_{3-7}$) heterocycloalkylcarbonyl, spiroheterocyclyl, heteroaryl, C$_{1-6}$ alkylheteroaryl, C$_{3-7}$ heterocycloalkyl-(C$_{1-6}$)alkylheteroaryl, C$_{1-6}$ alkyl(C$_{3-7}$)heterocycloalkyl (C$_{1-6}$)alkylheteroaryl, heteroaryl(C$_{1-6}$)alkyl, heteroaryl (C$_{2-6}$)alkynyl, hydroxy, C$_{1-6}$ alkoxy, amino, di(C$_{1-6}$) alkylamino, C$_{2-6}$ alkylcarbonylamino, C$_{1-6}$ alkylsulphonylamino, C$_{3-7}$ cycloalkyl(C$_{1-6}$) alkylamino, di[(C$_{3-7}$)cycloalkyl(C$_{1-6}$)alkyl]amino, heteroaryl(C$_{1-6}$)alkylamino, C$_{1-6}$ alkylaminocarbonylamino, amino(C$_{1-6}$) alkylcarbonylamino, C$_{2-6}$ alkoxycarbonylamino-(C$_{1-6}$) alkylcarbonylamino, C$_{1-6}$ alkoxycarbonyl, aminocarbonyl, halogen, cyano or nitro.

3. A compound as claimed in claim 1 wherein R$^3$ represents hydrogen, methyl or ethyl.

4. A compound as claimed in claim 2 wherein R$^{10}$ represents hydrogen, methyl, methoxy, fluoro or chloro.

5. A compound as claimed in claim 2 wherein R$^{20}$ represents hydroxymethyl, benzylaminomethyl, pyridinylmethylaminomethyl, hydroxypropynyl, dimethylaminopropynyl, piperazinyl, morpholinyl, pyrrolidinonyl, methyl-piperazinyl, tert-butoxycarbonyl-piperazinyl, pyrrolidinylmethyl, pyrrolidinylcarbonyl, methyl-piperazinylcarbonyl, 1-oxa-8-azaspiro[4.5]dec-3-en-3-yl, pyridinyl, thienyl, thiazolyl, imidazolyl, azabenzimidazolyl, oxadiazolyl, triazolyl, methylimidazolyl, morpholinylmethyl-triazolyl, methylpiperazinylmethyl-triazolyl, pyridinylethyl, pyridinylethynyl, hydroxy, methoxy, amino, dimethylamino, acetylamino, methylsulphonylamino, cyclopropylmethylamino, di(cyclopropylmethyl)amino, pyridinylmethylamino, ethylaminocarbonylamino, 2-amino-2-methylpropionamido, tert-butoxycarbonylaminomethyl-carbonylamino, methoxycarbonyl, aminocarbonyl, chloro, iodo, cyano or nitro.

6. A compound selected from:
2,5-dihydro-2,7-diphenylpyrazolo[4,3-c]pyridin-3-one;
2,5-dihydro-2-phenyl-7-propylpyrazolo[4,3-c]pyridin-3-one;
2,5-dihydro-2-(4-methoxyphenyl)-7-propylpyrazolo[4,3-c]pyridin-3-one;
2-(4-chlorophenyl)-2,5-dihydro-7-propylpyrazolo[4,3-c]pyridin-3-one;
7-benzyl-2-(4-chlorophenyl)-2,5-dihydropyrazolo[4,3-c]pyridin-3-one;
7-benzyl-2,5-dihydro-2-(4-methoxyphenyl)pyrazolo[4,3-c]pyridin-3-one;
3,5-dihydro-3-oxo-2-phenyl-2H-pyrazolo[4,3-c]pyridine-7-carboxylic acid propylamide;
3,5-dihydro-3-oxo-2-phenyl-2H-pyrazolo[4,3-c]pyridine-7-carboxylic acid thiazol-2-ylamide;
2-(4-chlorophenyl)-2,5-dihydro-6-methyl-7-phenylpyrazolo[4,3-c]pyridin-3-one;
2,5-dihydro-2-(4-methoxyphenyl)-6-methyl-7-phenylpyrazolo[4,3-c]pyridin-3-one;
2,5-dihydro-6-methyl-2,7-diphenylpyrazolo[4,3-c]pyridin-3-one;
2,5-dihydro-6-methyl-2-(4-methylphenyl)-7-phenylpyrazolo[4,3-c]pyridin-3-one;
2-(4-fluorophenyl)-2,5-dihydro-6-methyl-7-phenylpyrazolo[4,3-c]pyridin-3-one;
6-ethyl-2,5-dihydro-2-(4-methoxyphenyl)-7-phenylpyrazolo[4,3-c]pyridin-3-one;
6-ethyl-2,5-dihydro-2,7-diphenylpyrazolo[4,3-c]pyridin-3-one;
2,5-dihydro-2,7-bis(4-methoxyphenyl)-6-methylpyrazolo[4,3-c]pyridin-3-one;
2-(4-chlorophenyl)-2,5-dihydro-7-(4-methoxyphenyl)-6-methyl-pyrazolo[4,3-c]pyridin-3-one;
2,7-bis(4-chlorophenyl)-2,5-dihydro-6-methylpyrazolo[4,3-c]pyridin-3-one;
2-(4-chlorophenyl)-2,5-dihydro-7-(3-methoxyphenyl)-6-methyl-pyrazolo[4,3-c]pyridin-3-one;
2-(4-chlorophenyl)-2,5-dihydro-7-(2-methoxyphenyl)-6-methyl-pyrazolo[4,3-c]pyridin-3-one;
2-(4-chlorophenyl)-2,5-dihydro-6-methyl-7-(thiophen-2-yl)pyrazolo[4,3-c]pyridin-3-one;
2-(4-chlorophenyl)-2,5-dihydro-7-(3-iodophenyl)-6-methylpyrazolo[4,3-c]pyridin-3-one;
2-(4-chlorophenyl)-2,5-dihydro-6-methyl-7-[3-(pyridin-3-yl)phenyl]-pyrazolo[4,3-c]pyridin-3-one;
2-(4-chlorophenyl)-2,5-dihydro-6-methyl-7-[3-(thiophen-2-yl)phenyl]-pyrazolo[4,3-c]pyridin-3-one;
2-(4-chlorophenyl)-2,5-dihydro-6-methyl-7-[3-(3-methyl-1,2,4-oxadiazol-5-yl)phenyl]pyrazolo[4,3-c]pyridin-3-one;
2-(4-chlorophenyl)-2,5-dihydro-6-methyl-7-[3-(pyrrolidin-1-ylcarbonyl)phenyl]pyrazolo[4,3-c]pyridin-3-one;
2-(4-chlorophenyl)-2,5-dihydro-6-methyl-7-[3-(4-methylpiperazin-1-ylcarbonyl)phenyl]pyrazolo[4,3-c]pyridin-3-one;
2-(4-chlorophenyl)-2,5-dihydro-6-methyl-7-[3-(imidazol-1-yl)phenyl]-pyrazolo[4,3-c]pyridin-3-one;
2-(4-chlorophenyl)-2,5-dihydro-6-methyl-7-[4-(pyridin-3-yl)phenyl]-pyrazolo[4,3-c]pyridin-3-one;
2-(4-chlorophenyl)-2,5-dihydro-6-methyl-7-[4-(morpholin-4-yl)phenyl]-pyrazolo[4,3-c]pyridin-3-one;
2-(4-chlorophenyl)-2,5-dihydro-6-methyl-7-[3-nitrophenyl]pyrazolo[4,3-c]pyridin-3-one;
7-(3-aminophenyl)-2-(4-chlorophenyl)-2,5-dihydro-6-methylpyrazolo[4,3-c]pyridin-3-one;
2-(4-chlorophenyl)-2,5-dihydro-6-methyl-7-[3-(3-pyridylmethylamino)phenyl]pyrazolo[4,3-c]pyridin-3-one;
2-(4-chlorophenyl)-2,5-dihydro-6-methyl-7-[3-(dimethylamino)phenyl]-pyrazolo[4,3-c]pyridin-3-one;
N-{3-[2-(4-chlorophenyl)-3,5-dihydro-6-methyl-3-oxo-2H-pyrazolo[4,3-c]pyridin-7-yl]phenyl}methanesulphonamide;
2-(4-chlorophenyl)-2,5-dihydro-6-methyl-7-[3-(4H-1,2,4-triazol-4-yl)phenyl]pyrazolo[4,3-c]pyridin-3-one;
N-{3-[2-(4-chlorophenyl)-3,5-dihydro-6-methyl-3-oxo-2H-pyrazolo[4,3-c]pyridin-7-yl]phenyl}-N'-(ethyl)urea;
2-(4-chlorophenyl)-2,5-dihydro-6-methyl-7-[3-(4-methylpiperazin-1-yl)phenyl]pyrazolo[4,3-c]pyridin-3-one;
2,5-dihydro-2-phenyl-7-(4-pyridyl)pyrazolo[4,3-c]pyridin-3-one;
7-(4-aminophenyl)-2-(4-chlorophenyl)-2,5-dihydro-6-methylpyrazolo[4,3-c]pyridin-3-one;
7-(4-acetamidophenyl)-2-(4-chlorophenyl)-2,5-dihydro-6-methyl-pyrazolo[4,3-c]pyridin-3-one;
7-[4-(4-(tert-butoxycarbonyl)piperazin-1-yl)phenyl]-2-(4-chlorophenyl)-2,5-dihydro-6-methylpyrazolo[4,3-c]pyridin-3-one;
2-(4-chlorophenyl)-2,5-dihydro-6-methyl-7-[4-(piperazin-1-yl)phenyl]-pyrazolo[4,3-c]pyridin-3-one;
2-(4-chlorophenyl)-2,5-dihydro-6-methyl-7-[4-(pyrrolidin-2-on-1-yl)phenyl]pyrazolo[4,3-c]pyridin-3-one;
7-[4-(2-amino-2-methylpropionamido)phenyl]-2-(4-chlorophenyl)-2,5-dihydro-6-methylpyrazolo[4,3-c]pyridin-3-one;
2-(4-chlorophenyl)-2,5-dihydro-6-methyl-7-[4-(4-methylpiperazin-1-yl)phenyl]pyrazolo[4,3-c]pyridin-3-one;
7-[4-(N'-tert-butoxycarbonylglycinamido)phenyl]-2-(4-chlorophenyl)-2,5-dihydro-6-methylpyrazolo[4,3-c]pyridin-3-one;
2-(4-chlorophenyl)-2,5-dihydro-6-methyl-7-[4-(1,2,4-triazol-4-yl)phenyl]-pyrazolo[4,3-c]pyridin-3-one;
and salts and prodrugs thereof.

7. A compound selected from:
2-(4-chlorophenyl)-7-(4-cyanophenyl)-2,5-dihydro-6-methylpyrazolo[4,3-c]pyridin-3-one;
7-(3-cyanophenyl)-2-(4-chlorophenyl)-2,5-dihydro-6-methylpyrazolo[4,3-c]pyridin-3-one;
2-(4-chlorophenyl)-2,5-dihydro-6-methyl-7-[4-(pyridin-2-ylmethylamino)phenyl]pyrazolo[4,3-c]pyridin-3-one;
2-(4-chlorophenyl)-7-[4-(N,N-di(cyclopropylmethyl)amino)phenyl]-2,5-dihydro-6-methylpyrazolo[4,3-c]pyridin-3-one;
2-(4-chlorophenyl)-7-[4-(N-cyclopropylmethylamino)phenyl]-2,5-dihydro-6-methylpyrazolo[4,3-c]pyridin-3-one;
7-(4-carboxamidophenyl)-2-(4-chlorophenyl)-2,5-dihydro-6-methyl-pyrazolo[4,3-c]pyridin-3-one;
2-(4-chlorophenyl)-2,5-dihydro-7-(3-methoxycarbonylphenyl)-6-methyl-pyrazolo[4,3-c]pyridin-3-one;
2-(4-chlorophenyl)-2,5-dihydro-6-methyl-7-[3-(pyridin-2-ylmethylaminomethyl)phenyl]pyrazolo[4,3-c]pyridin-3-one;
2-(4-chlorophenyl)-2,5-dihydro-6-methyl-7-[4-(pyridin-2-ylmethylaminomethyl)phenyl]pyrazolo[4,3-c]pyridin-3-one;

7-[4-(1benzylaminomethyl)phenyl]-2-(4-chlorophenyl)-2,5-dihydro-6-methyl-pyrazolo[4,3-c]pyridin-3-one;

7-(3-carboxamidophenyl)-2-(4-chlorophenyl)-2,5-dihydro-6-methyl-pyrazolo[4,3-c]pyridin-3-one;

2-(4-chlorophenyl)-2,5-dihydro-6-methyl-7-[4-(pyrrolidin-1-ylmethyl)phenyl]-pyrazolo[4,3-c]pyridin-3-one;

2-(4-chlorophenyl)-2,5-dihydro-7-[4-(hydroxymethyl)phenyl]-6-methyl-pyrazolo[4,3-c]pyridin-3-one;

2-(4-chlorophenyl)-2,5-dihydro-7-(4-iodophenyl)-6-methylpyrazolo[4,3-c]pyridin-3-one;

2-(4-chlorophenyl)-2,5-dihydro-6-methyl-7-[4-(3-dimethylaminoprop-1-yn-1-yl)phenyl]pyrazolo[4,3-c]pyridin-3-one;

2-(4-chlorophenyl)-2,5-dihydro-7-[4-(imidazol-1-yl)phenyl]-6-methyl-pyrazolo[4,3-c]pyridin-3-one;

2-(4-chlorophenyl)-2,5-dihydro-7-[4-(imidazol-2-yl)phenyl]-6-methyl-pyrazolo[4,3-c]pyridin-3-one;

2-(4-chlorophenyl)-2,5-dihydro-6-methyl-7-[4-(1,2,3-triazol-5-yl)phenyl]-pyrazolo[4,3-c]pyridin-3-one;

2-(4-chlorophenyl)-2,5-dihydro-6-methyl-7-[4-(thiazol-2-yl)phenyl]-pyrazolo[4,3-c]pyridin-3-one;

2-(4-chlorophenyl)-2,5-dihydro-7-(4-hydroxyphenyl)-6-methylpyrazolo[4,3-c]pyridin-3-one;

2-(4-chlorophenyl)-2,5-dihydro-7-[4-(3-hydroxyprop-1-yn-1-yl)phenyl]-6-methylpyrazolo[4,3-c]pyridin-3-one;

7-[4-(6-azabenzimidazol-2-yl)phenyl]-2-(4-chlorophenyl)-2,5-dihydro-6-methylpyrazolo[4,3-c]pyridin-3-one;

7-(2-acetyl-2,3,4,9-tetrahydro-1H-pyrido[3,4-b]indol-6-yl)-2-(4-chlorophenyl)-2,5-dihydro-6-methylpyrazolo[4,3-c]pyridin-3-one;

2-(4-chlorophenyl)-7-(2-ethyl-2,3,4,9-tetrahydro-1H-pyrido[3,4-b]indol-6-yl)-2,5-dihydro-6-methylpyrazolo[4,3-c]pyridin-3-one;

2-(4-chlorophenyl)-2,5-dihydro-7-[2-(dimethylaminomethyl)indol-5-yl]-6-methylpyrazolo[4,3-c]pyridin-3-one;

7-(benzimidazol-5-yl)-2-(4-chlorophenyl)-2,5-dihydro-6-methylpyrazolo[4,3-c]pyridin-3-one;

2-(4-chlorophenyl)-2,5-dihydro-6-methyl-7-[4-(4-(morpholin-4-ylmethyl)-1,2,3-triazol-5-yl)phenyl]pyrazolo[4,3-c]pyridin-3-one;

2-(4-chlorophenyl)-2,5-dihydro-6-methyl-7-[4-(morpholin-4-methyl)-1,2,3-triazol-5-yl)phenyl]pyrazolo[4,3-c]pyridin-3-one;

2-(4-chlorophenyl)-2,5-dihydro-6-methyl-7-[4-(2-(pyridin-2-yl)ethyl-1-yn-1-yl)phenyl]pyrazolo[4,3-c]pyridin-3-one;

2-(4-chlorophenyl)-2,5-dihydro-6-methyl-7-[4-(2-(pyridin-2-yl)ethyl)phenyl]pyrazolo[4,3-c]pyridin-3-one;

2-(4-chlorophenyl)-2,5-dihydro-6-methyl-7-[4-(1-methylimidazol-2-yl)phenyl]-pyrazolo[4,3-c]pyridin-3-one;

2-(4-chlorophenyl)-2,5-dihydro-6-methyl-7-[4-(1,2,4-triazol-3-yl)phenyl]-pyrazolo[4,3-c]pyridin-3-one;

2-(4-chlorophenyl)-2,5-dihydro-6-methyl-7-[4-(1-oxa-8-azaspiro[4,5]dec-3-en-3-yl)phenyl]pyrazolo[4,3-c]pyridin-3-one;

7-bromo-2-(4-chlorophenyl)-2,5-dihydro-6-methylpyrazolo[4,3-c]pyridin-3-one;

2-(4-chlorophenyl)-2,5-dihydro-7-iodo-6-methylpyrazolo[4,3-c]pyridin-3-one;

2-(4-chlorophenyl)-2,5-dihydro-7-(2-ethoxycarbonylethenyl)-6-methyl-pyrazolo[4,3-c]pyridin-3-one;

7-(2-carboxamidoethenyl)-2-(4-chlorophenyl)-2,5-dihydro-6-methylpyrazolo[4,3-c]pyridin-3-one;

2-(4-chlorophenyl)-2,5-dihydro-6-methyl-7-[2-(pyridin-4-yl)ethenyl]-pyrazolo[4,3-c]pyridin-3-one;

7-benzyl-2-(4-chlorophenyl)-2,5-dihydro-6-methylpyrazolo[4,3-c]pyridin-3-one;

2-(4-chlorophenyl)-2,5-dihydro-6-methyl-7-[2-(pyridin-4-yl)ethyl]pyrazolo[4,3-c]pyridin-3-one;

7-(2-carboxamidoethyl)-2-(4-chlorophenyl)-2,5-dihydro-6-methylpyrazolo[4,3-c]pyridin-3-one;

2-(4-chlorophenyl)-2,5-dihydro-6-methyl-7-[2-(pyridin-2-yl)ethenyl]-pyrazolo[4,3-c]pyridin-3-one;

2-(4-chlorophenyl)-2,5-dihydro-7-(3-dimethylaminoprop-1-ynyl)-6-methyl-pyrazolo[4,3-c]pyridin-3-one;

2-(4-chlorophenyl)-2,5-dihydro-6-methyl-7-(thien-3-yl)pyrazolo[4,3-c]pyridin-3-one;

2-(4-chlorophenyl)-3,5-dihydro-6-methyl-3-oxo-2H-pyrazolo[4,3-c]pyridine-7-carboxylic acid ethyl ester;

2-(4-chlorophenyl)-2,5-dihydro-7-[2-(imidazol-1-yl)ethenyl]-6-methyl-pyrazolo[4,3-c]pyridin-3-one;

2-(4-chlorophenyl)-2,5-dihydro-7-ethyl-6-methylpyrazolo[4,3-c]pyridin-3-one;

2-(4-chlorophenyl)-2,5-dihydro-7-(2-methylpropyl)-6-methylpyrazolo[4,3-c]pyridin-3-one;

2-(4-chlorophenyl)-2,5-dihydro-6-methyl-7-[2-(pyridin-2-yl)ethyl]pyrazolo[4,3-c]pyridin-3-one;

2-(4-chlorophenyl)-2,5-dihydro-6-methyl-7-[2-(piperidin-2-yl)ethyl]-pyrazolo[4,3-c]pyridin-3-one;

2-(4-chlorophenyl)-2,5-dihydro-6-methyl-7-[3-(morpholin-4-yl)prop-1-ynyl]-pyrazolo[4,3-c]pyridin-3-one;

2-(4-chlorophenyl)-2,5-dihydro-7-hydroxymethyl-6-methylpyrazolo[4,3-c]pyridin-3-one;

2-(4-chlorophenyl)-2,5-dihydro-6-methyl-7-[2-oxo-3-(1,2,4-triazol-1-yl)propyl]-pyrazolo[4,3-c]pyridin-3-one;

2-(4-chlorophenyl)-2,5-dihydro-7-[3-(imidazol-1-yl)-2-oxopropyl]-6-methyl-pyrazolo[4,3-c]pyridin-3-one;

2-(4-chlorophenyl)-2,5-dihydro-6-methyl-7-[N-(2-methyl-2H-1,2,4-triazol-3-ylmethyl)aminomethyl]pyrazolo[4,3-c]pyridin-3-one;

2-(4-chlorophenyl)-2,5-dihydro-7-(3-methoxycarbonylpropyl)-6-methylpyrazolo[4,3-c]pyridin-3-one;

7-(3-carboxamidopropyl)-2-(4-chlorophenyl)-2,5-dihydro-6-methyl-pyrazolo[4,3-c]pyridin-3-one;

7-(3-benzoyloxypropyl)-2-(4-chlorophenyl)-2,5-dihydro-6-methylpyrazolo[4,3-c]pyridin-3-one;

2-(4-chlorophenyl)-2,5-dihydro-6-methyl-7-[3-(3-methyl-1,2,4-oxadiazol-5-yl)propyl]pyrazolo[4,3-c]pyridin-3-one;

2-(4-chlorophenyl)-7-(3-cyanopropyl)-2,5-dihydro-6-methylpyrazolo[4,3-c]pyridin-3-one;

2-(4-chlorophenyl)-2,5-dihydro-6-methyl-7-(pyridin-3-yl)pyrazolo[4,3-c]pyridin-3-one;

2-(4-chlorophenyl)-2,5-dihydro-7-[3-(1H-imidazol-2-yl)propyl]-6-methyl-pyrazolo[4,3-c]pyridin-3-one;

2-(4-chlorophenyl)-2,5-dihydro-7-(3-hydroxypropyl)-6-methylpyrazolo[4,3-c]pyridin-3-one;

and salts and prodrugs thereof.

8. A pharmaceutical composition comprising a compound of formula I as defined in claim 1 or a pharmaceutically acceptable salt thereof or a prodrug thereof in association with a pharmaceutically acceptable carrier.

9. A process for the preparation of a compound as claimed in claim 1, which comprises reacting a compound of formula III with a hydrazine derivative of formula IV, or an acid addition salt thereof:

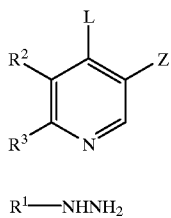

(III)

(IV)

wherein $R^1$, $R^2$ and $R^3$ are as defined in claim 1, L represents a readily displaceable group, and Z represents a reactive carboxylate moiety; and subsequently, if desired, converting a compound of formula I initially obtained into a further compound of formula I by standard methods.

10. A method for the treatment and/or prevention of anxiety which comprises administering to a patient in need of such treatment an effective amount of a compound of formula I as defined in claim 1, or a pharmaceutically acceptable salt thereof or a prodrug thereof.

* * * * *